(12) United States Patent
Okatake et al.

(10) Patent No.: US 11,774,518 B2
(45) Date of Patent: *Oct. 3, 2023

(54) MAGNETIC FIELD MEASURING APPARATUS, MAGNETIC FIELD MEASURING METHOD AND RECORDING MEDIUM WITH MAGNETIC FIELD MEASURING PROGRAM RECORDED THEREON

(71) Applicant: Asahi Kasei Microdevices Corporation, Tokyo (JP)

(72) Inventors: Shigeki Okatake, Tokyo (JP); Makoto Kataoka, Tokyo (JP); Takenobu Nakamura, Tokyo (JP); Seiichi Kato, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/952,297

(22) Filed: Sep. 25, 2022

(65) Prior Publication Data

US 2023/0023436 A1    Jan. 26, 2023

Related U.S. Application Data

(63) Continuation of application No. 17/152,700, filed on Jan. 19, 2021, now Pat. No. 11,454,679.

(30) Foreign Application Priority Data

Jan. 20, 2020 (JP) ................................ 2020-007166
Jan. 31, 2020 (JP) ................................ 2020-015430
Nov. 30, 2020 (JP) ................................ 2020-198312

(51) Int. Cl.
*G01R 33/00* (2006.01)
*G01R 33/09* (2006.01)
*A61B 5/05* (2021.01)

(52) U.S. Cl.
CPC ...... *G01R 33/0017* (2013.01); *G01R 33/0011* (2013.01); *G01R 33/0094* (2013.01); *G01R 33/09* (2013.01); *A61B 5/05* (2013.01)

(58) Field of Classification Search
CPC combination set(s) only.
See application file for complete search history.

(56) References Cited

U.S. PATENT DOCUMENTS 11,454,679 B2 * 9/2022 Okatake ............. G01R 33/0206
2006/0031038 A1 * 2/2006 Simola .................. G01R 33/02
702/127

(Continued)

FOREIGN PATENT DOCUMENTS

JP    2012152514 A    8/2012
JP    2020148760 A    9/2020
WO   2006114473 A1   11/2006

OTHER PUBLICATIONS

F Chella et al.,"Calibration of a multichannel MEG system based on the Signal Space Separation method" Physics in Medicine and Biology. 57 (2012) 4855-4870.

(Continued)

*Primary Examiner* — Alvaro E Fortich

(57) ABSTRACT

Provided is a magnetic field measuring apparatus for: acquiring the measurement data measured by a magnetic sensor array that is configured by arraying the plurality of magnetic sensor cells to form a surface covering at least a part of a target object to be measured; performing signal separation on a magnetic field spatial distribution indicated by the measurement data based on a position and magnetic sensitivity of each magnetic sensor; generating a calibration (Continued)

magnetic field at a position on a straight line that can be drawn without crossing the plurality of magnetic sensor cells from the measurement space outside the measurement space; and calibrating a sensor error for the magnetic sensor based on a separation error in a case where signal separation has been performed on a spatial distribution of the calibration magnetic field.

19 Claims, 29 Drawing Sheets

(56) References Cited

U.S. PATENT DOCUMENTS

| | | | |
|---|---|---|---|
| 2013/0214774 A1* | 8/2013 | Cesaretti | G01R 33/0023 324/252 |
| 2017/0248665 A1 | 8/2017 | Ludwig | |
| 2017/0299662 A1* | 10/2017 | Nagasaka | G01R 33/035 |
| 2017/0352800 A1 | 12/2017 | Racz | |
| 2018/0014738 A1 | 1/2018 | Tanaka | |
| 2018/0017634 A1* | 1/2018 | Ueda | G01R 33/091 |
| 2018/0275215 A1 | 9/2018 | Uchida | |
| 2018/0340987 A1* | 11/2018 | Latham | G01R 33/032 |
| 2019/0004122 A1 | 1/2019 | Jung | |
| 2019/0125268 A1 | 5/2019 | Taulu | |
| 2019/0133478 A1 | 5/2019 | Varcoe | |
| 2019/0298202 A1 | 10/2019 | Nakamura | |
| 2019/0377035 A1* | 12/2019 | Nakamura | G01R 33/09 |
| 2021/0161420 A1 | 6/2021 | Nakamura | |

OTHER PUBLICATIONS

Samu Taulu et al.,"Presentation of electromagnetic multichannel data: The signal space separation method", J Appl Phys 97, 124905,pp. 1-10, (2005).

Samu Taulu et al.,"Applications of the Signal Space Separation Method", IEEE Transactions On Signal Processing, vol. 53, No. 9, Sep. 2005, pp. 3359-3372.

Those references were submitted as IDS or found by the examiner over the earlier U.S. Appl. No. 17/152,700, filed Jan. 19, 2021.

Kensuke Sekihara,"Signal Space Separation Method for a Biomagnetic Sensor Array Arranged on a Flat Plane for Magnetocardiographic Applications: A Computer Simulation Study", Published Apr. 26, 2018, Hindawi Journal of Healthcare Engineering vol. 2018, Article ID 7689589, 19 pages https://doi.org/10.1155/2018/7689589.

* cited by examiner

MAGNETIC FIELD MEASURING APPARATUS, MAGNETIC FIELD MEASURING METHOD AND RECORDING MEDIUM WITH MAGNETIC FIELD MEASURING PROGRAM RECORDED THEREON

This application is a continuation of U.S. patent application Ser. No. 17/152,700, filed on Jan. 19, 2021, the entire contents of which are explicitly incorporated herein by reference. The application also claims priority from the following Japanese patent applications, which are explicitly incorporated herein by reference:
No. 2020-007166 filed in JP on Jan. 20, 2020
No. 2020-198312 filed in JP on Nov. 30, 2020
No. 2020-015430 filed in JP on Jan. 31, 2020

BACKGROUND

1. Technical Field

The present invention relates to a magnetic field measuring apparatus, a magnetic field measuring method and a recording medium with a magnetic field measuring program recorded thereon.

2. Related Art

Conventionally, a magnetic field measuring apparatus that measures a magnetic field emitted from the head or the chest of a subject, using a sensor platform board having a plurality of Tunnel Magneto-Resistances (TMRs) elements arranged in an array form, has been known (see, for example, Patent Document 1).

PRIOR ART DOCUMENT

Patent Document

Patent Document 1: Japanese Patent Application Publication No. 2012-152514

SUMMARY

A first aspect of the present invention provides a magnetic field measuring apparatus. The magnetic field measuring apparatus may include a magnetic sensor array that is configured by arraying a plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring apparatus may include a measurement data acquiring unit for acquiring measurement data measured by the magnetic sensor array. The magnetic field measuring apparatus may include a signal space separating unit for performing signal separation on a magnetic field spatial distribution indicated by the measurement data based on a position and magnetic sensitivity of each magnetic sensor. The magnetic field measuring apparatus may include a calibration magnetic field generating unit for generating a calibration magnetic field at a position on a straight line that can be drawn without crossing the plurality of magnetic sensor cells from the measurement space outside the measurement space where the plurality of magnetic sensor cells are not arranged in the closed space that is composed of the smallest convex polygon that includes all of the plurality of magnetic sensor cells in a cross-sectional view. The magnetic field measuring apparatus may include a calibrating unit for calibrating a sensor error for the magnetic sensor based on a separation error in a case of performing signal separation on a spatial distribution of the calibration magnetic field.

The magnetic sensor array may be composed of the plurality of magnetic sensor cells three-dimensionally arrayed in an arc shape in a cross sectional view, and an angle formed by a straight line connecting the center of a plane composed of a string connecting both end points of an arc and the center of the calibration magnetic field generating unit, and a straight line connecting a contact point between the arc and the string on the same cross section as the center of the plane, and the center of the calibration magnetic field generating unit, may be greater than 6 degrees.

Each of the plurality of magnetic sensor cells may further include a magnetic field generating unit for generating a feedback magnetic field to reduce an input magnetic field detected by the magnetic sensor, and an output unit for outputting an output signal corresponding to a feedback current that is to flow for the magnetic field generating unit to generate the feedback magnetic field.

Each of the magnetic sensors may include the magnetoresistive element and two magnetic flux concentrators arranged on both ends of the magnetoresistive element, and the magnetoresistive element may be arranged at a position sandwiched between the two magnetic flux concentrators.

The magnetic field generating unit may include a feedback coil wound along the axial direction of a magnetic field being a detection target of the magnetic sensor, so as to enclose the magnetoresistive element and the two magnetic flux concentrators.

The calibration magnetic field generating unit may have at least three or more calibration coils for generating the calibration magnetic fields in different axial directions respectively.

The different axial directions may be axial directions orthogonal to each other.

The signal space separating unit may use a position where the calibration magnetic field generating unit is arranged as a coordinate origin in a calculation in performing signal separation on a spatial distribution of the calibration magnetic field.

The signal space separating unit may perform signal separation on the magnetic field spatial distribution based on basis vectors calculated from orthonormal functions and the position and the magnetic sensitivity of each magnetic sensor.

The calibrating unit may calibrate the sensor error by changing the basis vectors.

The calibrating unit may optimize the basis vectors so as to minimize the separation error.

A synchronous detection unit for detecting the calibration magnetic field, which is an alternating magnetic field, using a signal of a frequency of the alternating magnetic field may further be included.

A frequency of the alternating magnetic field may be higher than 80 Hz (Hertz), and lower than or equal to a cutoff frequency of an attenuation property of a magnetic field by the magnetic flux concentrator.

A second aspect of the present invention provides a magnetic field measuring method. The magnetic field measuring method may include acquiring the measurement data measured by a magnetic sensor array that is configured by arraying the plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring method may include performing signal separation on a magnetic field spatial distribution indicated by the measurement data based on a position and magnetic sensitivity of each magnetic sensor. The magnetic field measuring method may include generating a calibration magnetic field at a position on a straight line that can be drawn without crossing the plurality of magnetic sensor cells from the measurement space outside the measurement space where the plurality of magnetic sensor cells are not arranged in the closed space that is composed of the smallest convex polygon that includes all of the plurality of magnetic sensor cells in a cross-sectional view. The magnetic field measuring method may include calibrating a sensor error for the magnetic sensor based on a separation error in a case of performing signal separation on a spatial distribution of the calibration magnetic field.

A third aspect of the present invention provides a recording medium with a magnetic field measuring program recorded thereon. The magnetic field measuring program may be executed by a computer. The magnetic field measuring program may cause the computer to function as a measurement data acquiring unit for acquiring measurement data measured by a magnetic sensor array that is configured by arraying the plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring program may cause the computer to function as a signal space separating unit for performing signal separation on a magnetic field spatial distribution indicated by the measurement data based on a position and a magnetic sensitivity of each magnetic sensor. The magnetic field measuring program may cause the computer to function as a calibration magnetic field generating unit for generating a calibration magnetic field at a position on a straight line that can be drawn without crossing the plurality of magnetic sensor cells from the measurement space outside the measurement space where the plurality of magnetic sensor cells are not arranged in the closed space that is composed of the smallest convex polygon that includes all of the plurality of magnetic sensor cells in a cross-sectional view. The magnetic field measuring program may cause the computer to function as a calibrating unit for calibrating a sensor error for the magnetic sensor based on a separation error in a case of performing signal separation on a spatial distribution of the calibration magnetic field.

A fourth aspect of the present invention provides a magnetic field measuring apparatus. The magnetic field measuring apparatus may include a magnetic sensor array that is configured by arraying the plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring apparatus may include a measurement data acquiring unit for acquiring measurement data measured by a magnetic sensor cell group that is at least a part of the plurality of magnetic sensor cells in the magnetic sensor array. The magnetic field measuring apparatus may include a signal space separating unit for performing signal separation on a magnetic field spatial distribution indicated by the measurement data based on a position and a magnetic sensitivity of each magnetic sensor of the magnetic sensor cell group. The magnetic field measuring apparatus may include a calibration magnetic field generating unit for generating a calibration magnetic field at a plurality of different positions. The magnetic field measuring apparatus may include a calibrating unit for calibrating a sensor error in the magnetic sensor of a first magnetic sensor cell group of the plurality of magnetic sensor cells based on the separation error in a case of performing signal separation on a spatial distribution of the calibration magnetic field generated at a first position, and calibrating the sensor error in the magnetic sensor of the second magnetic sensor cell group of the plurality of magnetic sensor cells based on a separation error in a case of performing signal separation on a spatial distribution of the calibration magnetic field generated at a second position.

The fifth aspect of the present invention provides a magnetic field measuring method. The magnetic field measuring method may include acquiring measurement data measured by a magnetic sensor cell group that is at least a part of the plurality of magnetic sensor cells in a magnetic sensor array, which is configured by arraying the plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring method may include performing signal separation on a magnetic field spatial distribution indicated by the measurement data based on a position and magnetic sensitivity of each magnetic sensor of the magnetic sensor cell group. The magnetic field measuring method may include generating a calibration magnetic field at a plurality of different calibration positions. The magnetic field measuring method may include calibrating a sensor error in the magnetic sensor of a first magnetic sensor cell group of the plurality of magnetic sensor cells based on the separation error in a case of performing signal separation on a spatial distribution of the calibration magnetic field generated at a first position, and calibrating the sensor error in the magnetic sensor of the second magnetic sensor cell group of the plurality of magnetic sensor cells based on a separation error in a case of performing signal separation on a spatial distribution of the calibration magnetic field generated at a second position.

A sixth aspect of the present invention provides a recording medium with magnetic field measuring program recorded thereon. The magnetic field measuring program may be executed by a computer. The magnetic field measuring program may cause the computer to function as a measurement data acquiring unit for acquiring measurement data measured by a magnetic sensor cell group that is at least a part of the plurality of magnetic sensor cells in a magnetic sensor array, which is configured by arraying the plurality of magnetic sensor cells to form a surface covering at least a part of a target object to be measured, each of the plurality of magnetic sensor cells having a magnetic sensor including a magnetoresistive element and a magnetic flux concentrator. The magnetic field measuring program may cause the computer to function as a signal space separating unit for performing signal separation on a magnetic field spatial distribution indicated by the measurement data based on a position and a magnetic sensitivity of each magnetic sensor of the magnetic sensor cell group. The magnetic field measuring program may cause the computer to function as a calibration magnetic field generating unit for generating a calibration magnetic field at a plurality of different positions. The magnetic field measuring program may cause the computer to function as a calibrating unit for calibrating a sensor error in the magnetic sensor of a first magnetic sensor cell group of the plurality of magnetic sensor cells based on the separation error in a case of performing signal separation on a spatial distribution of the calibration magnetic field generated at a first position, and calibrating the sensor error in the magnetic sensor of the second magnetic sensor cell group of the plurality of magnetic sensor cells based on a separation error in a case of performing signal separation on a spatial distribution of the calibration magnetic field generated at a second position.

The summary clause does not necessarily describe all necessary features of the embodiments of the present invention. The present invention may also be a sub-combination of the features described above.

DESCRIPTION OF EXEMPLARY EMBODIMENTS

Hereinafter, the present invention will be described through embodiments of the invention, but the following embodiments do not limit the invention according to the claims. In addition, all combinations of features described in the embodiments are not necessarily essential to solutions provided by the present invention.

Figure 1:
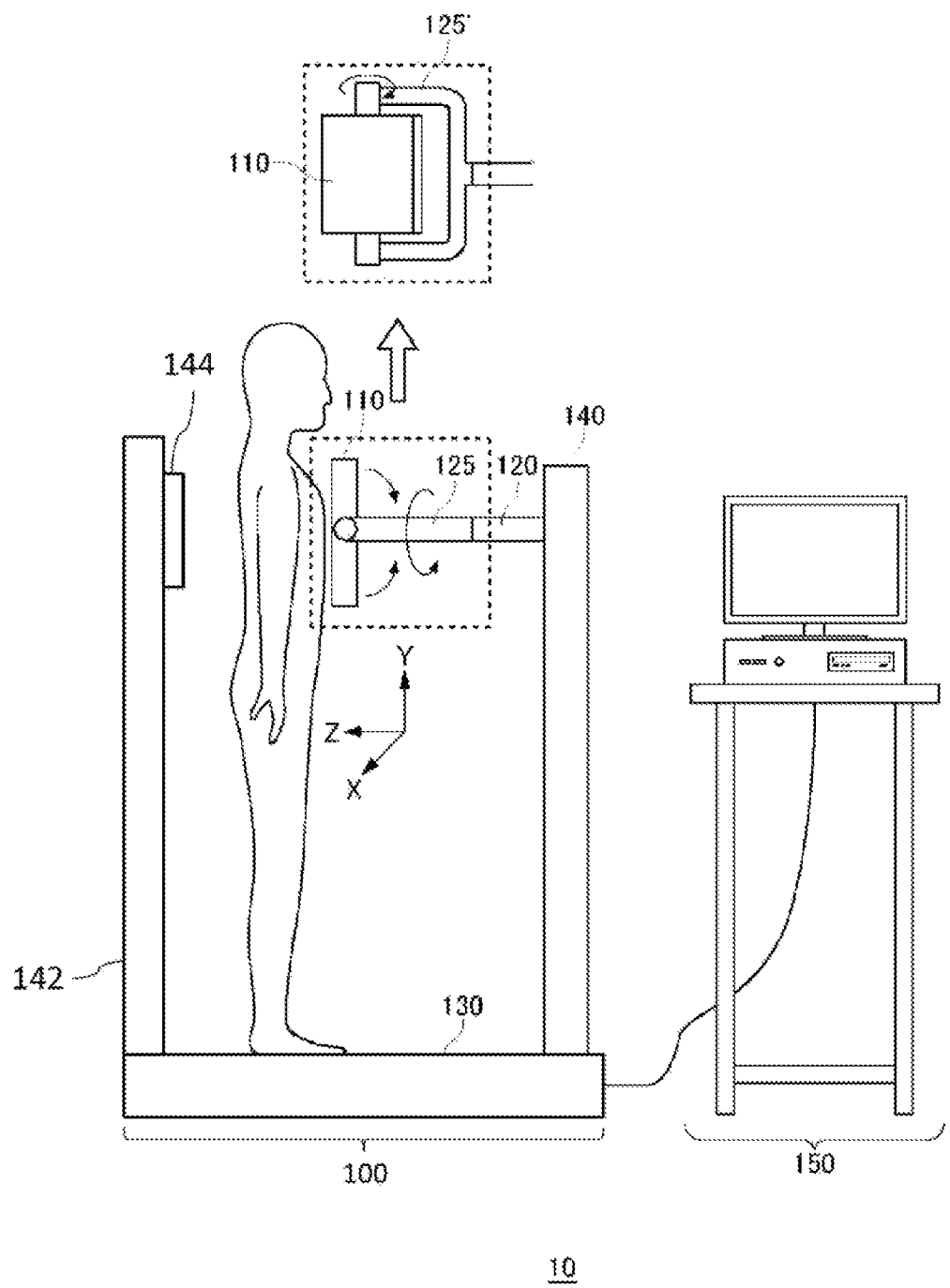
FIG. 1 illustrates a configuration of a magnetic field measuring apparatus 10 according to this embodiment.

FIG. 1 illustrates a configuration of a magnetic field measuring apparatus 10 according to this embodiment. The magnetic field measuring apparatus 10 generates a calibration magnetic field and calibrates an error (performs a calibration) in a magnetic sensor based on a result of the measurement of the calibration magnetic field when measuring the targeted magnetic field using the magnetic sensor. In this embodiment, the case where the magnetic field measuring apparatus 10 is a cardiac magnetic field measuring apparatus, for measuring the cardiac magnetic field that is a magnetic field generated by an electrical activity of a human heart, is described as one example. However, it is not limited to this. The magnetic field measuring apparatus 10 may be used for measuring the cardiac magnetic field of a non-human living organism, or may be used for measuring a biological magnetic field other than the cardiac magnetic field, such as a brain magnetic field. The magnetic field measuring apparatus 10 may also be used for magnetic particle testing for detecting surface and subsurface scratches, and so on, of steel materials and welding portions.

The magnetic field measuring apparatus 10 includes a main unit 100 and an information processing unit 150. The main unit 100 is a component for sensing the cardiac magnetic field of a subject, including a magnetic sensor unit 110, a head 120, a driving unit 125, a base portion 130, a pole portion 140, a support portion 142, and a calibration magnetic field generating unit 144.

The magnetic sensor unit 110 is arranged in a position toward the heart in the chest of a subject during a cardiac magnetic field measurement to sense the cardiac magnetic field of the subject. The head 120 supports the magnetic sensor unit 110 and causes the magnetic sensor unit 110 to face the subject when measuring the cardiac magnetic field. Also, the head 120 may be capable of extending and contracting in the z axis direction, and extend to cause the magnetic sensor unit 110 to face the calibration magnetic field generating unit 144 when performing a calibration. The driving unit 125 is provided between the magnetic sensor unit 110 and the head 120, and changes the orientation of the magnetic sensor unit 110 with respect to the head 120 when performing a calibration. The driving unit 125 according to this embodiment includes a first actuator that can cause the magnetic sensor unit 110 to rotate 360 degrees about a Z axis in the figure and a second actuator that causes the magnetic sensor unit 110 to rotate about an axis perpendicular to the Z axis (the X axis for the state in the figure), and changes the azimuth angle and zenith angle of the magnetic sensor unit 110 using these actuators. As illustrated as the driving unit 125 in the figure, the driving unit 125 is Y-shaped when viewed from the Y axis direction in the figure, and the second actuator can cause the magnetic sensor unit 110 to rotate 360 degrees about the X axis in the figure.

The base portion 130 is a base platform that supports other components, and is a platform which the subject steps on during a cardiac magnetic field measurement in this embodiment. The pole portion 140 supports the head 120 at the height of the chest of the subject. The pole portion 140 may be capable of extending and contracting in the up-down direction in order to adjust the height of the magnetic sensor unit 110 to the height of the chest of the subject.

The support portion 142 supports the calibration magnetic field generating unit 144 to be at the same height as the magnetic sensor unit 110 during a calibration. The above description has shown, as an example, the case of causing the head 120 to extend and to face the magnetic sensor unit 110 to the calibration magnetic field generating unit 144 when performing a calibration. However, it is not limited to this. The support portion 142 may also be moveable in the Z axis direction so that the calibration magnetic field generating unit 144 becomes moveable between the calibration position facing the magnetic sensor unit 110 and a retracting position away from the calibration position.

The calibration magnetic field generating unit 144 generates a calibration magnetic field during a calibration. Such a calibration magnetic field may be an alternating magnetic field. As one example, the calibration magnetic field may be a sine-wave with a frequency f0, or may be a sum of sine-waves with a plurality of frequencies (for example, frequency f0, frequency f1 (>frequency f0), frequency f2 (>frequency f1) and the like). The cardiac magnetic field that is one of the target magnetic fields to be measured by the magnetic field measuring apparatus 10 has no DC component. Accordingly, the magnetic field measuring apparatus 10 has no need to perform a calibration of a magnetic sensor to the DC offset of the magnetic sensor and the offset drift of a very low frequency (for example, 0.1 Hz or less), only performing the calibration of the magnetic sensor using the calibration magnetic field that is an alternating magnetic field.

Herein, generally, the environmental magnetic field is smaller at a higher frequency. For example, the environmental magnetic field is on the order of several tens of pT in bands higher than 50 Hz, which is at the same level as the peak of the cardiac magnetic field, which is one of the target magnetic fields to be measured by the magnetic field measuring apparatus 10 according to this embodiment. Accordingly, the calibration magnetic field generating unit 144 may generate an alternating magnetic field with a frequency higher than 50 Hz (frequency f0>50 Hz) as a calibration magnetic field. That is, since the signal frequency of the cardiac magnetic field is mostly lower than 20 Hz, the frequency of the alternating magnetic field as a calibration magnetic field may be higher than the frequency band of the target magnetic field to be measured.

Also in general, for example, 50 Hz or 60 Hz is used as the frequency of a commercial power supply. Therefore, there is a power supply noise at multiples of the frequency of these commercial power supplies. Accordingly, it is preferred that the calibration magnetic field generating unit 144 uses a frequency higher than the frequency of the target magnetic field to be measured, but avoiding a frequency that is a multiple of the frequency of the commercial power supply, as the frequency of the alternating magnetic field. As one example, it is preferred that the calibration magnetic field generating unit 144 uses a frequency higher than 50 Hz, but avoiding a frequency of an integer multiple of 50 Hz or 60 Hz. In this way, since the environmental magnetic field can be suppressed to the order of several tens of pT, the calibration magnetic field generating unit 144 only needs to generate a calibration magnetic field weak enough to neglect the environmental noise, for example, approximately several tens of nT. That is, by using such a frequency as the frequency of the alternating magnetic field, the magnetic field measuring apparatus 10 does not need to generate a strong magnetic field as the calibration magnetic field.

The calibration magnetic field generating unit 144 may have a plurality of calibration coils that generates a calibration magnetic field respectively. Then, the calibration magnetic field generating unit 144 may receive an alternating current corresponding to the frequency of the clock signal for a calibration, which is described below, and apply the alternating current corresponding to the frequency of the said clock signal to each of the plurality of calibration coils to generate an alternating magnetic field corresponding to the frequency of the clock signal from each of the plurality of calibration coils. For example, the calibration magnetic field generating unit 144 may have at least three or more calibration coils that each generates a calibration magnetic field in a different axial direction. Then, these different axial directions may be axial directions orthogonal to each other. As one example, the calibration magnetic field generating unit 144 may have a plurality of three-axis calibration coils that generate a calibration magnetic field in the three axial directions (for example, x, y, and z axis directions) that are respectively orthogonal to each other. This allows the magnetic field measuring apparatus 10 to calibrate the magnetic sensor using the plurality of calibration magnetic fields, each of which generates a primary independent three-axis magnetic field from a different position, thereby improving the accuracy of the calibration.

Also, when performing a calibration using such an alternating magnetic field, it is necessary to suppress the generation of an eddy current. Therefore, a housing of the calibration coil for generating the calibration magnetic field may be formed of a resin material or the like with a low electrical conductivity.

The information processing unit 150 is a component for processing data measured by the main unit 100 and outputting the processed data by displaying, printing and so on. The information processing unit 150 may be a computer such as a PC (personal computer), a tablet computer, a smartphone, a workstation, a server computer, or a general-purpose computer, or may be a computer system in which a plurality of computers are connected. Alternatively, the information processing unit 150 may be a dedicated computer designed for information processing in magnetic field measurement, or may be a dedicated hardware realized by a dedicated circuitry.

Figure 2:
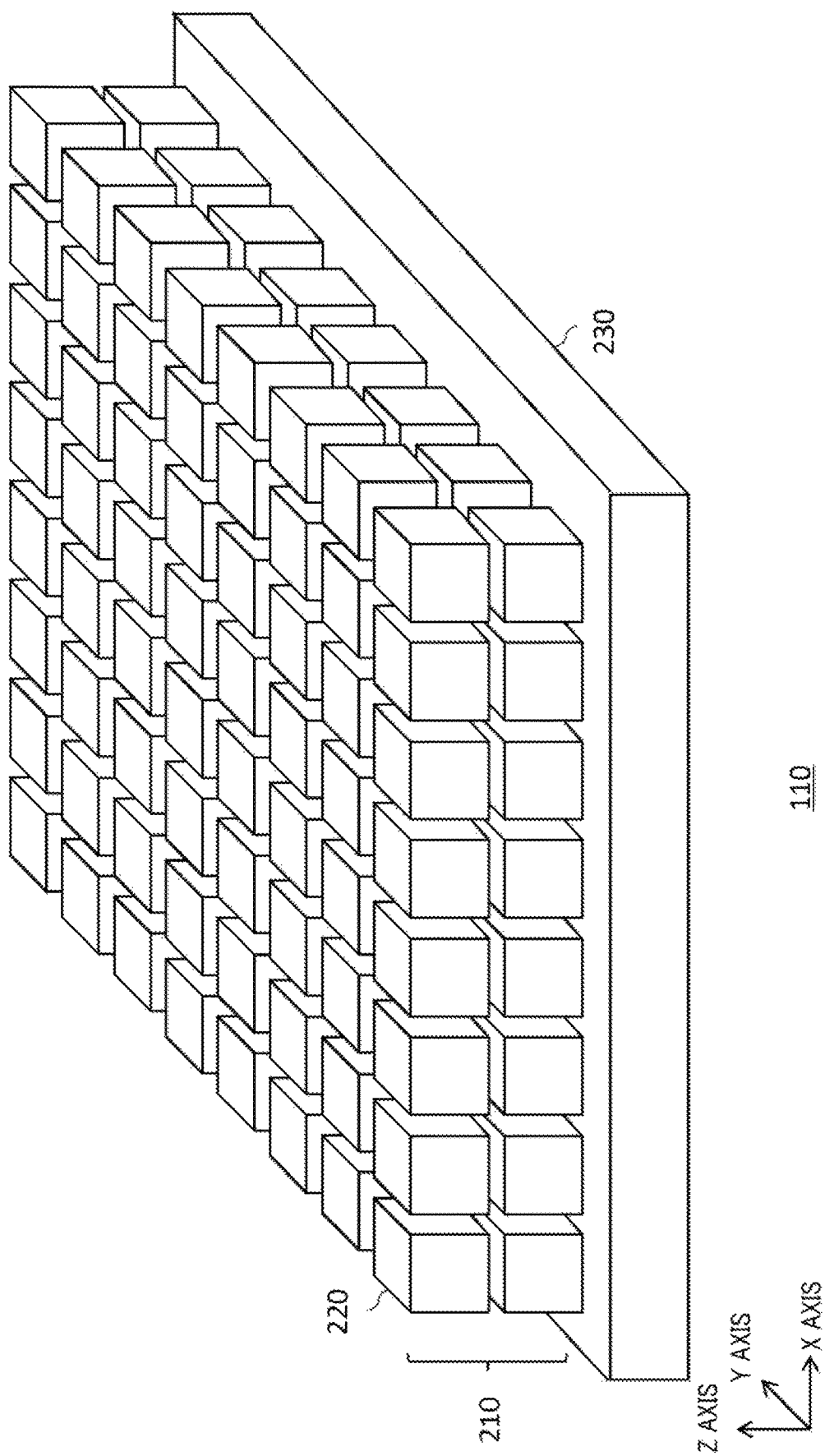
FIG. 2 illustrates a configuration of a magnetic sensor unit 110 according to this embodiment.

FIG. 2 illustrates a configuration of the magnetic sensor unit 110 according to this embodiment. The magnetic sensor unit 110 has a magnetic sensor array 210 and a sensor data gathering unit 230. The magnetic sensor array 210 has a plurality of magnetic sensor cells 220, and is capable of detecting the input magnetic field of the three axial directions. This figure illustrates the case where a plurality of magnetic sensor cells 220 are arranged in each of the X direction, the Y direction and the Z direction in the magnetic sensor array 210 (for example, 8 in the X direction, 8 in the Y direction, and 2 in the Z direction, total 128 magnetic sensor cells 220).

The sensor data gathering unit 230 is electrically connected to the plurality of magnetic sensor cells 220 included in the magnetic sensor array 210 (not illustrated in the figures), gathers sensor data (detection signals) from the plurality of magnetic sensor cells 220, and supplies the sensor data to the information processing unit 150.

Figure 3:
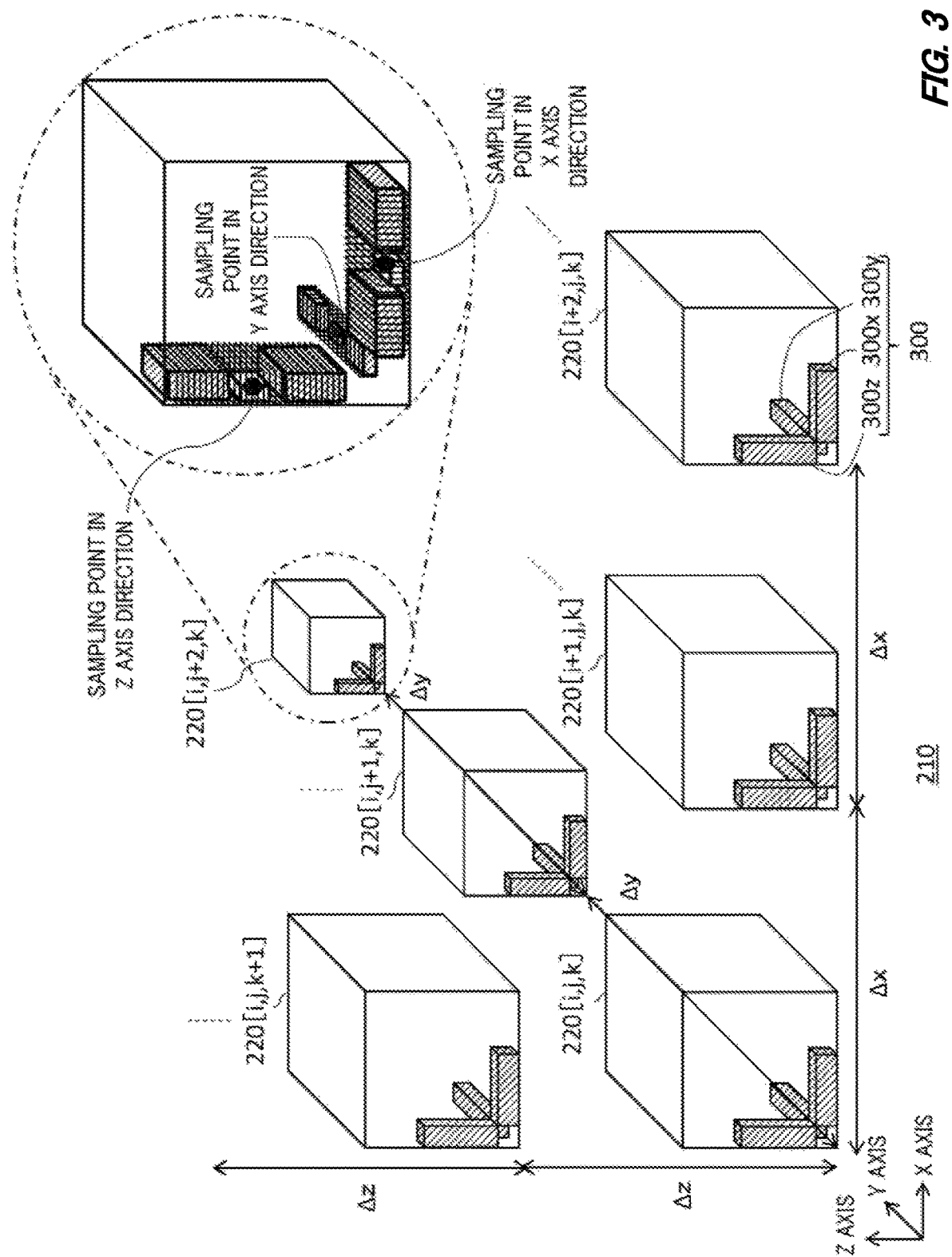
FIG. 3 illustrates a configuration of a magnetic sensor cell 220 in a magnetic sensor array 210 according to this embodiment.

FIG. 3 illustrates a configuration of the magnetic sensor cell 220 in the magnetic sensor array 210 according to this embodiment. Each of the plurality of magnetic sensor cells 220 has at least one sensor unit 300 with a magnetoresistive element respectively. In this figure, a case where each of the plurality of magnetic sensor cells 220 has three sensor units 300 $x\sim z$ (collectively referred to as "sensor unit 300"), and the input magnetic field can be detected in the three axial directions is shown as one example. However, any of the plurality of magnetic sensor cells 220 is not limited to having three sensor units 300 $x\sim z$, and it is only necessary for at least a part of the magnetic sensor array 210 to be capable of detecting the input magnetic field in the three axial directions. In this case, as described below, when performing the spatial-sampling on each spherical harmonic functions by the magnetic sensor array 210, it is necessary to detect the dependency on the spatial frequency related to the angular momentum in the magnetic field. Therefore, it is preferred that the arrangement position of each sensor unit 300 in the magnetic sensor array 210 is arranged as evenly as possible, at least in the azimuthal direction and zenithal direction. For the same reason, it is preferred that the magnetosensitive axes of each sensor in the magnetic sensor array 210 are also arranged as evenly as possible, at least in the azimuthal direction and zenithal direction. The sensor unit 300$x$ is arranged along the X axis direction and is capable of detecting a magnetic field in the X axis direction. Also, the sensor unit 300$y$ is arranged along the Y axis direction and is capable of detecting a magnetic field in the Y axis direction. Also, the sensor unit 300$z$ is arranged along the Z axis direction and is capable of detecting a magnetic field in the Z axis direction. As illustrated in an enlarged view shown in a dash-dot line part of this figure, in this embodiment, each of the sensor units 300 has the magnetic flux concentrators arranged on both ends of the magnetoresistive element. Accordingly, each sensor unit 300 uses the magnetoresistive element arranged in a narrow position sandwiched between the magnetic flux concentrators to perform the sampling on the magnetic field spatial distribution, so that spatial sampling points can be clarified in each axial direction. The details of the configuration of each sensor unit 300 are described below.

The plurality of magnetic sensor cells 220 are arranged at regular intervals of $\Delta x$, $\Delta y$, and $\Delta z$, respectively along the X axis direction, the Y axis direction, and the Z axis direction. The position of each magnetic sensor cell 220 in the magnetic sensor array 210 is expressed by a set [i,j,k] of a position i in the X direction, a position j in the Y direction, and a position k in the Z direction. Herein, i is an integer that satisfies $1 \leq i \leq Nx$ (Nx indicates the number of magnetic sensor cells 220 arranged in the X direction), j is an integer that satisfies $1 \leq j \leq Ny$ (Ny indicates the number of magnetic sensor cells 220 arranged in the Y direction), and k is an integer that satisfies $1 \leq k \leq Nz$ (Nz indicates the number of magnetic sensor cells 220 arranged in the Z direction). The above description has shown, as one example, the case where a plurality of magnetic sensor cells 220 are arrayed at regular intervals along each axial direction. However, it is not limited to this. The plurality of magnetic sensor cells 220 may also be arrayed with different intervals respectively in at least any one of the X, Y, and Z axis directions, for example.

In this figure, the three axial directions of the magnetic field detected by the sensor units 300$x$, 300$y$, and 300$z$ are the same direction as the three dimensional directions in which the magnetic sensor cells 220 are arrayed. In this way, it is easy to understand each component of the distribution of the measured magnetic field. However, the three axial directions in which the magnetic field is detected may also be different from the three dimensional directions in which the magnetic sensor cells 220 are arrayed. For example, instead of the X axis, Y axis, and Z axis functioning as the three axial directions in which the magnetic field is detected, the r axis, $\theta$ axis, and $\varphi$ axis of the polar coordinate system may also be used. Furthermore, instead of the X axis, Y axis, and Z axis, the r axis, $\theta$ axis, and $\varphi$ axis of the polar coordinate system may also be used as the three dimensional directions in which the magnetic sensor cells 220 are arrayed. In a case where the three axial directions in which the magnetic field is detected are different from the three dimensional directions in which the magnetic sensor cells 220 are arrayed, there is no restriction on the arrangement of the sensor units 300 in the magnetic sensor cells 220 or the array direction of the magnetic sensor cells 220, and it is possible to increase degrees of freedom in design of the magnetic sensor array 210. In this case, the magnetic sensor cell 220 can be configured to be small, thus the magnetic sensor array 210 having such a plurality of magnetic sensor cells 220 is possible to be miniaturized.

Figure 4:
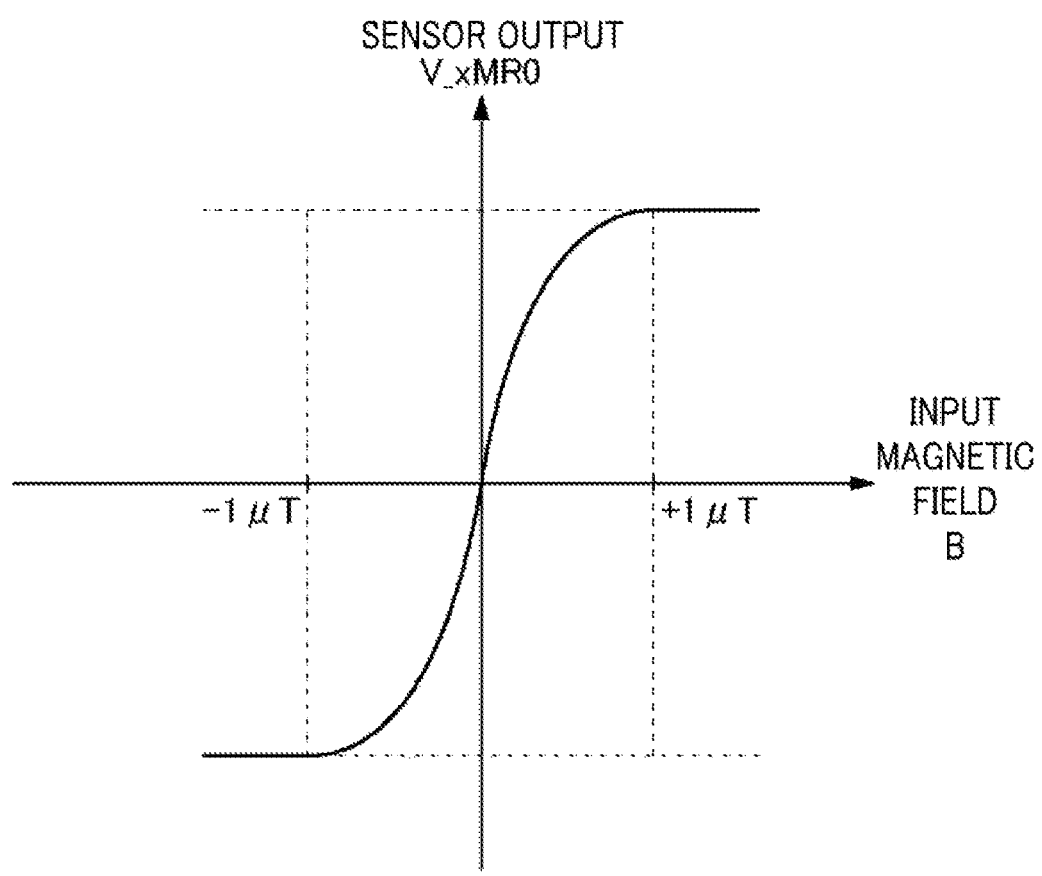
FIG. 4 illustrates one example of an input/output characteristic of a magnetic sensor having a magnetoresistive element according to this embodiment.

FIG. 4 illustrates one example of an input/output characteristic of the magnetic sensor having a magnetoresistive element according to this embodiment. In this figure, the horizontal axis illustrates the magnitude B of the input magnetic field input to the magnetic sensor, and the vertical axis illustrates the magnitude V_xMR0 of the detection signal of the magnetic sensor. For example, the magnetic sensor includes a Giant Magneto-Resistance (GMR) element, a Tunnel Magneto-Resistance (TMR) element or the like, and detects the magnitude of the magnetic field in one predetermined axial direction.

Such a magnetic sensor has high magnetic sensitivity, which is the slope of the detection signal V_xMR0 with respect to the input magnetic field B, and can detect a very small magnetic field of approximately 10 pT. On the other hand, the detection signal V_xMR0 becomes saturated when the absolute value of an input magnetic field B is approximately 1 µT, for example, thus the magnetic sensor has a narrow range in which the linearity of the input/output characteristic is good. Therefore, when a closed loop is added to such a magnetic sensor, which generates a feedback magnetic field, it is possible to improve the linearity of the magnetic sensor. The following describes such a magnetic sensor.

Figure 5:
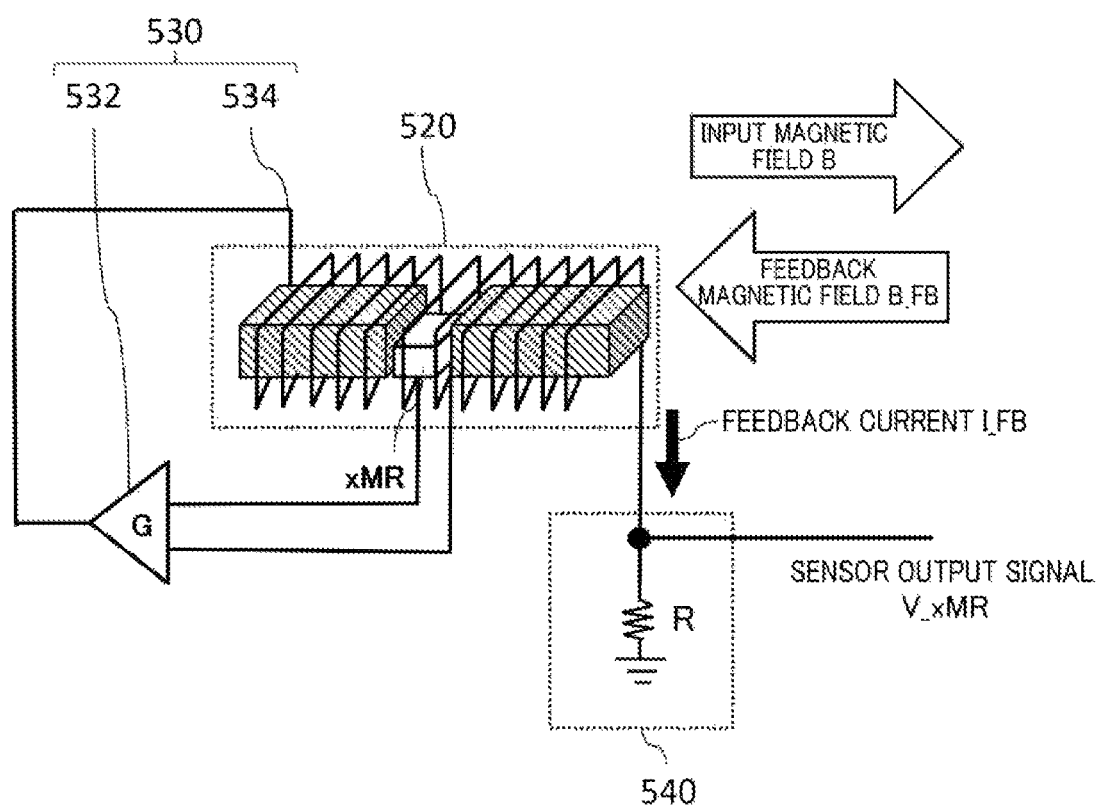
FIG. 5 illustrates a configuration example of a sensor unit 300 according to this embodiment.

FIG. 5 illustrates an example of a configuration of a sensor unit 300 according to this embodiment. The sensor unit 300 is provided inside each of the plurality of magnetic sensor cells 220, including a magnetic sensor 520, a magnetic field generating unit 530, and an output unit 540. A part of the sensor unit 300, for example, an amplifier circuit 532 and so on may also be provided on the side of the sensor data gathering unit 230 rather than the side of the magnetic sensor cell 220.

The magnetic sensor 520 includes a magnetoresistive element such as a GMR element or a TMR element, similar to the magnetic sensor described in FIG. 4. Also, each magnetic sensor 520 includes the magnetoresistive element and two magnetic flux concentrators arranged on both ends of the magnetoresistive element, and the magnetoresistive element is arranged in the position that is sandwiched by the two magnetic flux concentrators. When a positive direction of the magnetosensitive axis is defined as the +X direction, the magnetoresistive element included in the magnetic sensor 520 may be formed so that a resistance value increases in response to an input of a magnetic field in the +X direction and the resistance value decreases in response to an input of a magnetic field in the −X direction. That is, observing a change in the resistance value of the magnetoresistive element included in the magnetic sensor 520 can detect the magnitude of the magnetic field B input to the magnetic sensor 520. For example, assuming the magnetic sensitivity of the magnetic sensor 520 is S, the detection result of the magnetic sensor 520 for the input magnetic field B can be calculated as S×B. The magnetic sensor 520 is, as one example, connected to a power supply or the like, and outputs a voltage drop corresponding to the change of the resistance value, as a detection result of the input magnetic field. The details of the configuration of the magnetic sensor 520 are described below.

The magnetic field generating unit 530 generates a feedback magnetic field that reduces the input magnetic field detected by the magnetic sensor 520 and that has a magnitude corresponding to the output signal output by the output unit 540, and provides this feedback magnetic field to the magnetic sensor 520. For example, the magnetic field generating unit 530 operates to cause the generation of a feedback magnetic field B_FB having an orientation that is the opposite of the orientation of the magnetic field B input to the magnetic sensor 520 and an absolute value that is substantially the same as that of the input magnetic field, to cancel out the input magnetic field. The magnetic field generating unit 530 includes an amplifier circuit 532 and a feedback coil 534.

The amplifier circuit 532 outputs, as a feedback current I_FB, a current corresponding to the detection result of the input magnetic field of the magnetic sensor 520. When the magnetoresistive element included in the magnetic sensor 520 is composed of a bridge circuit including at least one magnetoresistive element, an output of the bridge circuit is connected to each of a pair of input terminals of the amplifier circuit 532. Then, the amplifier circuit 532 outputs a current corresponding to the output of the bridge circuit, as the feedback current I_FB. The amplifier circuit 532 includes a transconductance amplifier, for example, and outputs the feedback current I_FB corresponding to the output voltage of the magnetic sensor 520. For example, assuming a voltage-current conversion coefficient of the amplifier circuit 532 is G, the feedback current I_FB can be calculated as G×S×B.

The feedback coil 534 generates the feedback magnetic field B_FB corresponding to the feedback current I_FB. The feedback coil 534 is wound along the axial direction of the magnetic field that is targeted for detection by the magnetic sensor 520 so as to enclose the magnetoresistive element and the two magnetic flux concentrators arranged at both ends of the magnetoresistive element included by the magnetic sensor 520. The feedback coil 534 preferably generates a feedback magnetic field B_FB that is uniform across the entire magnetic sensor 520. For example, assuming the coil factor of the feedback coil 534 is β, the feedback magnetic field B_FB can be calculated as β×I_FB. Herein, the feedback magnetic field B_FB is generated with an orientation that cancels out the input magnetic field B, thus the magnetic field input to the magnetic sensor 520 is reduced to B-B_FB. Accordingly, the feedback current I_FB is indicated by the expression below.

$$I\_FB = G \times S \times (\beta - \beta \times I\_FB) \quad \text{[Expression 1]}$$

When Expression 1 is solved for the feedback current I_FB, it is possible to calculate the value of the feedback current I_FB in a steady state of the sensor unit 300. The expression below is calculated from Expression 1, assuming that the magnetic sensitivity S of the magnetic sensor 520 and the voltage-current conversion coefficient G of the amplifier circuit 532 are sufficiently large.

$$I\_FB = \frac{G \times S \times B}{1 + G \times S \times \beta} \cong \frac{B}{\beta} \quad \text{[Expression 2]}$$

The output unit 540 outputs an output signal V_xMR corresponding to the feedback current I_FB that is to flow in order for the magnetic field generating unit 530 to generate the feedback magnetic field B_FB. For example, the output unit 540 includes a resistance element with a resistance value R, and outputs a voltage drop, caused by the feedback current I_FB flowing through this resistance element, as the output signal V_xMR. In this case, the output signal V_xMR is calculated from Expression 2 as indicated in the expression below.

$$V\_xMR = R \times I\_FB = \frac{R \times B}{\beta} \quad \text{[Expression 3]}$$

As described above, the sensor unit 300 generates the feedback magnetic field that reduces the magnetic field input thereto from the outside, thus the magnetic field substantially input to the magnetic sensor 520 is reduced. This allows the sensor unit 300 to prevent the detection signal V_xMR from saturating even when the absolute value of the input magnetic field B exceeds 1 µT, for example, under the condition of using a magnetoresistive element with nonlinearity and narrow operating magnetic field range characteristics shown in FIG. 4 as the magnetic sensor 520. The input/output characteristic of such a sensor unit 300 is described in the followings.

Figure 6:
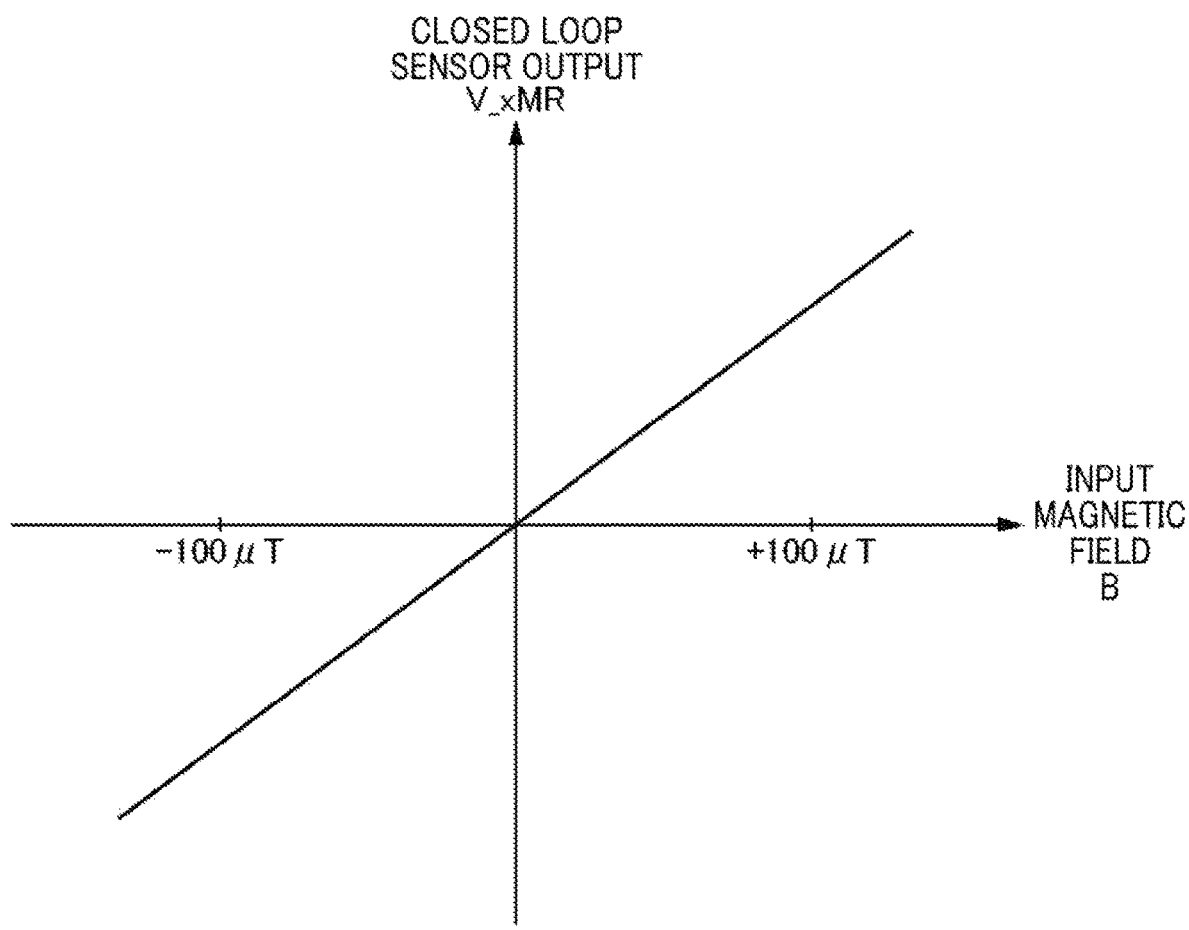
FIG. 6 illustrates one example of an input/output characteristic of the sensor unit 300 according to this embodiment.

FIG. 6 illustrates one example of an input/output characteristic of the sensor unit 300 according to this embodiment. In this figure, the horizontal axis indicates the magnitude B of the input magnetic field input to the sensor unit 300, and the vertical axis indicates the magnitude V_xMR of the detection signal of the sensor unit 300. The sensor unit 300 has high magnetic sensitivity and can detect a very small magnetic field of approximately 10 pT. Furthermore, even when the absolute value of the input magnetic field B exceeds 100 µT, for example, the sensor unit 300 can maintain good linearity for the detection signal V_xMR.

That is, the sensor unit 300 according to this embodiment is configured such that the detection result for the input magnetic field B has linearity in a predetermined range of the input magnetic field B where the absolute value of the input magnetic field B is less than or equal to several hundred pT for example. By using such a sensor unit 300, it is possible to easily detect very weak magnetic signals, such as cardiac magnetic field signals.

Figure 7:
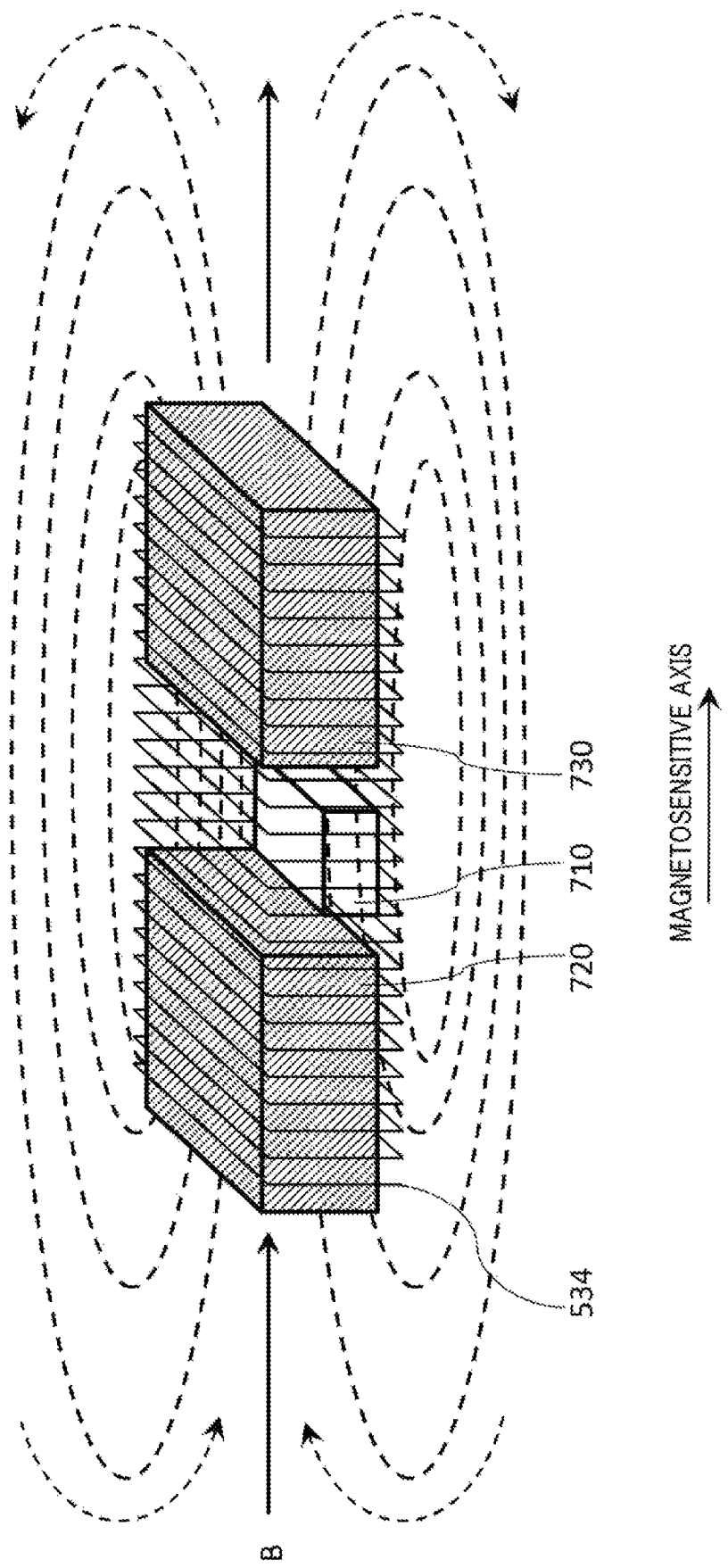
FIG. 7 illustrates a configuration example of a magnetic sensor 520 according to this embodiment.

FIG. 7 illustrates an example of a configuration of a magnetic sensor 520 according to this embodiment. In this figure, the magnetic sensor 520 includes a magnetoresistive element 710, magnetic flux concentrators 720 and 730 arranged on both ends of the magnetoresistive element 710. The magnetic flux concentrators 720 and 730 are arranged on both ends of the magnetoresistive element 710 so as to sandwich the magnetoresistive element 710 in between. In this figure, the magnetic flux concentrator 720 is provided on the negative side of the magnetoresistive element 710 along the magnetosensitive axis, and the magnetic flux concentrator 730 is provided on the positive side of the magnetoresistive element 710 along the magnetosensitive axis. The magnetosensitive axis may be along the fixed magnetization direction in a magnetization fixing layer that forms the magnetoresistive element 710. Also, when the magnetic field is input from the negative side to the positive side of the magnetosensitive axis, the resistance of the magnetoresistive element 710 may be increased or decreased. The magnetic flux concentrators 720 and 730 are formed of a material with high magnetic permeability, for example, permalloy and so on. Then, when the magnetic sensor 520 is configured as indicated in this figure, the feedback coil 534 is wound along the axial direction of the magnetic field that is targeted for detection by the magnetic sensor 520, so as to enclose the cross sections of the magnetoresistive element 710, the magnetic flux concentrators 720 and 730 arranged on both ends of the magnetoresistive element 710. When having a plurality of magnetoresistive elements 710 inside one magnetic sensor 520, the magnetic sensor 520 may also have a plurality of sets including a magnetoresistive element and magnetic flux concentrators arranged on the both ends thereof. In this case, the feedback coil 534 may be wound so that the sets including a magnetoresistive element and magnetic flux concentrators arranged on the both ends thereof are enclosed in one coil.

In such a magnetic sensor 520, when a magnetic field is input from the negative side to the positive side of the magnetosensitive axis, the magnetic flux concentrators 720 and 730 formed of the material with high magnetic permeability are magnetized, thereby generating a magnetic flux distribution such as shown by the dashed line in this figure. Subsequently, the magnetic fluxes generated by the magnetization of the magnetic flux concentrators 720 and 730 pass through the position of the magnetoresistive element 710 that is sandwiched between the two magnetic flux concentrators 720 and 730. Therefore, the magnetic flux density in the position of the magnetoresistive element 710 can be significantly increased by arranging the magnetic flux concentrators 720 and 730. Also, as shown in this figure, by sampling the magnetic field spatial distribution using the magnetoresistive element 710 that is arranged in the narrow position sandwiched between the magnetic flux concentrators 720 and 730, the spatial sampling points can be clarified.

Figure 8:
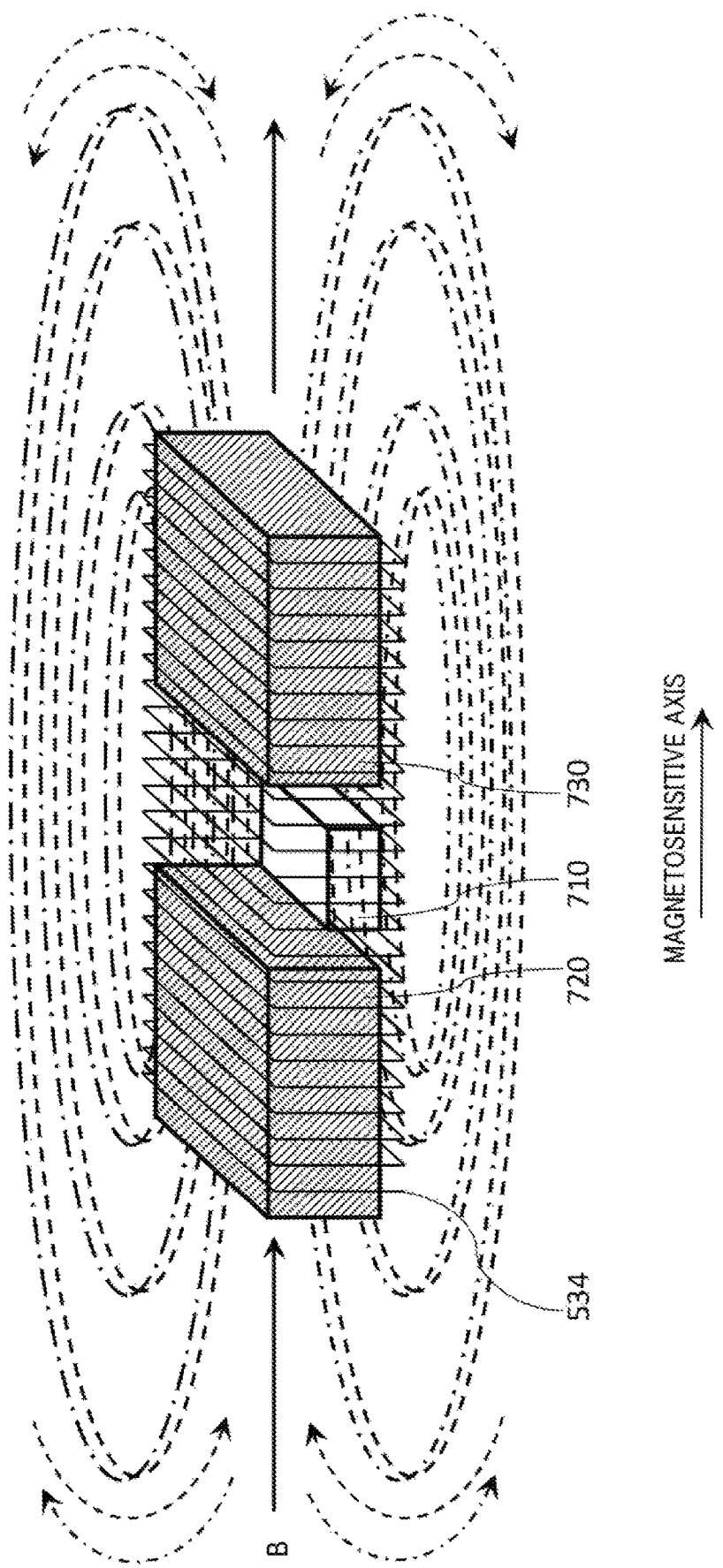
FIG. 8 illustrates a magnetic flux distribution in generating a feedback magnetic field in the magnetic sensor 520 according to this embodiment.

FIG. 8 illustrates a magnetic flux distribution when the feedback magnetic field has been generated at the magnetic sensor 520 according to this embodiment. In FIG. 8, members having the same function and configuration as in FIG. 7 are given the same reference numerals, and the following describes only differing points. In the magnetic sensor 520 according to this embodiment, when a feedback current is supplied to the feedback coil 534, the feedback coil 534 generates a feedback magnetic field, thereby generating the magnetic flux distribution as indicated by a dash-dot line in this figure. The magnetic flux generated by this feedback magnetic field distributes spatially so as to cancel out the spatial distribution of the magnetic field input to the magnetoresistive element 710 and magnetically amplified by the magnetic flux concentrators 720 and 730. Therefore, in the magnetic sensor 520, when the magnetic flux concentrators 720 and 730 are arranged on the both ends of the magnetoresistive element 710 as indicated in this figure, the magnetic distribution in the position of the magnetoresistive element 710 can be accurately canceled out by the feedback magnetic field, thus a sensor with a high linearity between the input magnetic field and the output voltage can be realized.

Figure 9:
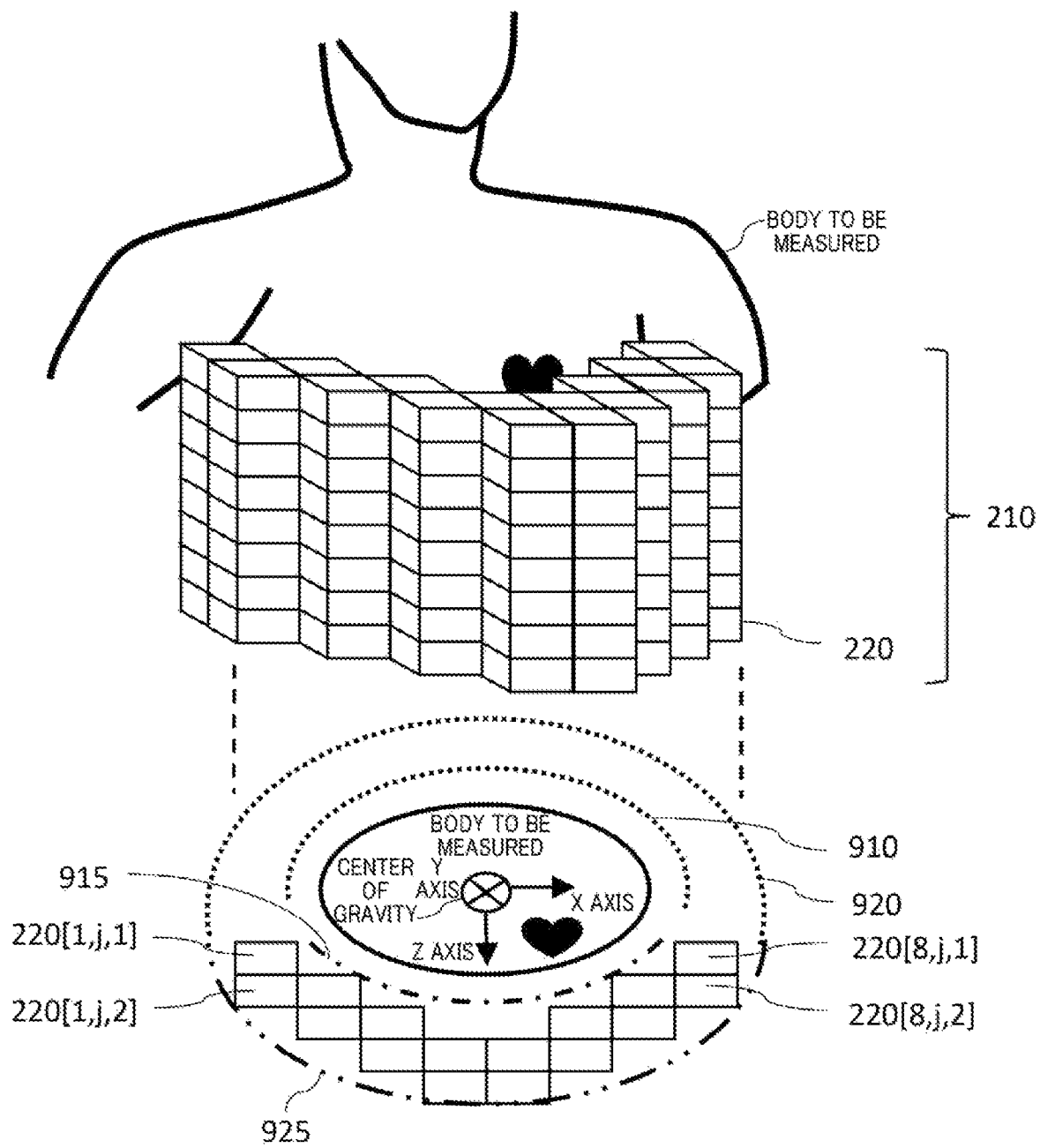
FIG. 9 illustrates an exemplary arrangement of a plurality of magnetic sensor cells 220 in the magnetic sensor array 210 according to this embodiment.

FIG. 9 illustrates an exemplary arrangement of a plurality of magnetic sensor cells 220 in the magnetic sensor array 210 according to this embodiment. In FIG. 2 and FIG. 3, the magnetic sensor array 210 has been indicated as a plane shape for convenience of the description. However in actual, the magnetic sensor array 210, as indicate in this figure, may have a curved surface shape curving toward at least one direction. Further, the magnetic sensor array 210 may be configured so that the plurality of magnetic sensor cells 220 is three-dimensionally arranged at grid points included in the said curved surface shape. As one example, the magnetic sensor array 210 may be configured with the plurality of magnetic sensor cells 220 three-dimensionally arrayed in an arc shape in a cross-sectional view.

That is, the plurality of magnetic sensor cells 220 may be arrayed in an arc shape in cross-sectional view along the chest of the body to be measured, with the center of gravity of the body to be measured at the center. In this case, each magnetic sensor cell 220 is arranged at the respective grid points included in the curved surface shape in the three-dimensional grid space. The grid points are respective points provided at predetermined regular intervals provided along the X direction, the Y direction, and the Z direction to form a lattice form. As one example, each magnetic sensor cell 220 is arranged along a curved surface protruding in a direction orthogonal to one direction, when viewed in any one direction of the X direction, the Y direction, and the Z direction. This figure illustrates an example where each magnetic sensor cell 220 is arranged along a curved surface protruding in a positive direction of the Z axis when viewed in the Y direction. Then, the magnetic sensor array 210 may form a curved surface shape protruding in the positive direction of the Z axis by, for example, arranging each magnetic sensor cell 220 at each grid point in the three-dimensional grid space so that each vertex of each magnetic sensor cell 220 is arranged in the negative direction of the Z axis as far as possible in a range not exceeding the predetermined curved surface protruding in the positive direction of the Z axis.

In more detail, in the cross-sectional view of this figure, the inner (negative side of the z axis) plurality of magnetic sensor cells 220, that is, magnetic sensor cells 220[1,j,1] to 220[8,j,1], are arranged outside the arc indicated by the dash-dot line of sign 915 so that they are arranged outside the inscribed circle of magnetic sensor array 210 indicated by sign 910. Also, the outer (positive side of the Z axis) plurality of magnetic sensor cells 220, that is, magnetic sensor cells 220[1,j,2] to 220[8,j,2], are arranged inside the arc indicated by the double-dot line of sign 925 so that they are arranged inside the circumscribed circle of magnetic sensor array 210 indicated by sign 920. The centers of these inscribed and circumscribed circles are common and match the coordinate origin in the signal separating calculation described below.

This enables the magnetic sensor array 210 to have sensor units arranged in multiple directions rather than just in one direction facing the heart, and to sense the cardiac magnetic field from multiple directions. Also, regarding the magnetic sensor array 210 according to this embodiment, the shape of the magnetic sensor array 210 can be easily changed because the magnetic sensor cells 220 are formed in a cuboid shape as one example. That is, the magnetic sensor array 210 according to this embodiment can utilize various configurable shapes with the magnetic sensor cells 220 arranged at grid points, and thus feature a high degree of freedom in design. Accordingly, the magnetic sensor array 210 can easily form a curved surface shape in a three dimensional space, with the plurality of magnetic sensor cells 220 arranged at the grid points included in the curved surface shape in the three dimensional space as illustrated in this figure. Then, the magnetic field measuring apparatus 10 measures the magnetic field by arranging the magnetic sensor array 210 so that the chest of the body to be measured is located at the center side of the curved surface, that is, the heart, which is the source of the target magnetic field to be measured, is located at the center side of the curved surface. This enables the magnetic field measuring apparatus 10 to separate the target magnetic field to be measured from the disturbance magnetic field with high accuracy by performing signal space separation (described below) using the measurement data measured at a position close to the heart, which is the source of the target magnetic field to be measured. In this case, the magnetic sensor array 210 is preferable to have the curvature of the curved surface approximately equivalent to the curvature around the chest of the body to be measured, which can measure the magnetic field at a position closer to the heart, which is the source of the target magnetic field to be measured.

Figure 10:
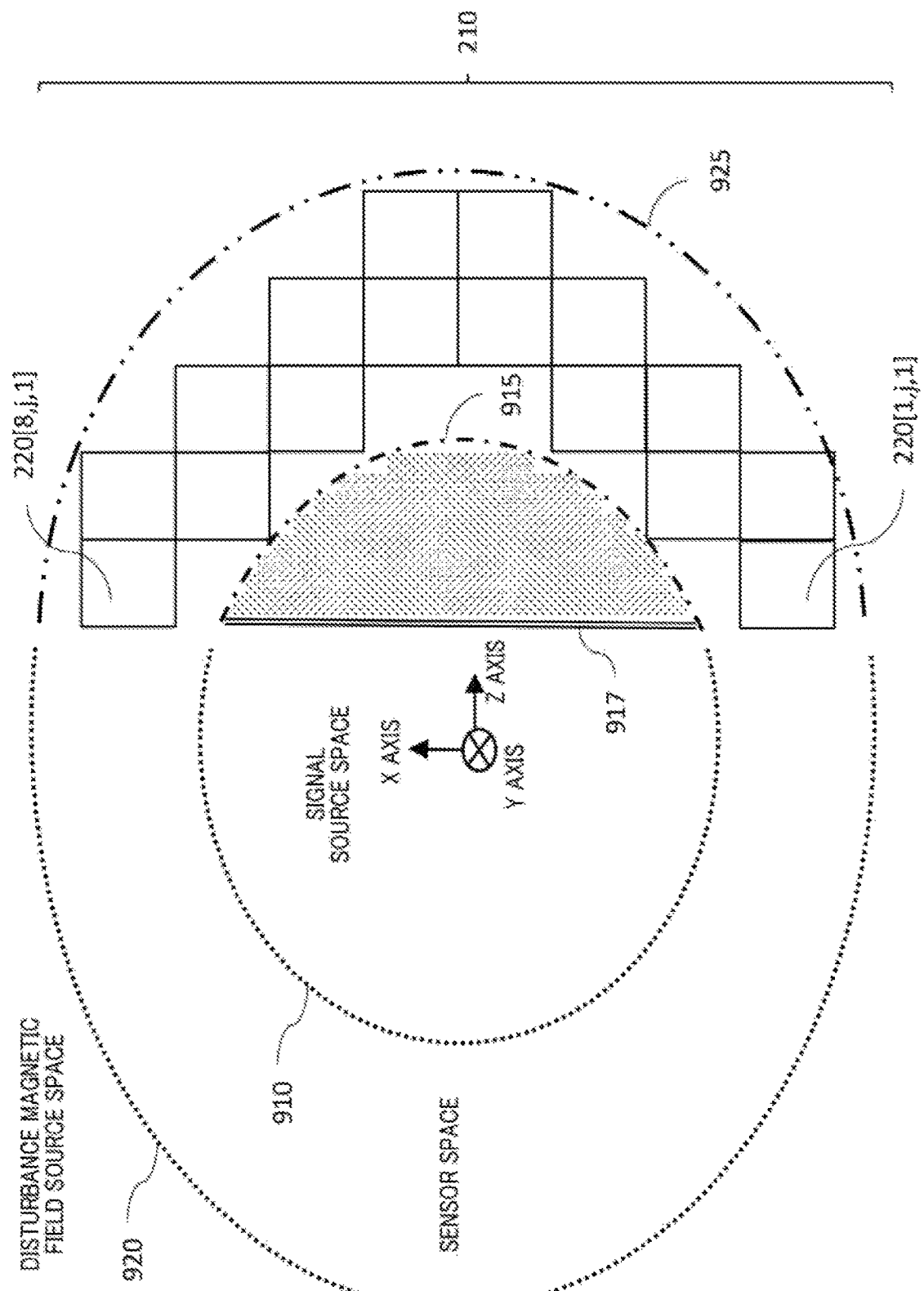
FIG. 10 illustrates a preferred arrangement position of a calibration magnetic field generating unit 144 during calibration.

FIG. 10 illustrates a preferred arrangement position of the calibration magnetic field generating unit 144 during a calibration. The magnetic field measuring apparatus 10, as described above, causes the magnetic sensor unit 110 to face the calibration magnetic field generating unit 144 when performing a calibration. In this case, the calibration magnetic field generating unit 144 is arranged on the side facing the body to be measured when viewed from the magnetic sensor array 210. That is, the calibration magnetic field generating unit 144 is arranged more inwardly (on the negative side of the Z axis) than the plurality of magnetic sensor cells 220 [1,j,1] to 220 [8,j,1] of the inside (on the negative side of the z axis) of the magnetic sensor array 210.

Herein, the outside of the circle circumscribed to the magnetic sensor array 210 and indicated by the sign 920, is the disturbance magnetic field source space. Also, the space between the inside of the circle circumscribed to the magnetic sensor array 210 indicated by the sign 920, and the outside of the circle inscribed to the magnetic sensor array 210 indicated by the sign 910, is the sensor space. Also, the inside of the circle inscribed to the magnetic sensor array 210 indicated by the sign 910 is the signal source space.

The magnetic field measuring apparatus 10 is preferred to arrange the calibration magnetic field generating unit 144 in the signal source space when performing a calibration. In particular, the calibration magnetic field generating unit 144 may be arranged inside the region enclosed by the arc 915 and the string 917 connecting the both end points of the arc 915. In this way, the calibration magnetic field generating unit 144 may be arranged in the region indicated by dots in this figure. Also in this case, the calibration magnetic field generating unit 144 may also be arranged adjacent to the inner plurality of magnetic sensor cells 220 [1,j,1] to 220 [8,j,1] that form the circular arc 915. By arranging the calibration magnetic field generating unit 144 in such a position, the magnetic field measuring apparatus 10 can calibrate the magnetic sensor 520 neglecting influence due to the disturbance magnetic field even in the environmental magnetic field, since a relatively stronger calibration magnetic field can be supplied to the magnetic sensor 520 by the signal source space when performing a calibration.

Figure 11:
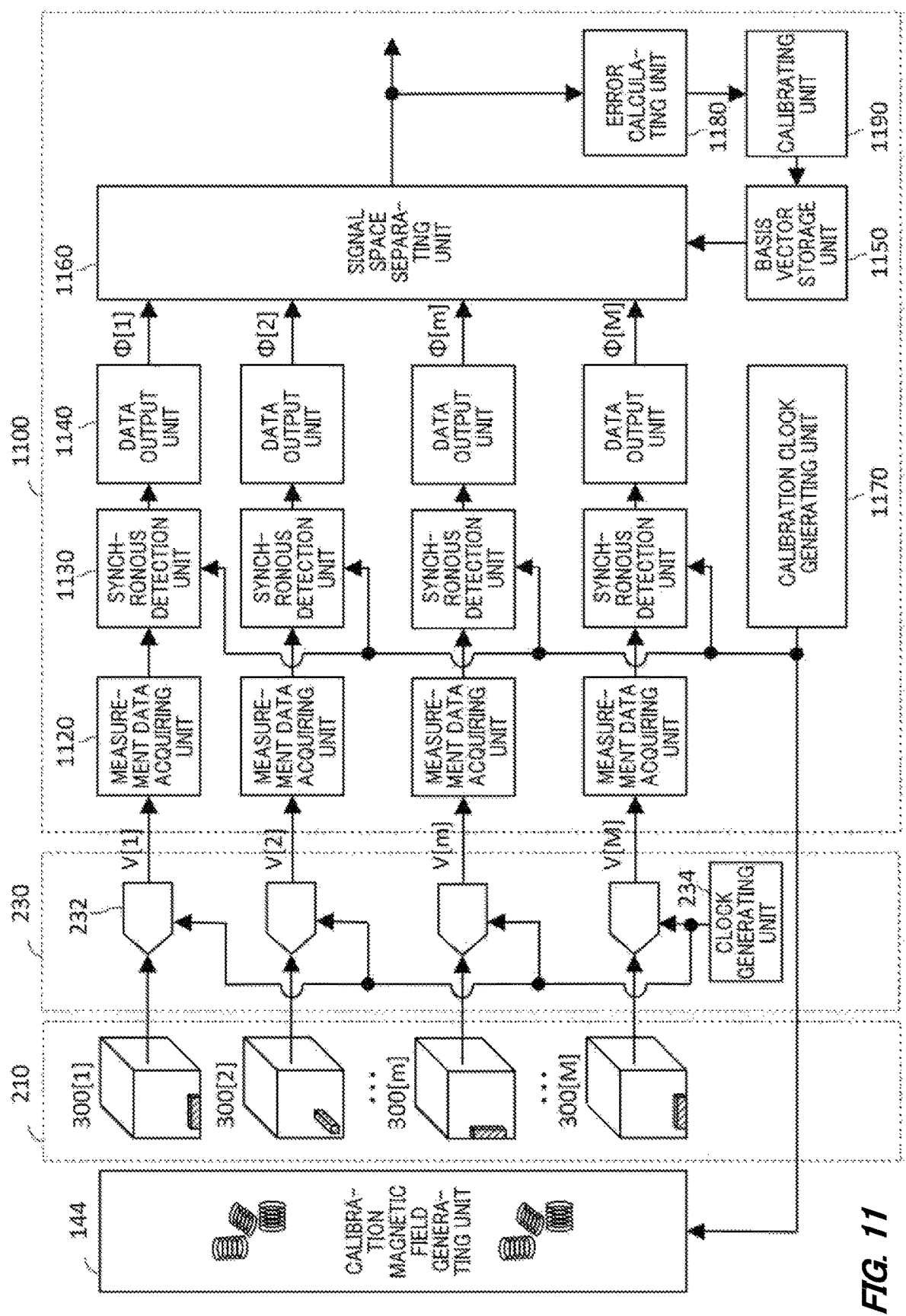
FIG. 11 illustrates a configuration of the calibration magnetic field generating unit 144, the magnetic sensor array 210, a sensor data gathering unit 230 and a sensor data processing unit 1100 according to this embodiment.

FIG. 11 illustrates a configuration of the calibration magnetic field generating unit 144, the magnetic sensor array 210, a sensor data gathering unit 230 and a sensor data processing unit 1100 according to this embodiment.

When performing a calibration, the calibration magnetic field generating unit 144 is arranged on the side facing the body to be measured when viewed from the magnetic sensor array 210, preferably in the position indicated by dots in FIG. 10. The calibration magnetic field generating unit 144 may have a plurality of calibration coils that respectively generates a calibration magnetic field as described above. Then, the calibration magnetic field generating unit 144 receives an alternating current corresponding to the frequency of the clock signal for calibration, and applies the alternating current corresponding to the frequency of the said clock signal to each of the plurality of calibration coils to generate an alternating magnetic field corresponding to the frequency of the clock signal from each of the plurality of calibration coils.

The magnetic sensor array 210 is composed of a plurality of magnetic sensor cells 220, each of which has at least one sensor unit 300, and is capable of detecting input magnetic field in three axial directions as an entire magnetic sensor array 210. In this figure, the case where the magnetic sensor array 210 has M sensor units 300[1] to 300[M] is shown as one example.

The sensor data gathering unit 230 includes a plurality of AD converters 232 and a clock generating unit 234. The plurality of AD converters 232 are provided corresponding to the plurality of sensor units 300[1] to 300[M], respectively, and convert the analog detection signals (V_xMR in FIG. 6) output by the corresponding sensor units 300 into digital measurement data V[1] to V[M], respectively.

The clock generating unit 234 generates a sampling clock and supplies a common sampling clock to each of the plurality of AD converters 232. Then, each of the plurality of AD converters 232 performs AD conversion according to the common sampling clock supplied from the clock generating unit 234. Accordingly, all of the plurality of AD converters 232, which AD convert the outputs of the plurality of sensor units 300[1] to 300[M] provided in different positions, respectively, operate in synchronization. In this way, the plurality of AD converters 232 can simultaneously sample the detection results of the plurality of sensor units 300[1] to 300[M] provided in different spaces.

The sensor data processing unit 1100 includes a plurality of measurement data acquiring units 1120, a plurality of synchronous detection units 1130, a plurality of data output units 1140, which are provided corresponding to the plurality of sensor units 300[1] to 300[M] respectively, as well as a basis vector storage unit 1150, a signal space separating unit 1160, a calibration clock generating unit 1170, an error calculating unit 1180 and a calibrating unit 1190.

The measurement data acquiring unit 1120 is connected to each of the plurality of AD converters 232 that are connected to the corresponding sensor units 300, and acquires the measurement data V[1] to V[M] respectively measured by the plurality of sensor units 300[1] to 300[M] that the magnetic sensor array 210 includes. More specifically, the measurement data acquiring unit 1120 may be composed of using a flip-flop or the like to latch and acquire the digital measurement data V converted into digital form by the AD converter 232 at a predetermined timing T. The measurement data acquiring unit 1120 supplies the acquired measurement data V to the synchronous detection unit 1130.

When measuring the target magnetic field to be measured, the synchronous detection unit 1130 supplies the measurement data V supplied from the measurement data acquiring unit 1120 to the data output unit 1140 as it is. On the other hand, when performing a calibration, the synchronous detection unit 1130 detects the calibration magnetic field, which is an alternating magnetic field, using the signal of the frequency of the alternating magnetic field. As one example, the synchronous detection unit 1130 synchronously detects the calibration magnetic field according to the clock signal for calibration. Then, the synchronous detection unit 1130 extracts the frequency components synchronized with the calibration magnetic field, which is an alternating magnetic field, from among the measurement data V supplied from the measurement data acquiring unit 1120, and supplies the measurement data V according to the extracted frequency components to the data output unit 1140. Herein, such synchronous detection may be performed in software, or may be performed in hardware. Also, in the above description, the case where the synchronous detection unit 1130 extracts the frequency components synchronized with the calibration magnetic field by performing synchronous detection has been shown as one example, but the frequency components synchronized with the calibration magnetic field may also be extracted by frequency separation using FFT (bandpass filter to extract the frequency components synchronized with the calibration magnetic field) and so on.

The data output unit 1140 supplies, to the signal space separating unit 1160, a sensor array signal t including respective sensor signal components Φ[1] to Φ[M] equivalent to the measurement data V[1] to V[M] supplied from each of the plurality of synchronous detection units 1130.

The basis vector storage unit 1150 stores basis vectors necessary for the signal space separating unit 1160 to perform signal separation on the sensor array signal Φ, and supplies the basis vectors to the signal space separating unit 1160. Here, signal separation may be called signal space separation. The basis vector storage unit 1150 sequentially updates the stored basis vectors to the basis vectors that have been changed by the calibrating unit 1190. This will be described below.

The signal space separating unit 1160 performs signal-separation on the spatial distribution of the input magnetic field indicated by the measurement data V[1] to V[M] supplied as each component of the sensor array signal cl) from the data output unit 1140 using, as the basis vectors, the vector signal having the signal output by each of the plurality of magnetic sensors 520 as each signal component when the magnetic field with the spatial distribution of the orthonormal functions are detected by the magnetic sensor array 210. In this case, the signal space separating unit 1160 acquires the basis vectors necessary for the signal separation from the basis vector storage unit 1150. Then, the signal space separating unit 1160 uses the basis vectors acquired from the basis vector storage unit 1150 to perform signal separation on the spatial distribution of the magnetic field indicated by the measurement data V[1] to V[M] into the target magnetic field to be measured (signal source space signal) and the disturbance magnetic field (disturbance space signal), suppresses the disturbance magnetic field, calculates the target magnetic field to be measured, and outputs the calculated result. This will also be described below.

When performing a calibration, the calibration clock generating unit 1170 generates a clock signal for generating an alternating calibration magnetic field and an alternating current corresponding to the frequency of the clock signal. Then, the calibration clock generating unit 1170 supplies the alternating current corresponding to the frequency of the clock signal to the calibration magnetic field generating unit 144 while supplying the generated clock signal to the plurality of synchronous detection units 1130. In response to this, the calibration magnetic field generating unit 144 applies an alternating current corresponding to the frequency of the clock signal to each of the plurality of calibration coils, and generates an alternating magnetic field corresponding to the frequency of the clock signal from each of the plurality of calibration coils. Also, the plurality of synchronous detection units 1130 detect the alternating calibration magnetic field generated by the calibration magnetic field generating unit 144 according to the clock signal respectively. In the above description, the case where the calibration clock generating unit 1170 is provided inside the sensor data processing unit 1100 is shown as one example, but the calibration clock generating unit 1170 may also be configured, for example, inside the calibration magnetic field generating unit 144.

When performing a calibration, the error calculating unit 1180 calculates the separation error in the case where the signal space separating unit 1160 has performed the signal separation on the spatial distribution of the calibration magnetic field. Then, the error calculating unit 1180 supplies the calculated separation error to the calibrating unit 1190.

The calibrating unit 1190 calibrates the sensor error in the magnetic sensor 520 based on the separation error in a case of performing the signal separation on the spatial distribution of the calibration magnetic field. In this case, the calibrating unit 1190 calibrates the sensor error by changing the basis vectors used by the signal space separating unit 1160. Then, the calibrating unit 1190 supplies information related to the changed basis vectors to the basis vector storage unit 1150. In response to this, the basis vector storage unit 1150 updates the stored basis vectors. This will be described in detail using expressions.

Figure 12:
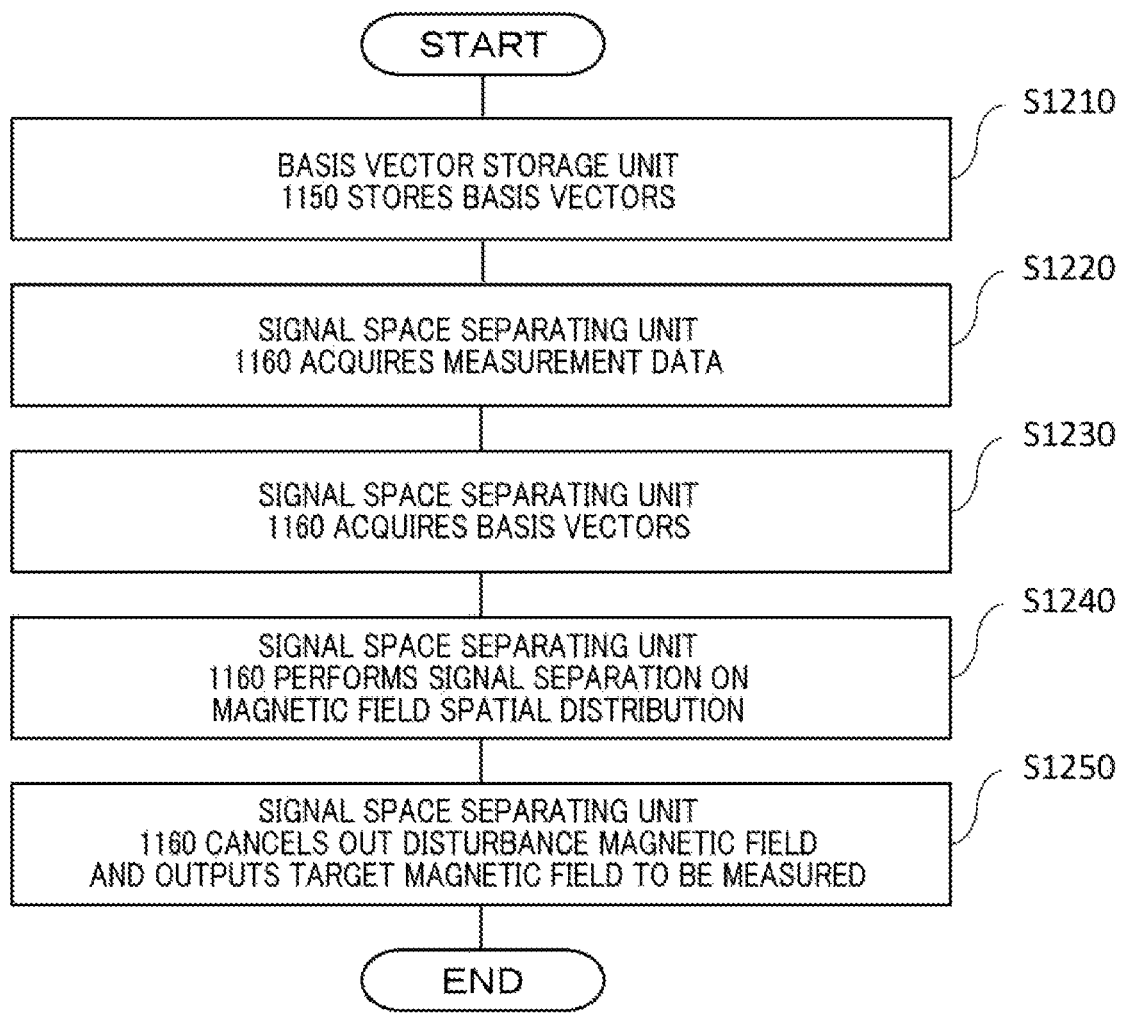
FIG. 12 illustrates a flow for the magnetic field measuring apparatus 10 according to this embodiment to perform signal separation on a magnetic field spatial distribution.

FIG. 12 illustrates a flow for the magnetic field measuring apparatus 10 according to this embodiment to perform signal separation on a magnetic field spatial distribution. In step 1210, the basis vector storage unit 1150 stores the basis vectors. As one example, the basis vector storage unit 1150 may store, as an initial basis vector, signal vectors that are predetermined by a result simulated assuming that the magnetic sensor array 210 is ideally built with no error in each sensor. Also, as described below, when the sensor error has been calibrated by the calibrating unit 1190, the basis vector storage unit 1150 may store the changed basis vectors after updating.

Next, in step 1220, the signal space separating unit 1160 acquires sensor array signal Φ measured by the magnetic sensor array 210, that is, measurement data V[1] to V[M], from the data output unit 1140.

Furthermore, in step 1230, the signal space separating unit 1160 acquires the signal vectors stored as the basis vectors in the basis vector storage unit 1150 in step 1210, from the basis vector storage unit 1150. In this flow, either of step 1220 or step 1230 may be performed before the other.

In step 1240, the signal space separating unit 1160 performs series-expansion on the spatial distribution of the magnetic field indicated by the measurement data VW to V[M] acquired in step 1220 by using, as the basis vectors, the signal vectors acquired in step 1230. Then, the signal space separating unit 1160 performs signal-separation on the spatial distribution of the magnetic field from the vector obtained by series-expansion into the target magnetic field to be measured and the disturbance magnetic field. That is, the signal space separating unit 1160 performs signal-separation on the spatial distribution of the input magnetic field indicated by the measurement data V[1] to V[M] using, as the basis vectors, the vector signal having the signal output by each of the magnetic sensors 520 as each signal component when the magnetic field with the spatial distribution of the orthonormal functions are detected by the magnetic sensor array 210. That is, based on the position and magnetic sensitivity of each magnetic sensor 520, in particular, from the orthonormal functions and the position and magnetic sensitivity of each magnetic sensor 520, basis vectors are calculated and the spatial distribution of the magnetic field indicated by the measurement data is signal-separated. Herein, the orthonormal functions may be the spherical harmonic functions. Also, the signal space separating unit 1160 calculates the coefficients of the basis vectors using the least-squares method in signal separation.

Then, in step 1250, the signal space separating unit 1160 calculates and outputs only the target magnetic field to be measured by suppressing the disturbance magnetic field based on the result of signal separation in step 1240, and ends the process. This will be described in detail below.

Regarding the position where each sensor configuring the magnetic sensor array 210 is arranged, when the current i(r)=0 at a position of a position vector r representing a position from the coordinate origin, the static magnetic field B(r) is obtained as a spatial gradient of a potential V(r), as shown in the expression below, using a potential V(r) that satisfies the Laplace equation Δ·V(r)=0. Herein, Δ is a Laplacian, μ is the magnetic permeability, and ∇ is an operator representing a vector differentiation operation.

$$B(r) = -\mu \cdot \nabla \cdot V(r) \quad \text{[Expression 4]}$$

Then, a solution to the Laplace equation is generally a solution in a form of series expansion using spherical harmonics Yl,m(θ,φ) which is an orthonormal function system, and thus the potential V(r) can be expressed as in the expression below. Herein, |r| is the absolute value of the position vector r (distance from the coordinate origin), θ and φ are two declination angles in spherical coordinates, l is a azimuthal quantum number, m is a magnetic quantum number, α and β are multipole moments, and Lin and Lout are respectively the number of series for the space in front of and the space behind the magnetic sensor array 210, when respectively viewed from the body to be measured. The azimuthal quantum number l is a positive integer, and the magnetic quantum number m is an integer in a range from −l to +l. That is, for example, when l is 1, m is −1, 0, and 1, and for example, when l is 2, m is −2, −1, 0, 1, and 2. Since there is no case of a single magnetic pole in the magnetic field, the azimuthal quantum number l starts from 1 instead of 0 in Expression 5. The first term in Expression 5 is a term inversely proportional to the distance from the coordinate origin and indicates the potential that exists in the space in front of the magnetic sensor array 210 when viewed from the body to be measured. Also, the second term in Expression 5 is a term proportional to the distance from the coordinate origin and indicates the potential that exists in the space behind the magnetic sensor array 210 when viewed from the body to be measured.

$$V(r) = \sum_{l=1}^{Lin} \sum_{m=-l}^{l} \alpha_{l,m} \cdot \left( \frac{1}{|r|^{l+1}} \cdot Y_{l,m}(\theta, \varphi) \right) + \sum_{l=1}^{Lout} \sum_{m=-l}^{l} \beta_{l,m} \cdot \left( |r|^l \cdot Y_{l,m}(\theta, \varphi) \right) \quad \text{[Expression 5]}$$

Accordingly, according to Expression 4 and Expression 5, the static magnetic field B(r) can be expressed by the expression below. Herein, the first term in Expression 6 indicates the magnetic field source that exists in the space in front of the magnetic sensor array 210 when viewed from the body to be measured, that is, for example, the cardiac magnetic field created by the electrical activity of the heart (the target magnetic field to be measured). Also, the second term in Expression 6 indicates the disturbance magnetic field created by the magnetic field source that exists in the space behind the magnetic sensor array 210 when viewed from the body to be measured.

$$B(r) = -\mu \sum_{l=1}^{Lin} \sum_{m=-l}^{l} \alpha_{l,m} \cdot \nabla \left( \frac{1}{|r|^{l+1}} \cdot Y_{l,m}(\theta, \varphi) \right) - \mu \sum_{l=1}^{Lout} \sum_{m=-l}^{l} \beta_{l,m} \cdot \nabla \left( |r|^l \cdot Y_{l,m}(\theta, \varphi) \right) \quad \text{[Expression 6]}$$

When the solution to the Laplace equation is expressed in a form of series expansion using the spherical harmonic functions, the general solution of such will be infinite series, but what needs to be obtained is a sufficient signal-to-noise ratio (SNR, which is a ratio of the to-be-measured magnetic field signal to the disturbance magnetic field and sensor noise) for measuring a biomagnetic field, which is regarded as being actually expressible with a series of approximately 10 terms. Furthermore, it is said that approximately Lin=8 and Lout=3 is sufficient for a series of a signal space separation in a magnetoencephalography. Accordingly, the case of Lin=8 and Lout=3 is described as one example also in this embodiment. However, the Lin and Lout values are not limited to this, and may be any numerical values that are sufficient for sufficiently suppressing the disturbance magnetic field and calculating the to-be-measured magnetic field only.

Herein, the sensor array signal Φ consists of M-dimensional vectors, and each signal component of the vectors is the inner product of the magnetic field vector B(r[m]) at the position vector r[m] where the magnetic sensors 520 of each sensor unit 300 are arranged and the magnetic sensitivity vector S[m] of each magnetic sensor 520. Therefore, for each magnetic sensor 520, when each has a magnetic sensitivity vector $S_{Ideal}[m]=(S_{Ideal}[m], x, S_{Ideal}[m], y, S_{Ideal}[m], z)$ as designed and arranged in the position as designed, the ideal sensor array signal $\Phi_{Ideal}$ is expressed by the expression below.

$$\begin{pmatrix} \phi_{Ideal}[1] \\ \phi_{Ideal}[2] \\ \vdots \\ \phi_{Ideal}[m] \\ \vdots \\ \phi_{Ideal}[M] \end{pmatrix} = \begin{pmatrix} \overrightarrow{S_{Ideal}[1]} \cdot \overrightarrow{B(r[1])} \\ \overrightarrow{S_{Ideal}[2]} \cdot \overrightarrow{B(r[2])} \\ \vdots \\ \overrightarrow{S_{Ideal}[m]} \cdot \overrightarrow{B(r[m])} \\ \vdots \\ \overrightarrow{S_{Ideal}[M]} \cdot \overrightarrow{B(r[M])} \end{pmatrix}$$

[Expression 7]

That is, each sensor signal component $\Phi_{Ideal}[m]$ that is ideally with no sensor error (a magnetic sensitivity error due to the cross-axis sensitivities or the main-axis sensitivity of each sensor, and a positional error due to the misalignment of the arrangement position of each sensor during the assembly of the magnetic sensor array 210, and so on) is expressed by the expression below.

$$\phi_{Ideal}[m] = S_{Ideal}[m], x \cdot Bx(r[m]) + S_{Ideal}[m],$$

[Expression 8]

$$y \cdot By(r[m]) + S_{Ideal}[m], z \cdot Bz(r[m])$$

$$m \in \{1, 2, \ldots, M\}$$

Accordingly, in the ideal case where there is no sensor error at each magnetic sensor 520, the basis vectors $a_{Ideal\ l,m}$ and $b_{Ideal\ l,m}$ are defined as the expressions below.

$$a_{Ideal\ l,m} = -\mu \begin{bmatrix} S_{Ideal}[1] \cdot \nabla\left(\frac{1}{r[1]^{l+1}} Y_{l,m}(\theta[1], \varphi[1])\right) \\ S_{Ideal}[2] \cdot \nabla\left(\frac{1}{r[2]^{l+1}} Y_{l,m}(\theta[2], \varphi[2])\right) \\ \vdots \\ S_{Ideal}[m] \cdot \nabla\left(\frac{1}{r[m]^{l+1}} Y_{l,m}(\theta[m], \varphi[m])\right) \\ \vdots \\ S_{Ideal}[M] \cdot \nabla\left(\frac{1}{r[M]^{l+1}} Y_{l,m}(\theta[M], \varphi[M])\right) \end{bmatrix}$$

[Expression 9]

$$b_{Ideal\ l,m} = -\mu \begin{bmatrix} S_{Ideal}[1] \cdot \nabla\left(r[1]^l Y_{l,m}(\theta[1], \varphi[1])\right) \\ S_{Ideal}[2] \cdot \nabla\left(r[2]^l Y_{l,m}(\theta[2], \varphi[2])\right) \\ \vdots \\ S_{Ideal}[m] \cdot \nabla\left(r[m]^l Y_{l,m}(\theta[m], \varphi[m])\right) \\ \vdots \\ S_{Ideal}[M] \cdot \nabla\left(r[M]^l Y_{l,m}(\theta[M], \varphi[M])\right) \end{bmatrix}$$

Herein, in the ideal case where there is no sensor error at each magnetic sensor 520, $A_{Ideal}$, $N_{Ideal}$, $X_{in}$ and $X_{out}$ are respectively defined as below. That is, $A_{Ideal}$ is defined as a vector with a total of $L_{in} \cdot (L_{in}+2)$ columns, where each vector $a_{Ideal}$ is arranged in column side-by-side in a sequence from $l=1$ to $l=L_{in}$ when taking an integer from $m=-l$ to $l$ at each $l$. Also, $B_{Ideal}$ is defined as a vector with a total of $L_{out} \cdot (L_{out}+2)$ columns, where each vector $b_{Ideal}$ is arranged in column side-by-side in a sequence from $l=1$ to $l=L_{out}$ when taking an integer from $m=-l$ to $l$ at each $l$. Yet further, $X_{in}$ is defined as a vector with a total of $L_{in} \cdot (L_{in}+2)$ rows obtained by transposing a vector, where each multipole moment $\alpha$ when taking an integer from $m=-l$ to $l$ at each $l$ is arranged in column side-by-side in a sequence from $l=1$ to $l=L_{in}$. Also, $X_{out}$ is defined as a vector with a total of $L_{out} \cdot (L_{out}+2)$ columns obtained by transposing a vector, where each multipole moment $\beta$ when taking an integer from $m=-l$ to $l$ at each $l$ is arranged in column side-by-side in a sequence from $l=1$ to $l=L_{out}$.

$$A_{Ideal} = [a_{Ideal_{1,-1}} a_{Ideal_{1,0}} a_{Ideal_{1,+1}} \cdots a_{Ideal_{Lin,Lin}}]$$

$$B_{Ideal} = [b_{Ideal_{1,-1}} b_{Ideal_{1,0}} b_{Ideal_{1,+1}} \cdots b_{Ideal_{Lout,Lout}}]$$

$$\text{Xin} = [\alpha_{1,-1} \alpha_{1,0} \alpha_{1,+1} \cdots \alpha_{Lin,Lin}]^t$$

$$\text{Xout} = [\beta_{1,-1} \beta_{1,0} \beta_{1,+1} \cdots \beta_{Lout,Lout}]^t$$

[Expression 10]

In this way, the sensor array signal $\Phi_{Ideal}$ of the ideal magnetic sensor array 210 can be expressed in the form of the inner product of the ideal basis vector matrix $[A\ B]_{Ideal}$ and the vertical vector X, as shown in the expression below. Herein, the ideal basis vector matrix $[A\ B]_{Ideal}$ indicates the basis vectors, for example, obtained by the signal space separating unit 1160 from the basis vector storage unit 1150 in step 1230. Also, a column vector X indicates coefficients according to the basis vectors.

$$\Phi_{Ideal} = [A\ B]_{Ideal} \cdot X = [A_{Ideal}\ B_{Ideal}] \begin{bmatrix} Xin \\ Xout \end{bmatrix}$$

[Expression 11]

In step 1240, the signal space separating unit 1160 uses the following expression based on the model expression obtained in this Expression 11 to determine the column vector $\hat{X}_{ideal}$ (herein, "$\hat{X}_{ideal}$" indicates the left side in Expression 12 and means the hat (estimated value) of $X_{Ideal}$) satisfying $\Phi_{Ideal}=[A\ B]_{Ideal} \cdot X$ with the least-squares approximation.

$$\widehat{X_{ideal}} = \begin{bmatrix} \widehat{Xin} \\ \widehat{Xout} \end{bmatrix} = [A\ B]_{Ideal}^\dagger \cdot \Phi_{Ideal} =$$

[Expression 12]

$$([A\ B]_{Ideal}^t \cdot [A\ B]_{Ideal})^{-1} \cdot [A\ B]_{Ideal}^t \cdot \Phi_{Ideal}$$

Accordingly, the signal space separating unit 1160 can express the hat $\hat{\Phi}_{Ideal}$ of the sensor array signal of the ideal magnetic sensor array 210 as an M-dimensional vector of the least-squares solution by the expression below. In this way, the signal space separating unit 1160 can solve the magnetic field spatial distribution in step 1240.

$$\widehat{\Phi_{ideal}} = [A\ B]_{Ideal} \cdot \{[A\ B]_{Ideal}^\dagger \cdot \Phi_{Ideal}\} =$$

[Expression 13]

$$[A\ B]_{Ideal} \cdot \{([A\ B]_{Ideal}^t \cdot [AB]_{Ideal})^{-1} \cdot [A\ B]_{Ideal}^t \cdot \Phi_{Ideal}\}$$

Then, in step 1250, the signal space separating unit 1160 outputs the result of suppressing the disturbance magnetic field component, that is, the component of the second term in Expression 6, by decreasing $\hat{X}_{out} \cdot B_{Ideal}$ using the column vector determined in step 1240. The signal space separating unit 1160 may also suppress the disturbance magnetic field component by outputting only $\hat{X}_{in} \cdot A_{Ideal}$ as a result, and output only the target magnetic field component to be measured, that is, the first term component in Expression 6.

In this way, according to the magnetic field measuring apparatus 10 of this embodiment, the magnetic field spatial distribution indicated by the measurement data V[1] to V[M] measured using the magnetic sensor array 210 having a plurality of magnetic sensor cells 220 and capable of detecting the input magnetic field in the three axial directions can be signal-separated into the target magnetic field to be measured and the disturbance magnetic field. Also, the magnetic field measuring apparatus 10 suppresses the disturbance magnetic field component and outputs only the target magnetic field component to be measured, thus the target magnetic field to be measured can be measured with higher accuracy. Further, since each of the plurality of sensor units 300 includes magnetic flux concentrators, it is possible to increase the magnetic sensitivity of the sensor units 300, while clarifying spatial sampling points, and increasing the affinity with signal space separating technology.

Figure 13:
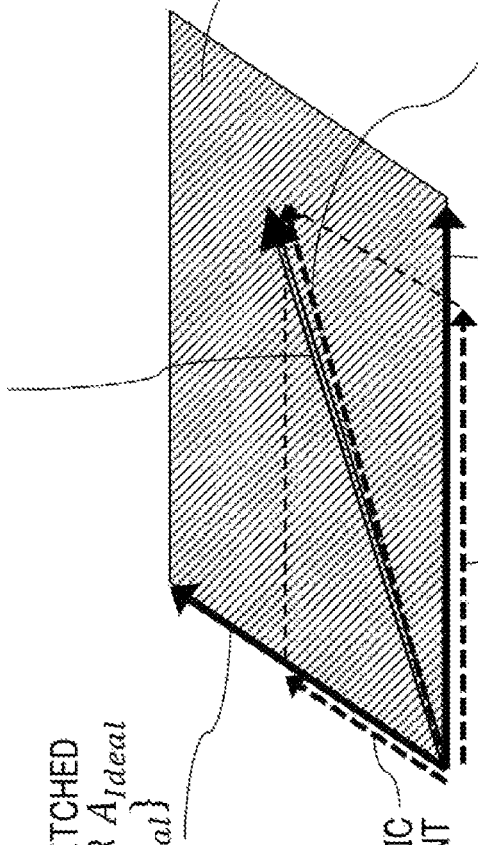
FIG. 13 illustrates geometrically a signal space separating calculation performed by using an ideal basis vector $[A\ B]_{Ideal}$ when the magnetic sensor array 210 is built ideally.

FIG. 13 illustrates geometrically a signal space separating calculation performed by using an ideal basis vector $[A\ B]_{Ideal}$ when the magnetic sensor array 210 is built ideally. The sign 1310 indicates the sensor array signal $\Phi_{Ideal}$ for an ideal magnetic sensor array 210. The sign 1320 indicates a linear subspace Span$\{A_{Ideal}\}$, which is created by an ideal basis vector $A_{Ideal}$. The sign 1330 indicates a linear subspace Span$\{B_{Ideal}\}$, which is created by an ideal basis vector Napa'. The sign 1340 indicates a linear subspace created by the ideal basis vector $[A\ B]_{Ideal}$, which is the linear sum of the linear subspace Span$\{A_{Ideal}\}$ and the linear subspace Span$\{B_{Ideal}\}$. The sign 1350 indicates an M-dimensional vector of the least-squares solution. As shown in this figure, when the magnetic sensor array 210 is built ideally, that is, built without sensor error, the sensor array signal $\Phi_{Ideal}$ of the ideal magnetic sensor array 210 exists in a linear subspace created by the ideal basis vector $[A\ B]_{Ideal}$. That is, the equation of Expression 11 is established with high accuracy, and the signal space separating unit 1160 is able to accurately perform signal space separation on the magnetic field detected by the magnetic sensor array 210 into the target magnetic field component and the disturbance magnetic field component.

However, the actual sensor signal component $\Phi_{Uncalib}[m]$ from each sensor unit 300 is expressed using the magnetic sensitivity vector $S_{Uncalib}[m]=(S_{Uncalib}[m], x, S_{Uncalib}[m], y, S_{Uncalib}[m], z)$, which includes the magnetic sensitivity error of each magnetic sensor 520. That is, the magnetic sensor array 210 is built assuming that the magnetic sensitivity vector $S_{Ideal}[m]=(S_{Ideal}[m], x, S_{Ideal}[m], y, S_{Ideal}[m], z)$ for each magnetic sensor 520, but actually the magnetic sensor array 210 is created with an unknown magnetic sensitivity vector $S_{Uncalib}[m]=(S_{Uncalib}[m], x, S_{Uncalib}[m], y, S_{Uncalib}[m], z)$ that deviates from that vector.

That is, each sensor signal component $\Phi_{Uncalib}[m]$ with magnetic sensitivity error will be expressed by the expression below.

$$\Phi_{Uncalib}[m] = S_{Uncalib}[m], x \cdot Bx(r[m]) + S_{Uncalib}[m], \quad \text{[Expression 14]}$$

$$y \cdot By(r[m]) + S_{Uncalib}[m], z \cdot Bz(r[m])$$

$$m \in \{1, 2, \dots, M\}$$

In this way, for the sensor array signal $\Phi_{Uncalib}$ measured by the magnetic sensor array 210 created with a magnetic sensitivity error, the expression below is established using the ideal basis vector $[A\ B]_{Ideal}$ that has been assumed.

$$\Phi_{Uncalib} = [A\ B]_{Ideal} \cdot X_{Uncalib} = [A\ B]_{Ideal} \cdot \begin{bmatrix} Xin_{Uncalib} \\ Xout_{Uncalib} \end{bmatrix} \quad \text{[Expression 15]}$$

In this way, even if the column vector $\hat{X}_{Uncalib}$ is determined by the expression below based on the model expression obtained in Expression 15, the solution of the equation ends up being inaccurate.

$$\hat{X}_{Uncalib} = \begin{bmatrix} \widehat{Xin_{Uncalib}} \\ \widehat{Xout_{Uncalib}} \end{bmatrix} = [A\ B]^\dagger_{Ideal} \cdot \Phi_{Uncalib} = \quad \text{[Expression 16]}$$

$$([A\ B]^t_{Ideal} \cdot [A\ B]_{Ideal})^{-1} \cdot [A\ B]^t_{Ideal} \cdot \Phi_{Uncalib}$$

In this case, as an M-dimensional vector of the least-squares solution, the hat $\hat{\Phi}_{Uncalib}$ of the sensor array signal of the magnetic sensor array 210 with a magnetic sensitivity error is shown by the expression below.

$$\hat{\Phi}_{Uncalib} = \quad \text{[Expression 17]}$$

$$[A\ B]_{Ideal} \cdot \{[A\ B]^\dagger_{Ideal} \cdot \Phi_{Uncalib}\} = [A\ B]_{Ideal} \cdot$$

$$\{([A\ B]^t_{Ideal} \cdot [A\ B]_{Ideal})^{-1} \cdot [A\ B]^t_{Ideal} \cdot \Phi_{Uncalib}\}$$

Figure 14:
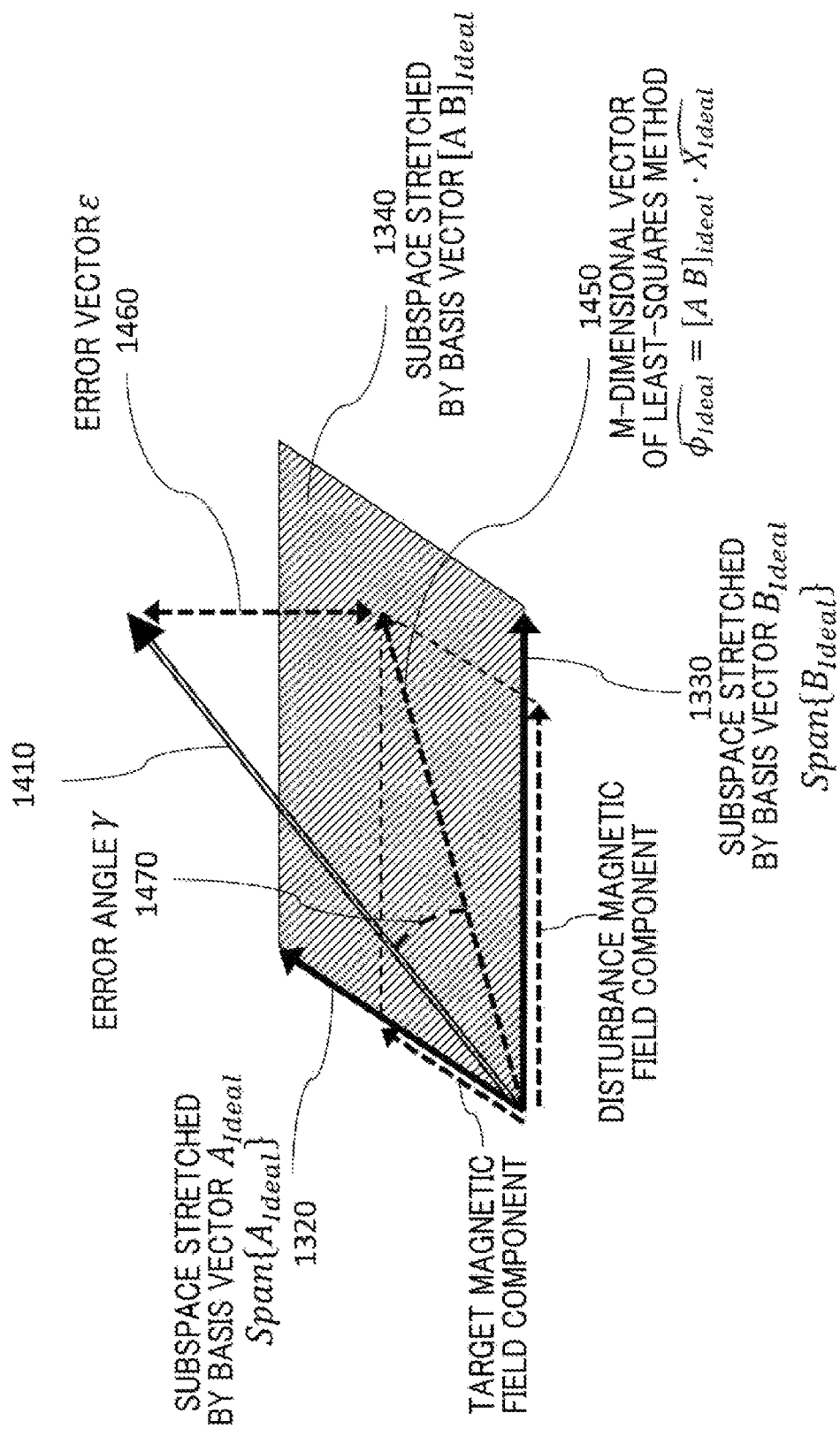
FIG. 14 illustrates geometrically a signal space separating calculation performed by using an ideal basis vector $[A\ B]_{Ideal}$ when the magnetic sensor array 210 is built with a sensor error.

FIG. 14 illustrates geometrically a signal space separating calculation performed by using an ideal basis vector $[A\ B]_{Ideal}$ when the magnetic sensor array 210 is built with a sensor error. In FIG. 14, members having the same function and configuration as in FIG. 13 are given the same reference numerals, and the following describes only differing points. The sign 1410 indicates the sensor array signal $\Phi_{Uncalib}$ of the magnetic sensor array 210 with a sensor error. The sign 1450 indicates the M-dimensional vector of the least-squares solution. As shown in this figure, when the magnetic sensor array 210 has a sensor error, the sensor array signal $\Phi_{Uncalib}$ will not exist in the linear subspace created by the ideal basis vector $[A\ B]_{Ideal}$.

At this time, between the sensor array signal $\Phi_{Uncalib}$, indicated by the sign 1410, and the M-dimensional vector $\hat{\Phi}_{Uncalib}$ of the least-squares solution, indicated by the sign 1450, a separation error, which means the error vector ε, indicated by the sign 1460, and the error angle γ, indicated by the sign 1470, is generated. Herein, the error vector ε and the error angle γ are indicated by the expression below.

$$\varepsilon = \Phi_{Uncalib} - \hat{\Phi}_{Uncalib} = \Phi_{Uncalib} - [A\ B]_{Ideal} \cdot \hat{X}_{Uncalib} \quad \text{[Expression 18]}$$

$$\gamma = \tan^{-1}\left(\frac{\|\Phi_{Uncalib} - \hat{\Phi}_{Uncalib}\|}{\|\hat{\Phi}_{Uncalib}\|}\right)$$

In this way, due to the sensor error of the actual magnetic sensor array 210, the error vector ε in the signal space separating calculation is generated as a finite vector (not a zero vector). Accordingly, the equation of Expression 15 is not established with high accuracy, and the solution to the equation shown in Expression 16 is inaccurate. That is, the signal space separating unit 1160 cannot accurately perform signal space separation for the magnetic field detected by the magnetic sensor array 210 into the target magnetic field component and the disturbance magnetic field component.

Therefore, the magnetic field measuring apparatus 10 according to this embodiment calibrates (performs a calibration) the sensor error in the magnetic sensor 520 so as to reduce the separation error in the case of performing such a signal space separating calculation.

Figure 15:
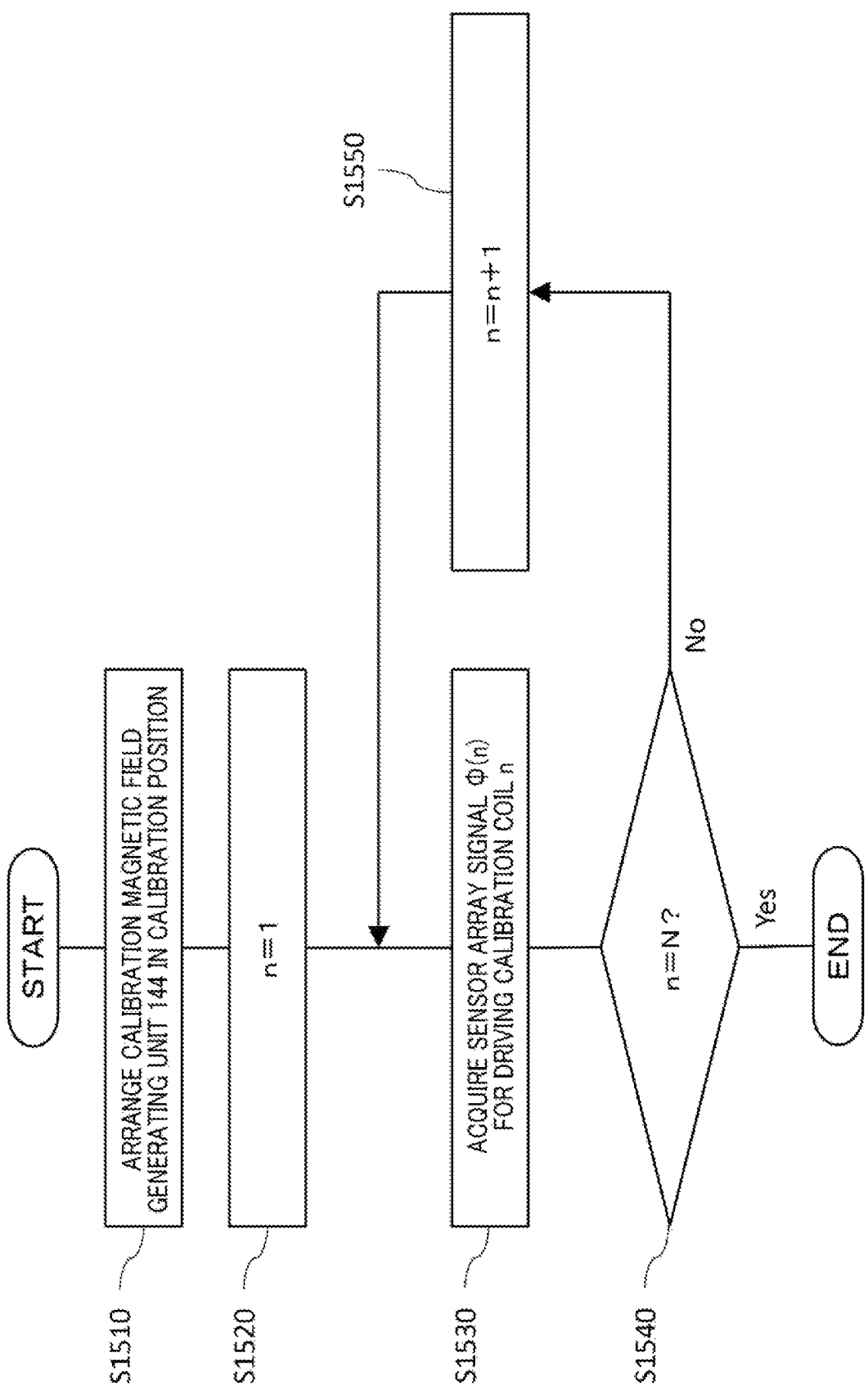
FIG. 15 illustrates a flow for the magnetic field measuring apparatus 10 according to this embodiment to acquire a sensor array signal Φ (n) for calibration.

FIG. 15 illustrates a flow for the magnetic field measuring apparatus 10 according to this embodiment to acquire a sensor array signal Φ(n) for calibration. In step 1510, the magnetic field measuring apparatus 10 arranges the calibration magnetic field generating unit 144 on the side facing the body to be measured when viewed from the magnetic sensor array 210, preferably at the position indicated by dots in FIG. 10.

In step 1520, the magnetic field measuring apparatus 10 substitutes 1 in n. Herein, n is a number that identifies the calibration coil included in the calibration magnetic field generating unit 144, and indicates an integer from 1 to N, N being the number of calibration coils included in the calibration magnetic field generating unit 144.

In step 1530, the magnetic field measuring apparatus 10 drives the calibration coil (n) and acquires the sensor array signal Φ(n). As one example, the calibration magnetic field generating unit 144 receives an alternating current corresponding to the frequency of the clock signal for calibration supplied from the calibration clock generating unit 1170, and applies the alternating current corresponding to the frequency of the said clock signal to the calibration coil (n) to generate an alternating magnetic field corresponding to the frequency of the clock signal from the calibration coil (n). At this time, the calibration magnetic field generated by the calibration coil (n) will be close to the magnetic field generated by the magnetic-dipole. Then, the calibration magnetic field generated by the calibration coil (n) corresponds to the component of the first term in Expression 6. In this case, by generating an alternating magnetic field of relatively high strength from the calibration coil (n), the component of the second term in Expression 6, that is, the effect of the disturbance magnetic field can be neglected during a calibration.

Then, the magnetic field measuring apparatus 10 obtains the sensor array signal Φ(n) when the calibration magnetic field is generated from the calibration coil (n). In more detail, when the calibration magnetic field is generated from the calibration coil (n), the measurement data acquiring unit 1120 acquires the measurement data V[1] to V[M] measured by the plurality of sensor units 300[1] to 300[M] included in the magnetic sensor array 210, respectively. Then, the synchronous detection unit 1130 receives the clock signal for calibration supplied by the calibration clock generating unit 1170, and synchronously detects the calibration magnetic field according to the clock signal. Then, the synchronous detection unit 1130 extracts the frequency components synchronized with the calibration magnetic field, which is an alternating magnetic field, from among the measurement data V[1] to V[M], and supplies the measurement data V[1] to V[M] according to the extracted frequency components to the data output unit 1140, respectively. Then, the data output unit 1140 supplies, to the signal space separating unit 1160, the sensor array signal Φ(n) for calibration including respective sensor signal components Φ(n)[1] to Φ(n)[M] from the plurality of sensor units 300[1] to 300[M] in the case where the calibration magnetic field has been generated from the calibration coil (n), Φ(n)[1] to Φ(n)[M] being equivalent to the measurement data V[1] to V[1\4] supplied by the synchronous detection unit 1130. As a result, the signal space separating unit 1160 obtains the sensor array signal Φ(n) for calibration in the case where the calibration magnetic field has been generated from the calibration coil (n).

In step 1540, the magnetic field measuring apparatus 10 determines whether n is equal to N. That is, the magnetic field measuring apparatus 10 determines whether all the calibration coils that are included in the calibration magnetic field generating unit 144 have been driven. When n is determined to be equal to N, that is, when it is determined that all the calibration coils have been driven, the magnetic field measuring apparatus 10 ends the flow of acquiring the sensor array signal Φ(n) for calibration.

On the other hand, when it is determined in step 1540 that n is not equal to N, that is, not all calibration coils have been driven, the magnetic field measuring apparatus 10 increments n to n=n+1 in step 1550, and returns the process to step 1530 to continue the flow.

In this way, the magnetic field measuring apparatus 10 acquires the sensor array signal Φ(n) for calibration in the case where N calibration coils are driven to generate the calibration magnetic field from n=1 to n=N, respectively.

Figure 16:
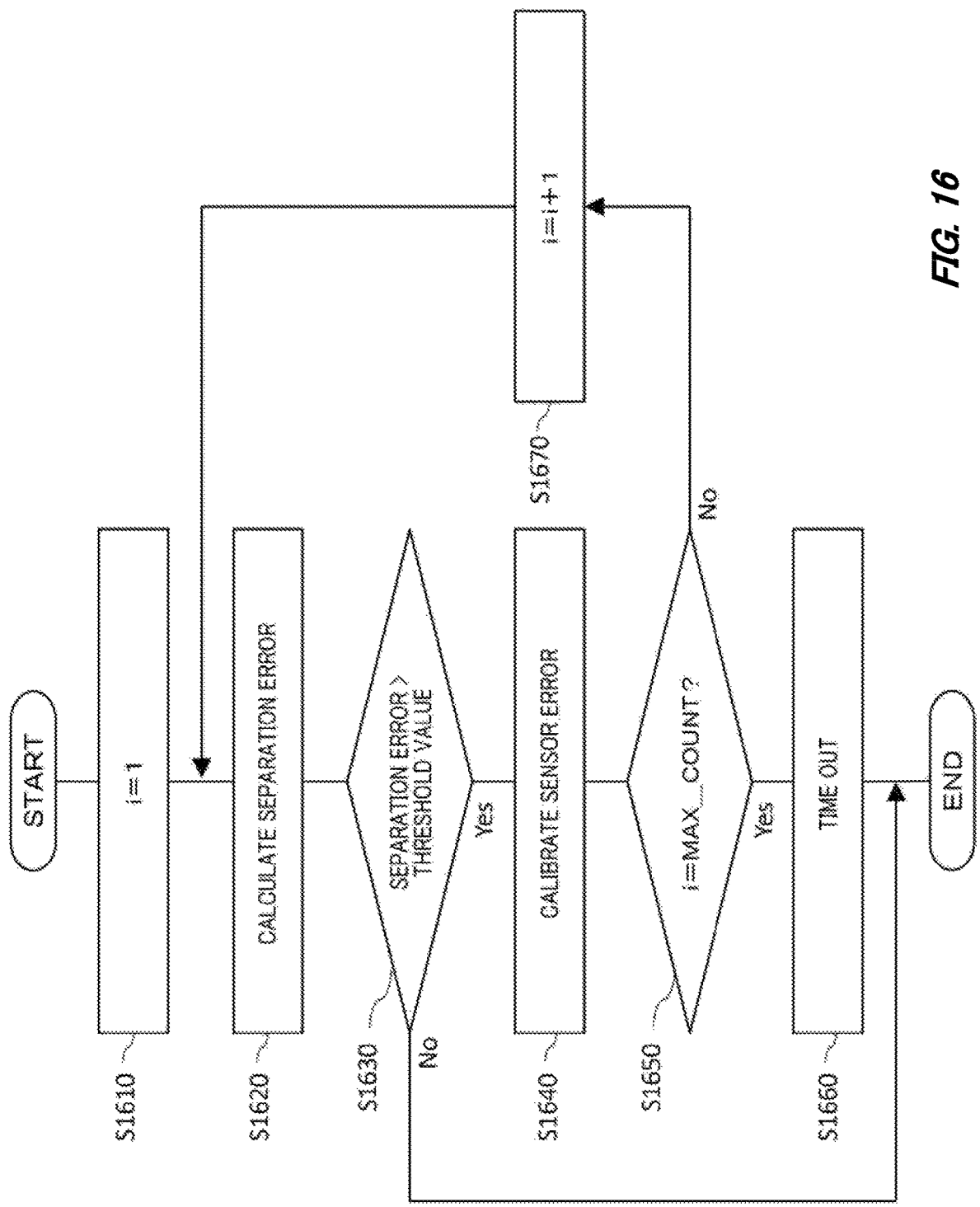
FIG. 16 illustrates a flow for the magnetic field measuring apparatus 10 according to this embodiment to perform the calibration.

FIG. 16 illustrates a flow for the magnetic field measuring apparatus 10 according to this embodiment to perform the calibration. In step 1610, the magnetic field measuring apparatus 10 substitutes 1 in i. Herein, i indicates the number of times of performing the calibration, and indicates an integer from 1 to MAX_COUNT, the upper limit of the number of times of performing the calibration.

In step 1620, the magnetic field measuring apparatus 10 calculates the separation error. In more detail, the signal space separating unit 1160 performs signal space separation on the sensor array signal Φ(n) for calibration for 1≤n≤N, respectively. In this case, in step 1620 following step 1610, the signal space separating unit 1160 determines the solution of the equation shown in Expression 16 from the equation shown in Expression 15. In this case, the signal space separating unit 1160 uses the position where the calibration magnetic field generating unit 144 is arranged as the coordinate origin in calculation in performing signal separation on the spatial distribution of the calibration magnetic field. That is, the signal space separating unit 1160 uses the position where the calibration coil (1) is arranged as the coordinate origin in calculation in performing signal separation on the sensor array signal Φ(1). Similarly, the signal space separating unit 1160 uses the position where the calibration coil (n) is arranged as the coordinate origin for calculation in performing signal separation on the sensor array signal Φ(n). In this way, when the calibration magnetic field generating unit 144 has N calibration coils and the calibration magnetic field is generated from each of the N calibration coils, the signal space separating unit 1160 performs the signal space separating calculation and error c calculation on the sensor array signal Φ(n) when the calibration magnetic field is generated from the calibration coil (n), during which sequentially conforming the coordinate origin in the signal space separating calculation to the position where the calibration coils (n) are arranged. This enables the magnetic field measuring apparatus 10 to greatly simplify the calibration of each magnetic sensor 520 in the M sensor units 300 included in the magnetic sensor array 210, and to accelerate the convergence of the calibration parameters. Then, the error calculating unit 1180 calculates at least any one of the error vector ε(n) and the error angle γ(n) as the separation error for 1≤n≤N, respectively, based on Expression 18.

In step 1630, the magnetic field measuring apparatus 10 determines whether the separation error exceeds a predetermined threshold value. For example, the magnetic field measuring apparatus 10 determines whether the sum of squares of N separation errors exceeds a predetermined threshold value. That is, the magnetic field measuring apparatus 10 determines whether at least any one of the sum of squares of the error vector ε(n) and the sum of squares of the error angle γ(n) for 1≤n≤N exceeds the predetermined threshold value. When it is determined that the separation error does not exceed the threshold value, the magnetic field measuring apparatus 10 ends the process considering as the calibration having been completed.

On the other hand, in step 1630, when it is determined that the separation error exceeds the predetermined threshold value, the magnetic field measuring apparatus 10 calibrates the sensor error in step 1640. For example, the calibrating unit 1190 optimizes the magnetic sensitivity vector $S_{Calib}$ [m] for 1≤m≤M so that at least one of the separation error as an objective function, that is, the error vector ε(n) and the error angle γ(n), is set to zero. In this case, the calibrating unit 1190, for example, may use computer science methods such as Stochastic annealing. Herein, the basis vectors after calibration is expressed as the expression below. In this way, the calibrating unit 1190 changes the basis vectors by optimizing the magnetic sensitivity vector $S_{Calib}$[m] so as to minimize the separation error.

$$a_{Calib\,l,m} = -\mu \begin{bmatrix} S_{Calib}[1] \cdot \nabla\left(\frac{1}{r[1]^{l+1}} Y_{l,m}(\theta[1], \varphi[1])\right) \\ S_{Calib}[2] \cdot \nabla\left(\frac{1}{r[2]^{l+1}} Y_{l,m}(\theta[2], \varphi[2])\right) \\ \vdots \\ S_{Calib}[m] \cdot \nabla\left(\frac{1}{r[m]^{l+1}} Y_{l,m}(\theta[m], \varphi[m])\right) \\ \vdots \\ S_{Calib}[M] \cdot \nabla\left(\frac{1}{r[M]^{l+1}} Y_{l,m}(\theta[M], \varphi[M])\right) \end{bmatrix}$$ [Expression 19]

$$b_{Calib\,l,m} = -\mu \begin{bmatrix} S_{Calib}[1] \cdot \nabla\left(r[m]^{l} Y_{l,m}(\theta[1], \varphi[1])\right) \\ S_{Calib}[2] \cdot \nabla\left(r[m]^{l} Y_{l,m}(\theta[2], \varphi[2])\right) \\ \vdots \\ S_{Calib}[m] \cdot \nabla\left(r[m]^{l} Y_{l,m}(\theta[m], \varphi[m])\right) \\ \vdots \\ S_{Calib}[M] \cdot \nabla\left(r[m]^{l} Y_{l,m}(\theta[M], \varphi[M])\right) \end{bmatrix}$$

In step 1650, the magnetic field measuring apparatus 10 determines whether i is equal to MAX_COUNT. That is, the magnetic field measuring apparatus 10 determines whether the number of times of performing the calibration has reached the upper-limit.

When i is equal to MAX_COUNT, that is, when the number of times of performing the calibration has reached the upper-limit, the magnetic field measuring apparatus 10 times out the performance of the calibration and ends the process in step 1660. In this case, the magnetic field measuring apparatus 10 may also report that, for example, the calibration has been timed out.

On the other hand, when i is not equal to MAC_COUNT, the magnetic field measuring apparatus 10 increments i to i=i+1 in step 1670, and returns the process to step 1620 to continue the flow. In step 1620 following step 1670, the signal space separating unit 1160 may determine the solution of the equation according to the expression below instead of Expression 16.

$$\widehat{X_{Calib}} = \begin{bmatrix} \widehat{Xin_{Calib}} \\ \widehat{Xout_{Calib}} \end{bmatrix} = [A\ B]^\dagger_{Calib} \cdot \Phi_{Uncalib} =$$ [Expression 20]

$$([A\ B]^t_{Calib} \cdot [A\ B]_{Calib})^{-1} \cdot [A\ B]^t_{Calib} \cdot \Phi_{Uncalib}$$

Also, the signal space separating unit 1160 may determine the hat, $\hat{\Phi}_{Calib}$, of the sensor array signal of the magnetic sensor array 210 with the sensor error as an M-dimensional vector of the least-squares solution by the expression below.

$$\hat{\Phi}_{Calib} = [A\ B]_{Calib} \cdot \{[A\ B]^\dagger_{Calib} \cdot \Phi_{Uncalib}\} = [A\ B]_{Calib} \cdot$$ [Expression 21]

$$\{([A\ B]^t_{Calib} \cdot [A\ B]_{Calib})^{-1} \cdot [A\ B]^t_{Calib} \cdot \Phi_{Uncalib}\}$$

Then, the signal space separating unit 1160 may calculate the separation error between the sensor array signal $\Phi_{Calib}$ and the M-dimensional vector $\hat{\Phi}_{Calib}$ of the least-squares solution using a method similar to Expression 18.

Figure 17:
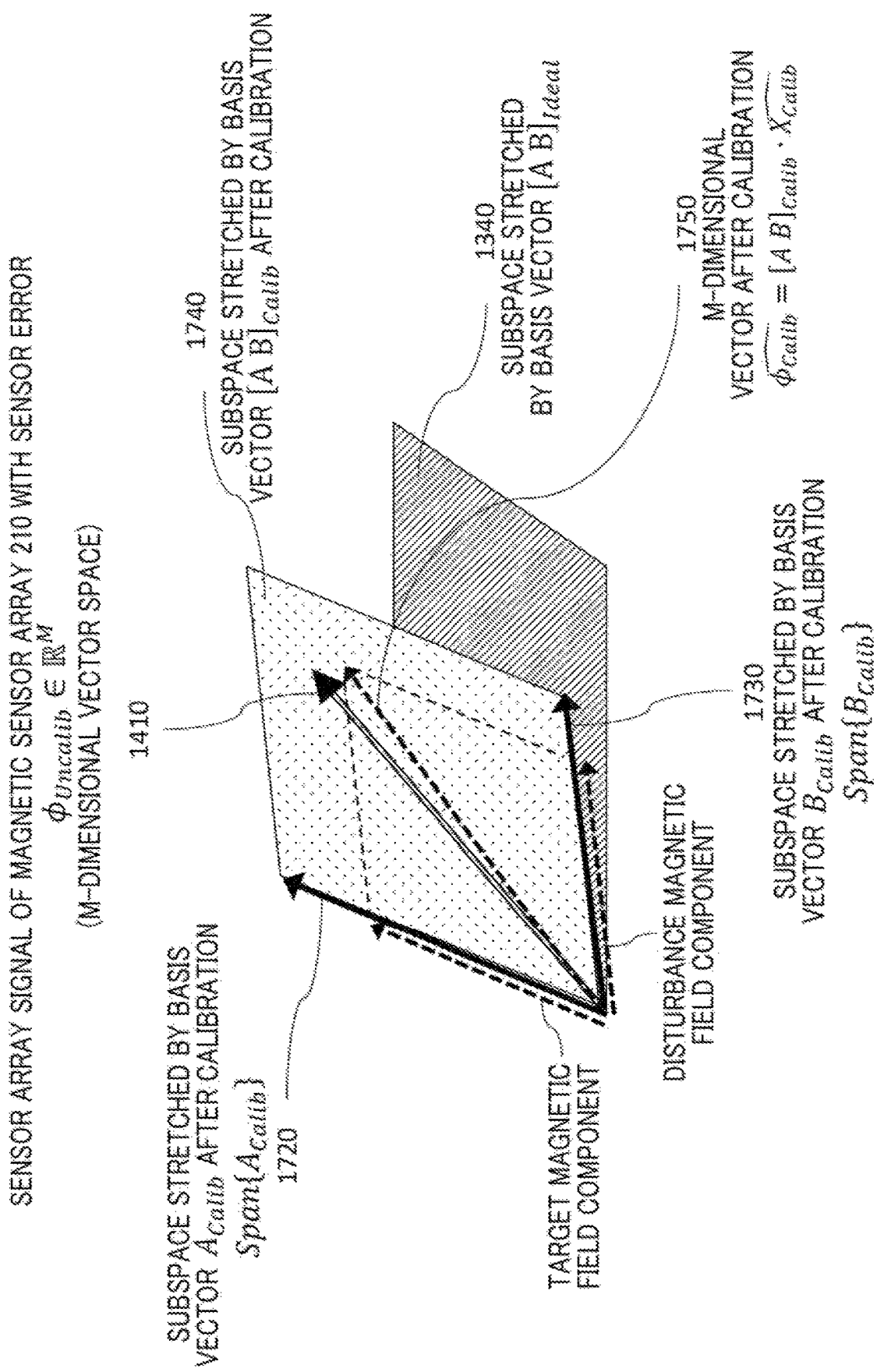
FIG. 17 illustrates geometrically a signal space separating calculation performed by using a basis vector $[A\ B]_{Calib}$ after calibration when the magnetic sensor array 210 is built with a sensor error.

FIG. 17 illustrates geometrically a signal space separating calculation performed by using a basis vector [A B]$_{Calib}$ after calibration when the magnetic sensor array 210 is built with a sensor error. In FIG. 17, members having the same function and configuration as in FIG. 14 are given the same reference numerals, and the following describes only differing points. According to the flow in FIG. 16, the magnetic field measuring apparatus 10 updates the basis vectors. Herein, the sign 1720 indicates a linear subspace Span{A$_{Calib}$}, which is created by a basis vector A$_{Calib}$ after calibration. Herein, the sign 1730 indicates a linear subspace Span{B$_{Calib}$}, which is created by a basis vector B$_{Calib}$ after calibration. The sign 1740 indicates a linear subspace created by the basis vector [A B]$_{Calib}$, which is the linear sum of the linear subspace Span{A$_{Calib}$} and the linear subspace Span{B$_{Calib}$}. The sign 1750 indicates an M-dimensional vector of the least-squares solution. As shown in this figure, the sensor array signal $\Phi_{Uncalib}$ of the magnetic sensor array 210 with a sensor error exists in a linear subspace created by the basis vector [A B]$_{Calib}$ after calibration. That is, the signal space separating unit 1160 can accurately perform signal space separation on the magnetic field detected by the magnetic sensor array 210 into the target magnetic field component and the disturbance magnetic field component by optimizing the basis vectors to minimize the separation error.

In the above description, the case where the magnetic field measuring apparatus 10 changes the basis vectors to minimize the separation error by optimizing the magnetic sensitivity vector $S_{Calib}$ [m] as a calibration parameter has been shown as one example. However, as mentioned above, for sensor errors, positional errors due to the misalignment of the arrangement position of each sensor during the assembly of the magnetic sensor array 210 can be generated in addition to the magnetic sensitivity error of each sensor. Accordingly, instead of or in addition to the magnetic sensitivity vector $S_{Calib}$ [m] as a calibration parameter, the magnetic field measuring apparatus 10 may also change the basis vectors to minimize the separation error by optimizing the position information at the magnetic sensors 520 of the M sensor units 300, in this case, the position information in the computational coordinate system of the signal space separation, that is, each of the dynamic diameter r, the zenith angle θ, and the azimuth angle φ. That is, the basis vectors may also be changed by using r, θ, and φ in Expression 19 as calibration parameters. The magnetic field measuring apparatus 10 can achieve such calibration of positional error by using a method similar to the calibration for magnetic sensitivity error. Also, the magnetic field measuring apparatus 10 may perform calculations to optimize the calibration of the magnetic sensitivity error and the calibration of the positional error at the same time.

Also, in the above description, the case where the magnetic field measuring apparatus 10 measures the target magnetic field to be measured after performing the calibration is shown as one example. However, when the magnetic field measuring apparatus 10 is arranged in a position that does not interfere with the measurement of the target magnetic field to be measured, and when the frequency of the alternating magnetic field as the calibration magnetic field is higher than the frequency band of the target magnetic field to be measured, the magnetic field measuring apparatus 10 may perform calibration and measurement of the target magnetic field to be measured simultaneously. In this case, the magnetic field measuring apparatus 10 may perform frequency separation on the calibration magnetic field signal and the target magnetic field signal to be measured by using LPF, HPF or the like.

Figure 18:
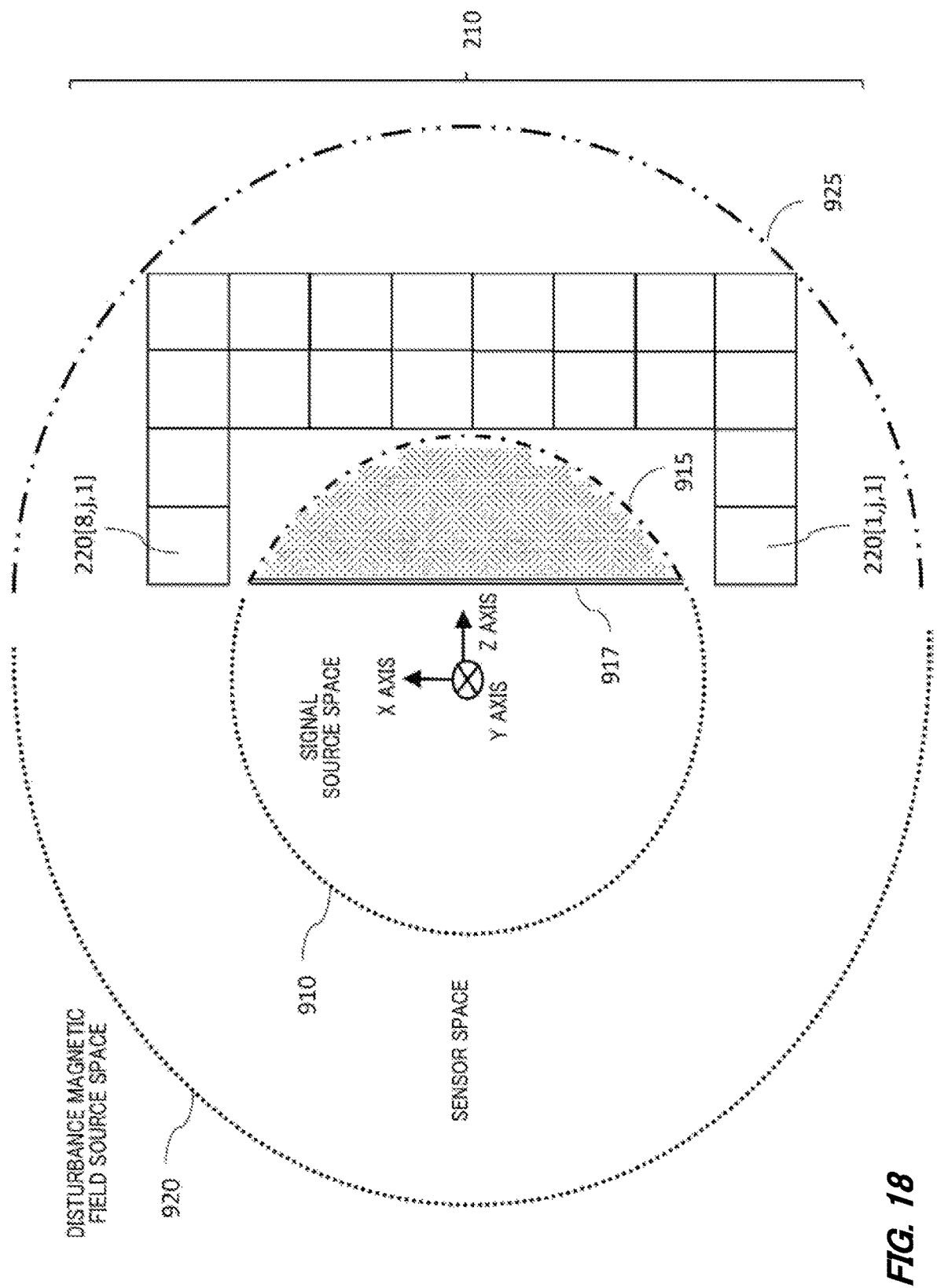
FIG. 18 illustrates another example of a preferred arrangement position of the calibration magnetic field generating unit 144 during calibration.

FIG. 18 illustrates another example of a preferred arrangement position of the calibration magnetic field generating unit 144 during calibration. In FIG. 18, members having the same function and configuration as in FIG. 10 are given the same reference numerals, and the following describes only differing points. As shown in this figure, the magnetic sensor array 210 may be configured with a plurality of magnetic sensor cells 220 arrayed in a U-shaped in a cross-sectional view, in configuring the plurality of magnetic sensor cells 220 to be arrayed in a three-dimensional arrangement so that they are arranged at grid points included in the curved surface shape.

In more detail, some of magnetic sensor cells 220, that is, [1,j,3] to 220[8,j,3] and 220[1,j,4] to 220[8,j,4], may be linearly arranged between the outside of the inscribed circle 910 and the inside of the circumscribed circle 920. Then, the remaining magnetic sensor cells 220 [1,j,1] to [1,j,2] and 220 [8,j,1] to 220 [8,j,2] may be arranged extending in the minus Z axis direction from each of the magnetic sensor cells 220 [1,j,3] and 220 [8,j,3] located at one end of the linear arrangement. In such a configuration, the centers of the inscribed and circumscribed circles are common and match the coordinate origin in the signal separating calculation. Then, the calibration magnetic field generating unit 144 may then be arranged inside the region enclosed by the arc 915 and the string 917 connecting the both end points of the arc 915. That is, the calibration magnetic field generating unit 144 may be arranged in the region indicated by dots in this figure.

In the above description, the case where the calibration magnetic field generating unit 144 is arranged inside the region enclosed by the arc 915 of the circle 910 inscribed in the magnetic sensor array 210 and the string 917 connecting both end points of the arc 915 is shown as one example. However, it is not limited to this. By arranging the source of the calibration magnetic field in the vicinity of the magnetic sensor array 210, the calibration magnetic field provided to each magnetic sensor 520 can be made stronger relative to the environmental magnetic field. On the other hand, in the case that each magnetic sensor 520 includes magnetic flux concentrators 720 and 730, when the source of the calibration magnetic field is arranged in the vicinity of the magnetic sensor array 210, distortion of the magnetic field by the magnetic flux concentrators 720 and 730 can occur. That is, the gradient of the magnetic field dependent on the distance from the source of the calibration magnetic field cannot be neglected, resulting in difference in density of the magnetic flux distribution between one end and another end in each of the magnetic flux concentrators 720 and 730. Also, the effect of the gradient of such a magnetic field on each axial direction of the magnetic sensors 520 depends on the orientation of the source of the calibration magnetic field when viewed from each magnetic sensor 520. For such a reason, the sensitivity of each magnetic sensor 520 can vary depending on the position of the source of the calibration magnetic field. Accordingly, in such a case, the source of the calibration magnetic field may be away from the magnetic sensor array 210, to some extent. This will be described in detail using figures.

Figure 19:
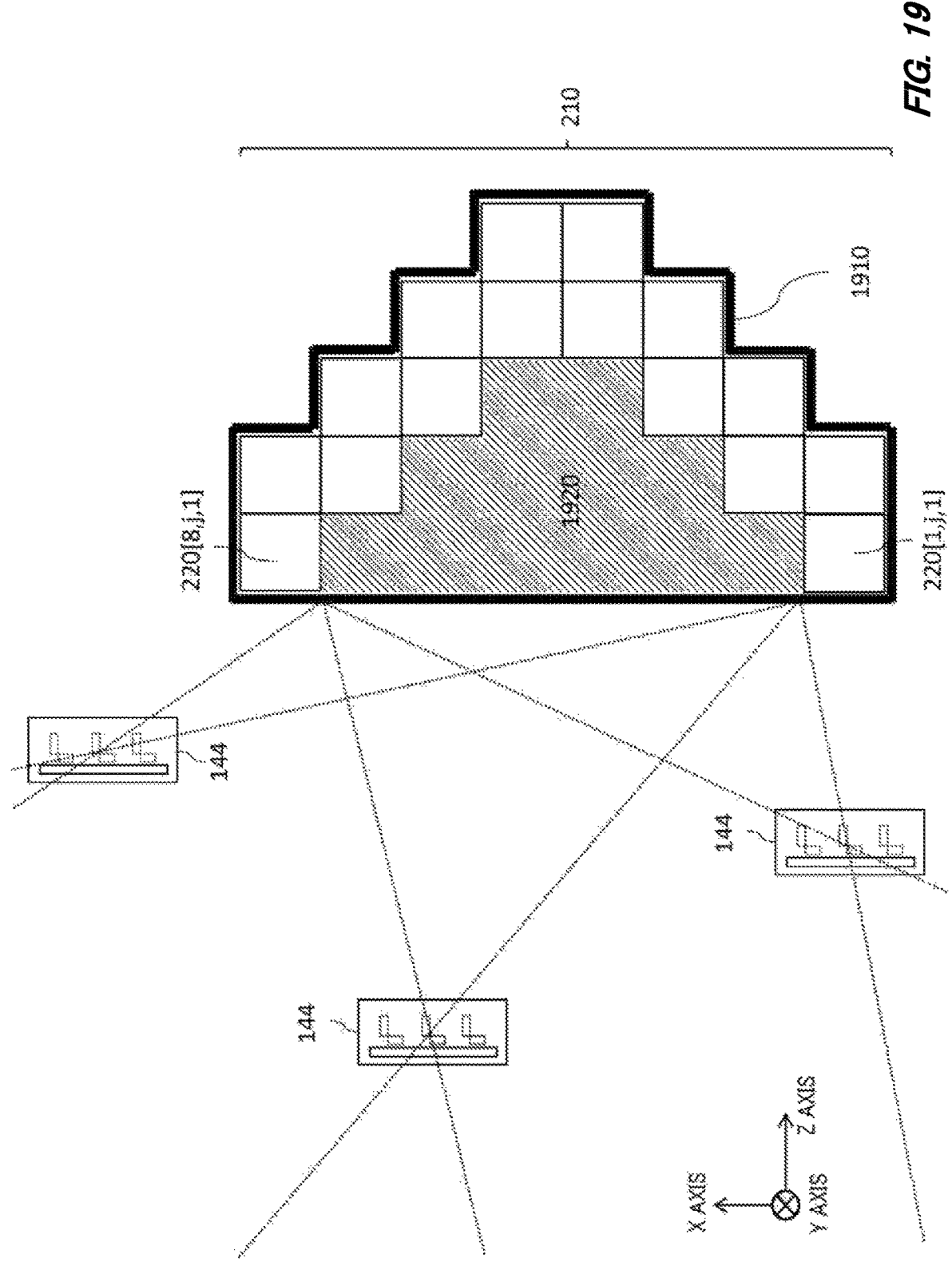
FIG. 19 illustrates another exemplary arrangement of the calibration magnetic field generating unit 144 during calibration.

FIG. 19 illustrates another exemplary arrangement of the calibration magnetic field generating unit 144 during calibration. As described above, the magnetic field measuring apparatus 10 includes a magnetic sensor array 210 configured by arraying a plurality of magnetic sensor cells 220 to form a surface covering at least a part of the target object to be measured (for example, the heart), each of the plurality of magnetic sensor cells having a magnetic sensor 520 including a magnetoresistive element 710 and magnetic flux concentrators 720 and 730. Then, each of the plurality of magnetic sensor cells 220 further has a magnetic field generating unit 530 for generating a feedback magnetic field that reduces the input magnetic field detected by the magnetic sensor 520, and an output unit 540 for outputting an output signal corresponding to a flowing feedback current that the magnetic field generating unit 530 applies to generate the feedback magnetic field. Then, the magnetic field measuring apparatus 10 includes a measurement data acquiring unit 1120 for acquiring the measurement data measured by such a magnetic sensor array 210, a signal space separating unit 1160 for performing signal-separation on the spatial distribution of the magnetic field indicated by the measurement data based on the position and magnetic sensitivity of each magnetic sensor 520, in particular, based on the basis vectors calculated from the orthonormal functions and the position and magnetic sensitivity of each magnetic sensor 520, a calibration magnetic field generating unit 144 for generating the calibration magnetic field, and a calibrating unit 1190 for calibrating the sensor error in the magnetic sensor 520 based on the separation error in the case where the signal separation has been performed on the spatial distribution of the calibration magnetic field. The orthonormal functions may be the spherical harmonic functions.

In such a magnetic field measuring apparatus 10, the calibration magnetic field generating unit 144 may be arranged in the position shown in this figure to suppress the distortion of the magnetic field caused by the magnetic flux concentrators 720 and 730. That is, the calibration magnetic field generating unit 144 may generate the calibration magnetic field at a position on a straight line that can be drawn from the measurement space 1920 without crossing the plurality of magnetic sensor cells 220 outside the measurement space 1920 (shaded in this figure) where the plurality of magnetic sensor cells 220 are not arranged in the closed space (enclosed by a bold line in this figure) that is composed of the smallest convex polygon 1910 that includes all of the plurality of magnetic sensor cells 220 in a cross-sectional view. As shown in this figure, the magnetic field measuring apparatus 10 may, for example, arrange the calibration magnetic field generating unit 144 on the minus side of the Z axis relative to the magnetic sensor array 210. In this way, the magnetic field measuring apparatus 10 generates the calibration magnetic field at a position where the source of the calibration magnetic field is a certain distance away from each magnetic sensor 520 and at a position where each orientation when viewed from each magnetic sensor 520 is aligned to a certain degree. In this way, according to the magnetic field measuring apparatus 10, a calibration magnetic field that is uniform to such an extent as being able to neglect the effect due to the magnetic field gradient can be provided to each magnetic sensor 520, thus the distortion of the magnetic field caused by the magnetic flux concentrators 720 and 730 can be suppressed. Here, the measurement space 1920 may be used for arranging the target object to be measured.

However, there is a trade-off, that is, the distortion of the magnetic field caused by the magnetic flux concentrators 720 and 730 can be suppressed by moving the source of the calibration magnetic field away from the magnetic sensor array 210, while the calibration magnetic field provided to the magnetic sensor 520 become relatively weaker with respect to the environmental magnetic field. Also in addition to that, the accuracy of representing the spatial distribution of the magnetic field with basis vectors is degraded. Accordingly, it is preferred to limit the relative positional relationship between the magnetic sensor array 210 and the calibration magnetic field generating unit 144 to some extent.

Figure 20:
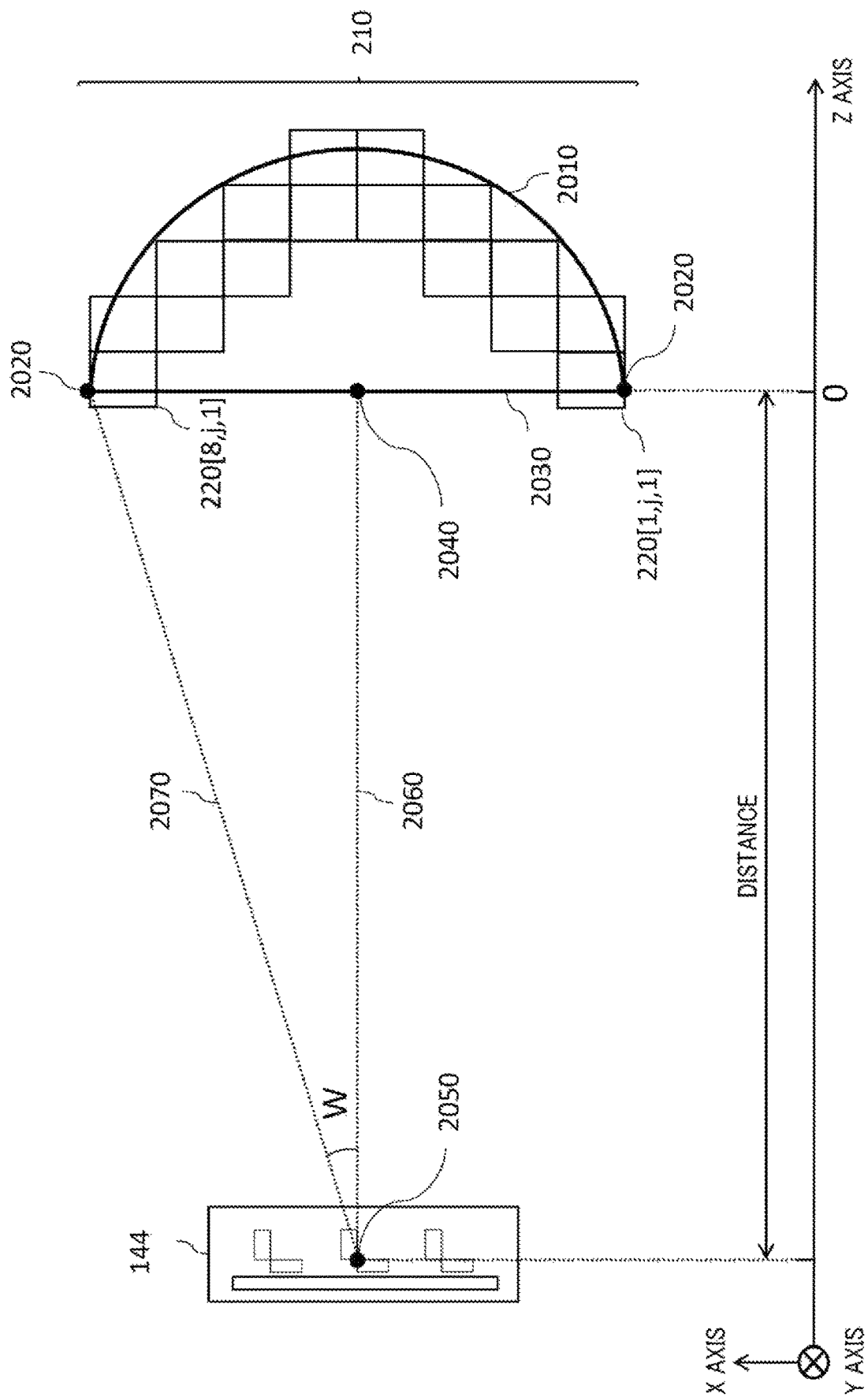
FIG. 20 illustrates a relative positional relationship between the magnetic sensor array 210 and the calibration magnetic field generating unit 144.

FIG. 20 illustrates a relative positional relationship between the magnetic sensor array 210 and the calibration magnetic field generating unit 144. As indicated in this figure, the magnetic sensor array 210 may be configured with the plurality of magnetic sensor cells three-dimensionally arrayed in an arc shape in a cross-sectional view. Herein, an angle is defined as an angle W, the angle being formed by the straight line 2060 connecting the center 2040 of a plane composed of a string 2030 connecting both end points 2020 of an arc 2010 and the center 2050 of the calibration magnetic field generating unit 114, and the straight line 2070 connecting the contact point 2020 between the arc 2010 and the string 2030 on the same cross section as the center 2040 of the plane, and the center of the calibration magnetic field generating unit 114. Herein, the string 2030 is defined by the lower limit position in the Z axis direction in the magnetic sensor 520 of the magnetic sensor cells 220 [1,j,1] and [8,j,1], and the position shall be the origin of the Z axis coordinates. Also, the distance from the magnetic sensor array 210 to the calibration magnetic field generating unit 144 is defined as the distance from the center 2040 of the plane composed of the string 2030 to the center 2050 of the calibration magnetic field generating unit 144.

Figure 21:
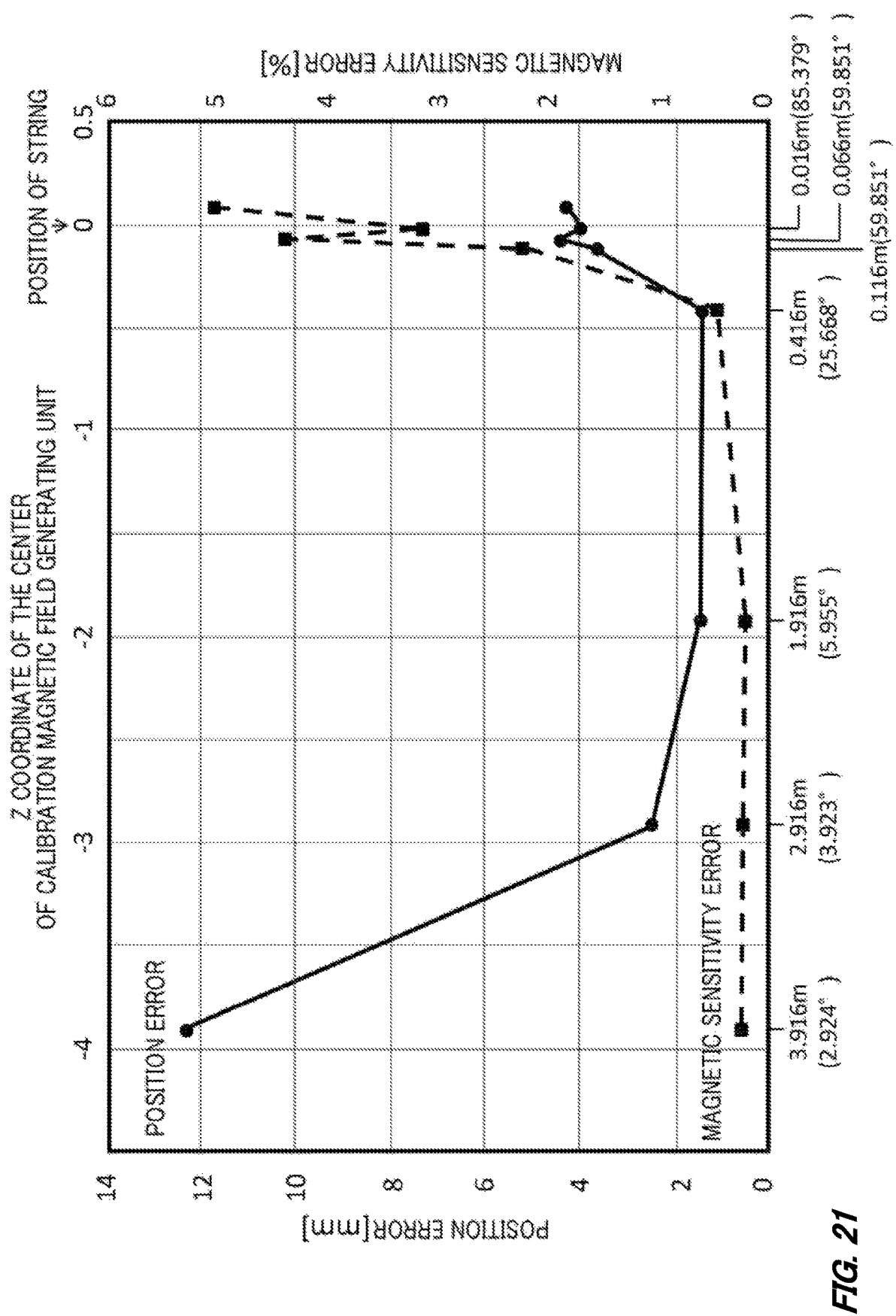
FIG. 21 illustrates a simulation result of the sensor error when the calibration magnetic field generating unit 144 is separated from the magnetic sensor array 210.

FIG. 21 illustrates a simulation result of the sensor error when the calibration magnetic field generating unit 144 is separated from the magnetic sensor array 210. Herein, in performing this simulation, the size of the sensor area of the magnetic sensor array 210 has been set to be about 40 cm wide, 20 cm deep, and 30 cm high. Also, the magnetic sensor array 210 and the calibration magnetic field generating unit 144 have been arranged so that the X axis and Y axis coordinates of the center 2040 of the plane composed of the string 2030 and the center 2050 of the calibration magnetic field generating unit 144 become the same. In this figure, the horizontal axis shows the Z coordinate of the center 2050 of the calibration magnetic field generating unit 144 in a unit of [m] when the position of the string 2030 is 0. That is, the absolute value of the horizontal axis in this figure indicates the distance from the magnetic sensor array 210 to the calibration magnetic field generating unit 144. Also, the value of the angle W calculated from the distance is shown at the bottom of this figure. Also in this figure, the left vertical axis shows the positional error in a unit of [mm], and the right vertical axis shows the magnetic sensitivity error in a unit of [%].

As shown in this figure, it can be seen that the positional error and magnetic sensitivity error of the magnetic sensor 520 begin to increase when the distance from the magnetic sensor array 210 to the calibration magnetic field generating unit 144 exceeds 1.916 m, that is, when the angle W is below 5.955°. This is thought to be caused by the fact that the calibration magnetic field generating unit 144, which is the calculation origin of the basis vectors calculated based on the position and magnetic sensitivity of each magnetic sensor 520 included in the magnetic sensor array 210, is too far away, so the space of the magnetic sensor array 210 remains in a part of the spatial distribution of the magnetic field represented by the basis vectors, and the accuracy of representing the spatial distribution of the magnetic field degrades. Therefore, in moving the calibration magnetic field generating unit 144 away from the magnetic sensor array 210, the calibration magnetic field generating unit 144 is preferred to be arranged so that the angle W formed by the straight line 2060 connecting the center 2040 of the plane composed of the string 2030 connecting the both end points 2020 of the arc 2010 and the center 2050 of the calibration magnetic field generating unit 144, and the straight line 2070 connecting the contact point 2020 between the arc 2010 and the string 2030 on the same cross section as the center 2040 of the plane, and the center 2050 of the calibration magnetic field generating unit 144, is greater than 6 degrees.

On the other hand, as shown in this figure, it can be seen that the positional error and magnetic sensitivity error of the magnetic sensor 520 begin to increase when the distance from the magnetic sensor array 210 to the calibration magnetic field generating unit 144 is below 0.416 m, that is, when the angle W exceeds 25.668°. This is thought to be caused by the distortion of the magnetic field caused by the magnetic flux concentrators 720 and 730. Therefore, it may be preferable to arrange the calibration magnetic field generating unit 144 so that the angle W is smaller than 26 degrees.

In the above description, the case where the distortion of the magnetic field caused by the magnetic flux concentrators 720 and 730 is suppressed by arranging the calibration magnetic field generating unit 144 away from the magnetic sensor array 210 is shown as one example. However, it is not limited to this. The magnetic field measuring apparatus 10 may suppress the distortion of the magnetic field caused by the magnetic flux concentrators 720 and 730 by dividing and calibrating the magnetic sensor array 210 instead of calibrating the entire array 210 collectively.

Figure 22:
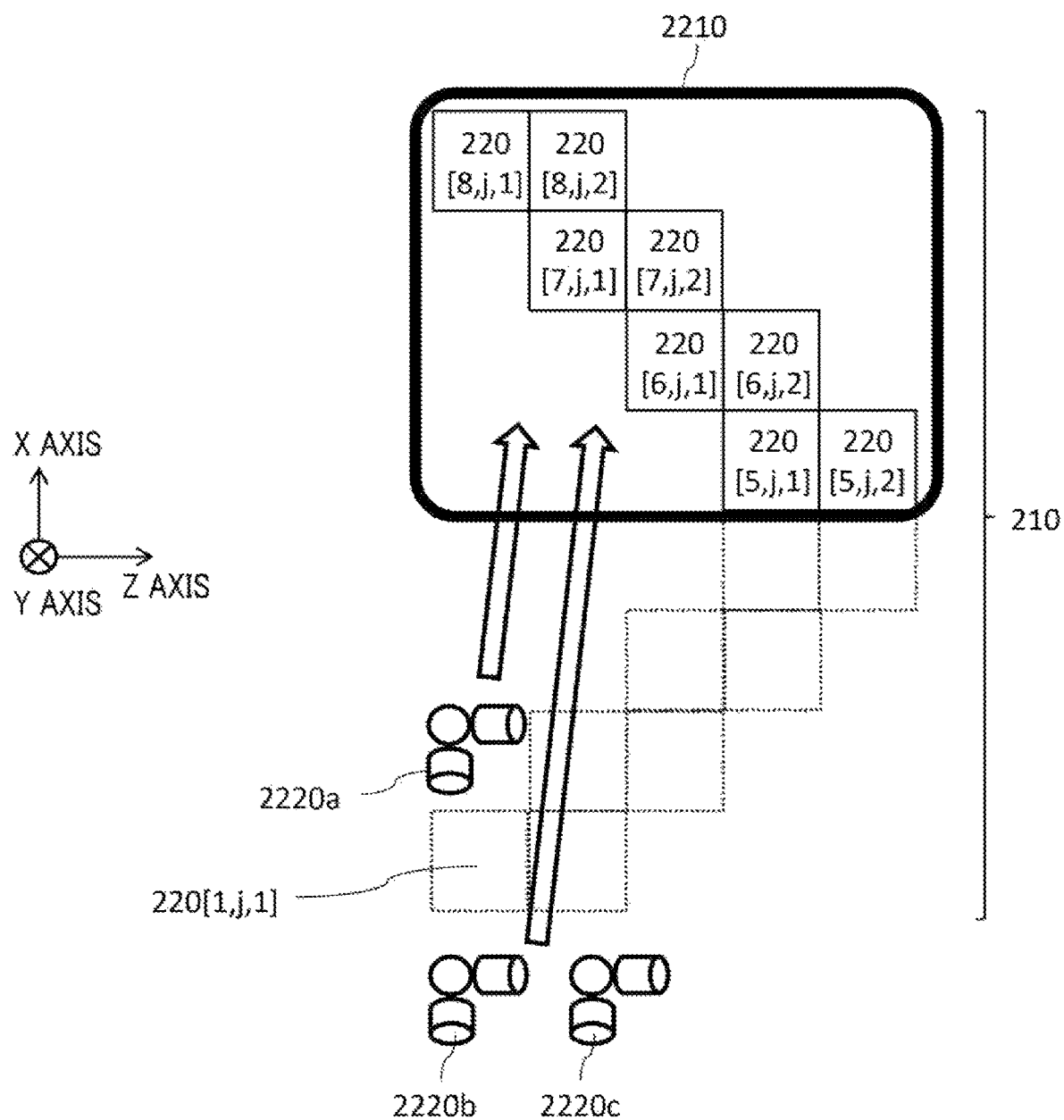
FIG. 22 illustrates one example of dividing calibration targeting a first magnetic sensor cell group 2210.

FIG. 22 illustrates one example of dividing calibration targeting a first magnetic sensor cell group 2210. In performing the dividing calibration, the measurement data acquiring unit 1120 may acquire the measurement data measured by a magnetic sensor cell group, which is at least a part of the plurality of magnetic sensor cells 220 in the magnetic sensor array 210. Also, the signal space separating unit 1160 may perform signal separation on the magnetic field spatial distribution indicated by the measurement data based on the position and magnetic sensitivity of each magnetic sensor 520 in the magnetic sensor cell group. Then, the calibration magnetic field generating unit 144 may generate the calibration magnetic field at a plurality of different positions. As one example, the calibration magnetic field generating unit 144 may have a plurality of three-axis calibration coils that each generate a calibration magnetic field in three orthogonal axial directions (for example, X, Y, and Z axis directions), as described above. Then, the magnetic field measuring apparatus 10 generates a calibration magnetic field from one or more first calibration coils 2220 arranged at the first position to calibrate the magnetic sensors 520 of the first magnetic sensor cell group 2210 among the plurality of magnetic sensor cells 220 configuring the magnetic sensor array 210. In this figure, a case is shown as one example where the sensor error is calibrated only for the magnetic sensors 520 of the magnetic sensor cells 220[5,j,1] to 220 [8,j,2] by generating a calibration magnetic field from a plurality of first calibration coils 2220a, 2220b, and 2220c (collectively referred to as "the first calibration coil 2220") arranged in the first position. In this case, the magnetic field measuring apparatus 10 uses the position of the first calibration coil 2220 as the coordinate origin in the calculation, and measures the calibration magnetic field generated at the first position by the first magnetic sensor cell group 2210 based on the position and magnetic sensitivity of the magnetic sensors 520 of the first magnetic sensor cell group 2210, in particular, based on the basis vectors calculated from the orthonormal functions and the position and magnetic sensitivity of the magnetic sensors 520. Then, the calibrating unit 1190 calibrates the sensor error in the magnetic sensor 520 of the first magnetic sensor cell group 2210 among the plurality of magnetic sensor cells 220 based on the separation error in the case where the signal separation has been performed on the spatial distribution of the calibration magnetic field generated at the first position. The procedure for calibrating the sensor error in the dividing calibration is the same as the procedure for calibrating the entire magnetic sensor array 210 collectively, except that the magnetic sensor 520 targeted for calibration is limited, so the description is omitted herein.

Figure 23:
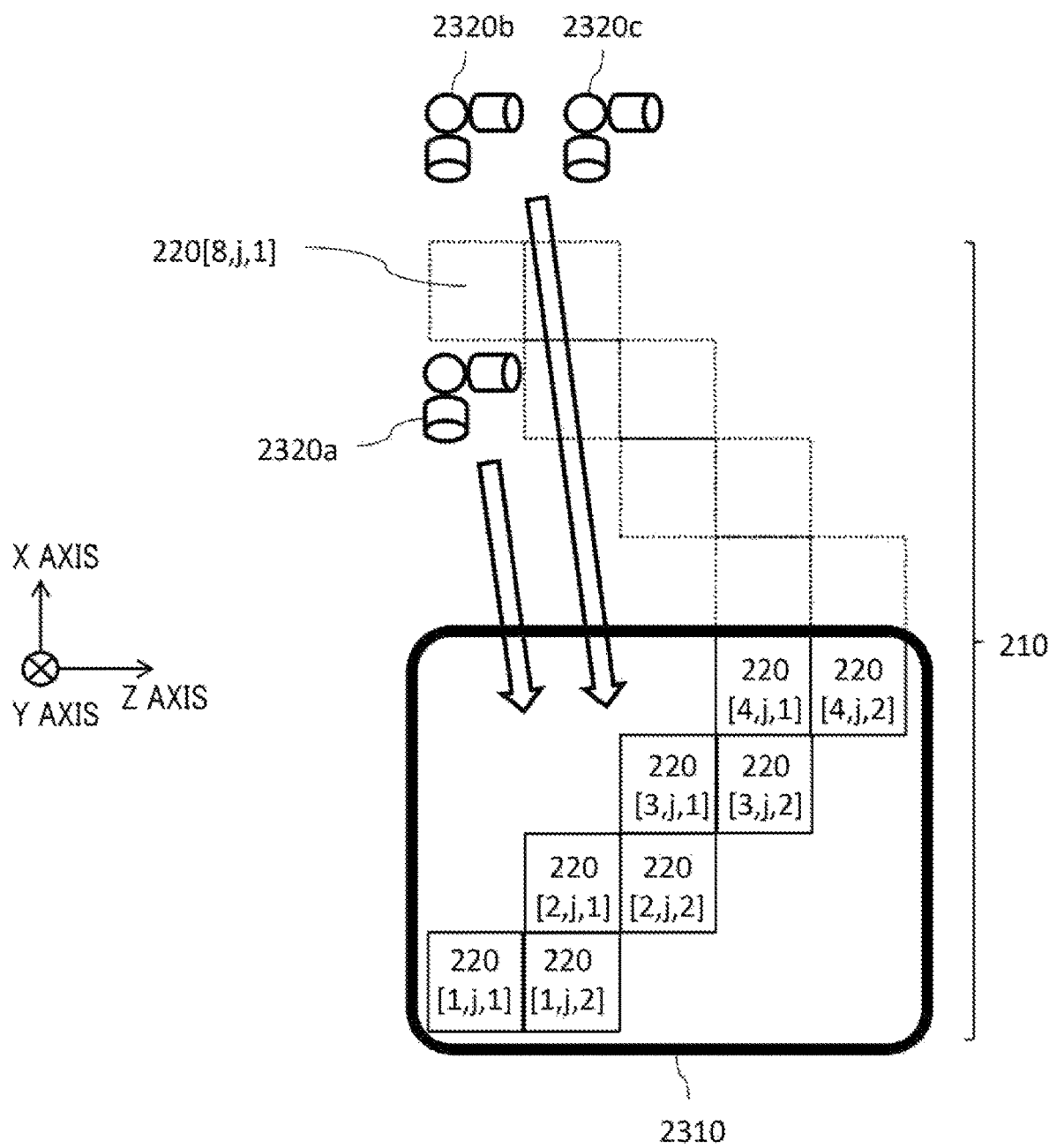
FIG. 23 illustrates one example of dividing calibration targeting a second magnetic sensor cell group 2310.

FIG. 23 illustrates one example of dividing calibration targeting a second magnetic sensor cell group 2310. The magnetic field measuring apparatus 10 generates a calibration magnetic field from one or more second calibration coils 2320 arranged at the second position to calibrate the magnetic sensors 520 of the second magnetic sensor cell group 2310 among the plurality of magnetic sensor cells 220 configuring the magnetic sensor array 210. In this figure, a case is shown as one example where the sensor error is calibrated only for the magnetic sensors 520 of the magnetic sensor cells 220[1,j,1] to 220[4,j,2] by generating a calibration magnetic field from a plurality of second calibration coils 2320a, 2320b, and 2320c (collectively referred to as "the second calibration coil 2320") arranged in the second position. In this case, the magnetic field measuring apparatus 10 uses the position of the second calibration coil 2320 as the coordinate origin in the calculation, and measures the calibration magnetic field generated at the second position by the second magnetic sensor cell group 2310 based on the position and magnetic sensitivity of the magnetic sensor 520 of the second magnetic sensor cell group 2310, in particular, based on the basis vectors calculated from the orthonormal functions and the position and magnetic sensitivity of the magnetic sensor 520. Then, the calibrating unit 1190 calibrates the sensor error in the magnetic sensor 520 of the second magnetic sensor cell group 2310 among the plurality of magnetic sensor cells 220 based on the separation error in the case where the signal separation has been performed on the spatial distribution of the calibration magnetic field generated at the second position.

In this way, the magnetic field measuring apparatus 10 may calibrate the entire magnetic sensor array 210 by sequentially repeating the dividing calibration. This enables the magnetic field measuring apparatus 10 to make the calibration magnetic field uniform to some extent by limiting the magnetic sensors 520 targeted for simultaneous calibration when viewed from each target magnetic sensor 520 to be calibrated, thus the distortion of the magnetic field caused by the magnetic flux concentrators 720 and 730 can be suppressed. Also, the magnetic field measuring apparatus 10 can divide and execute the calculations related to calibration, thereby executing the calculations at high speed.

In the above description, the case where the magnetic field measuring apparatus 10 divides the plurality of magnetic sensor cells 220 in the magnetic sensor array 210 into two groups is shown as one example, but it is not limited to this. The magnetic field measuring apparatus 10 may also, for example, divide the plurality of magnetic sensor cells 220 in the magnetic sensor array 210 into three or more groups. For example, the magnetic field measuring apparatus 10 may also divide the plurality of magnetic sensor cells 220 in the magnetic sensor array 210 into a first magnetic sensor cell group located on the left side when viewed from the body to be measured, a group of the second magnetic sensor cell group located on the right side when viewed from the body to be measured, and a third magnetic sensor cell group positioned between the first magnetic sensor cell group and the second magnetic sensor cell group. Then, the calibrating unit 1190 may calibrate the sensor error in the magnetic sensor 520 of the first magnetic sensor cell group based on the separation error in a case where signal separation has been performed on the spatial distribution of the calibration magnetic field generated at the first position, and calibrate the sensor error in the magnetic sensor 520 of the second magnetic sensor cell group based on the separation error in a case where signal separation has been performed on the spatial distribution of the calibration magnetic field generated at the second position, and calibrate the sensor error in the magnetic sensor 520 of the third magnetic sensor cell group based on the separation error in a case where signal separation has been performed on the spatial distribution of the calibration magnetic field generated at the third position.

Instead of this, the calibrating unit 1190 may also calibrate the sensor error in the magnetic sensors 520 of the first magnetic sensor cell group and third magnetic sensor cell group based on the separation error when the signal separation has been performed on the spatial distribution of the calibration magnetic field generated at the first position, and calibrate the sensor error in the magnetic sensors 520 of the second magnetic sensor cell group and third magnetic sensor cell group based on the separation error when the signal separation has been performed on the spatial distribution of the calibration magnetic field generated at the second position. That is, the magnetic field measuring apparatus 10 may also use the magnetic sensor 520 of the third magnetic sensor cell group as the common calibration target in both cases of generating the calibration magnetic field in the first position and generating the calibration magnetic field in the second position.

Also, in the above description, a case is shown as one example where the magnetic field measuring apparatus 10 separately include a calibration magnetic field generating unit 144 to generate the calibration magnetic field. However, it is not limited to this. The magnetic field measuring apparatus 10 may substitute a part of the magnetic sensor array 210 for the function of the calibration magnetic field generating unit 144. That is, the magnetic field measuring apparatus 10 may also generate a calibration magnetic field from the magnetic field generating unit 530 that is included in at least one magnetic sensor cell 220 of the plurality of magnetic sensor cells 220 in the magnetic sensor array 210. In this case, the at least one magnetic sensor cell 220 may further include a switching unit that switches whether the magnetic field generating unit 530 generates a feedback magnetic field or generates a calibration magnetic field.

In other words, the magnetic field measuring apparatus 10 may include a magnetic sensor array 210, which composed of an array of a plurality of magnetic sensor cells 220, each of the plurality of magnetic sensor cells 220 having a magnetic sensor 520 and a magnetic field generating unit 530, and in which the plurality of magnetic sensor cells 220 output signals corresponding to the magnetic field. Also, the magnetic field measuring apparatus 10 may include a calculating unit (for example, a signal space separating unit 1160) capable of calculating the magnetic field distribution in space based on the signals output by the plurality of magnetic sensor cells 220 and the magnetic sensor information indicating the information of the magnetic sensors 520. The magnetic sensor information may include the positions and magnetic sensitivities of magnetic sensors 520. Also, the magnetic field measuring apparatus 10 may include a calibrating unit 1190 for calibrating the magnetic sensor information. Then, the magnetic field generating unit 530 may be configured to generate a feedback magnetic field that reduces the magnetic field detected by the magnetic sensor 520 when detecting the magnetic field generated by the target object to be measured, and to generate a calibration magnetic field when calibrating the magnetic sensor cell 220. Also, the calibrating unit 1190 may calibrate the magnetic sensor information of the second magnetic sensor cell 220 different from the first magnetic sensor cell 220, according to the calibration magnetic field generated by the magnetic field generating unit 530 that is included in the first magnetic sensor cell 220 of the plurality of magnetic sensor cells 220. As a result, the magnetic field measuring apparatus 10 does not require a separately provided calibration magnetic field generating unit 144 to generate the calibration magnetic field, and the apparatus can be miniaturized.

Also, in the above description, it has been described that the calibration magnetic field generated by the calibration magnetic field generating unit 144 is preferably an alternating magnetic field with a frequency higher than 50 Hz (frequency f0>50 Hz), but when each magnetic sensor 520 includes the magnetic flux concentrators 720 and 730, the frequency of the alternating magnetic field may be further limited.

Figure 24:
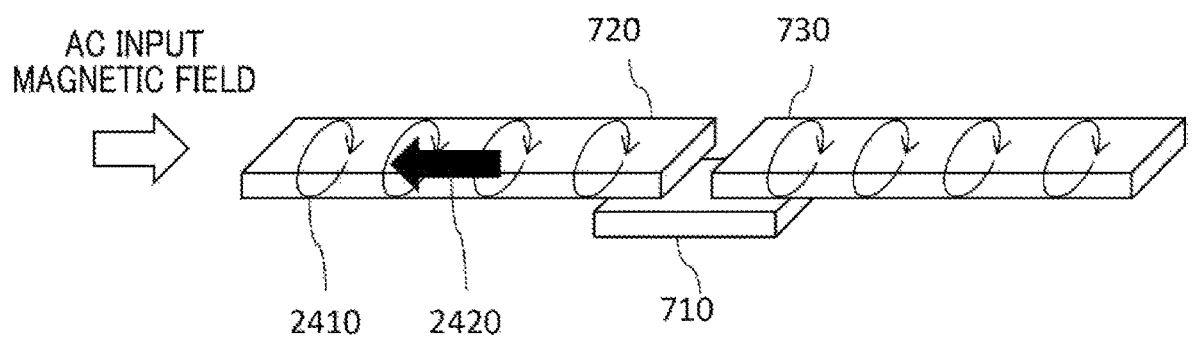
FIG. 24 illustrates a situation of eddy current occurring in the magnetic sensor 520 that includes magnetic flux concentrators 720 and 730.

FIG. 24 illustrates a situation of eddy current 2410 occurring in the magnetic sensor 520 that includes magnetic flux concentrators 720 and 730. Generally, when a conductor is moved in a magnetic field or when the magnetic flux density is changed, a spiral induced current occurs in the conductor by electromagnetic induction. That is, when an alternating input magnetic field is given as the calibration magnetic field, an eddy current 2410 occurs in the magnetic flux concentrators 720 and 730 by electromagnetic induction due to the temporal variation of the magnetic field. Then, the eddy current 2410 causes a magnetic field 2420 in the opposite direction of the input magnetic field. In this way, as the frequency of the input magnetic field increases, the gain attenuates due to magnetic field 2420 caused by the eddy current 2410. That is, the magnetic flux concentrators 720 and 730 act as a low-pass filter to the magnetic field.

Figure 25:
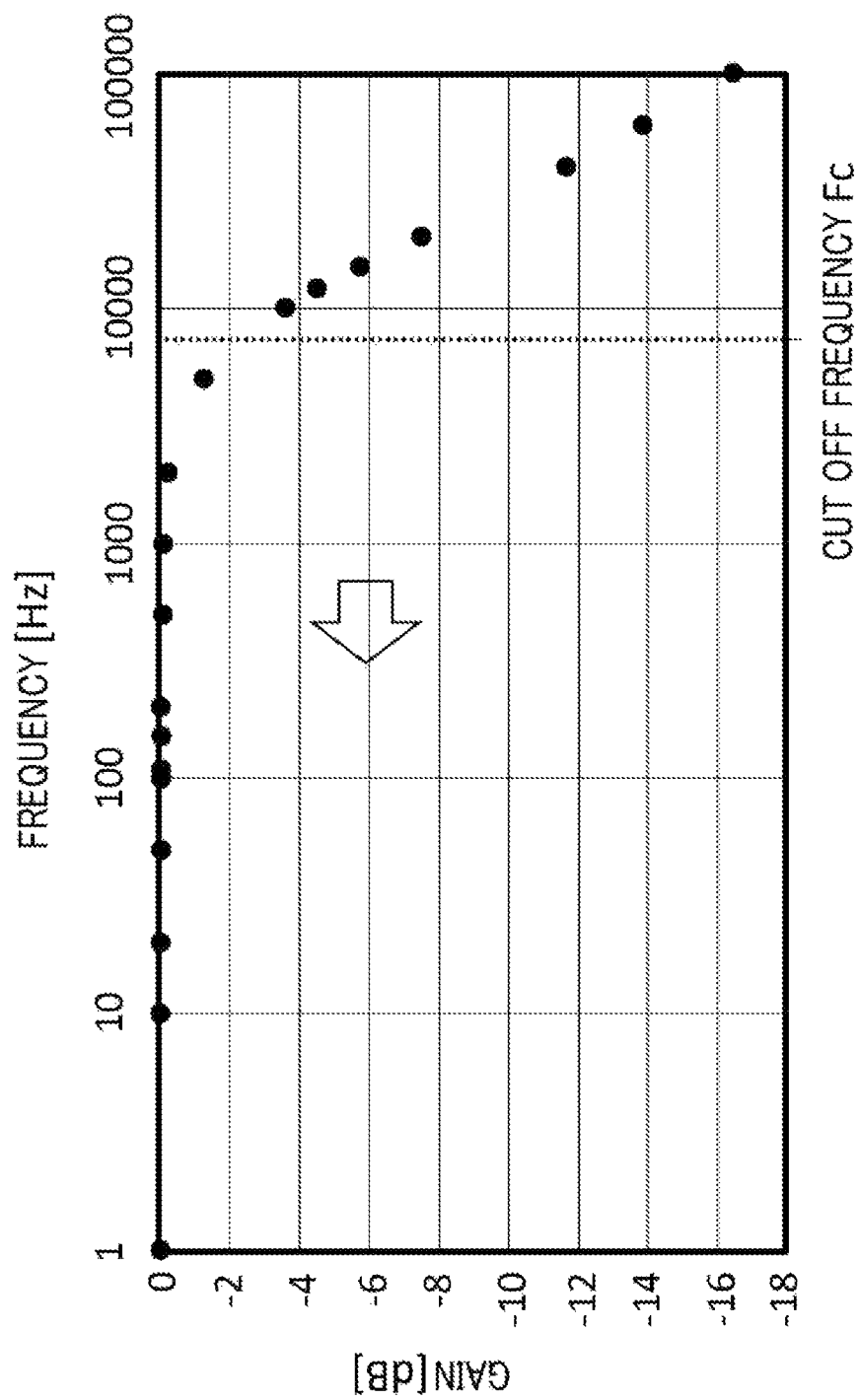
FIG. 25 illustrates a gain characteristic of a magnetic field resulting from an eddy current 2410.

FIG. 25 illustrates a gain characteristic of a magnetic field resulting from an eddy current 2410. In obtaining this property, the magnetic flux concentrators 720 and 730 have been made of a material of nickel-iron alloy (Ni—Fe) and their size has been 1 mm×1 mm×25 mm. As shown in this figure, the gain is flat up to a frequency of around 1 kHz, but the gain starts to attenuate after exceeding 1 kHz, and it can be seen that there is a cutoff frequency Fc before 10 kHz. Therefore, when the magnetic sensor 520 includes magnetic flux concentrators 720 and 730, the frequency of the alternating magnetic field generated by the calibration magnetic field generating unit 144 as the calibration magnetic field is preferred to be lower than or equal to the cutoff frequency of the attenuation property of the magnetic field by the magnetic flux concentrators 720 and 730, for example, lower than or equal to 1 kHz, which is the region where the gain is flat.

Further, other than the commercial power supply (50 Hz or 60 Hz), there are other environmental magnetic fields, for example, ventilation fan noise. Such a ventilation fan noise has a frequency of 20 Hz and can affect as the disturbance up to approximately the fourth harmonic. Therefore, the frequency of the alternating magnetic field to be generated as a calibration magnetic field is preferred to be higher than 80 Hz and lower than or equal to the cutoff frequency of the attenuation property of the magnetic field by the magnetic flux concentrators 720 and 730, and more preferably, the frequency is preferred to be further multiplied by 50 Hz or 60 Hz and avoid multiplying by 20 Hz. In this way, according to the magnetic field measuring apparatus 10, a region where the calibration magnetic field where the effect of the attenuation of gain caused by the magnetic flux concentrators 720 and 730 is minimal can be used, while suppressing the environmental magnetic field to the order of several tens of pT.

The seventh aspect of the present invention provides a magnetic field measuring apparatus. A magnetic field measuring apparatus may include a magnetic sensor array, which has a curved surface shape curved in at least one direction, is configured so that a plurality of magnetic sensor cells are three-dimensionally arrayed at grid points included in the curved surface shape, and is capable of detecting the input magnetic field in three axial directions, each of the plurality of magnetic sensor cells having a magnetic sensor, an output unit for outputting an output signal, and a magnetic field generating unit for generating a feedback magnetic field that has a magnitude corresponding to the output signal and that reduces the input magnetic field detected by the magnetic sensor. The magnetic field measuring apparatus may include a measurement data acquiring unit for acquiring the measurement data measured by the magnetic sensor array. The magnetic field measuring apparatus may include a signal space separating unit for performing signal separation on the spatial distribution of the magnetic field indicated by the measurement data based on the basis vectors calculated from the orthonormal functions and the position and magnetic sensitivity of each magnetic sensor of the magnetic sensor array. The magnetic field measuring apparatus may include a calibrating unit for calibrating the sensor error in the magnetic sensor based on the separation error in the case of performing signal separation on the spatial distribution of the calibration magnetic field generated by the magnetic field generating unit included in at least one magnetic sensor cell of the plurality of magnetic sensor cells.

The output unit may output an output signal corresponding to the feedback current that the magnetic field generating unit applies to generate the feedback magnetic field.

Each of the magnetic sensors may include a magnetoresistive element and two magnetic flux concentrators arranged at both ends of the magnetoresistive element, and the magnetoresistive element may be arranged at a position sandwiched between the two magnetic flux concentrators.

The magnetic field generating unit may include a feedback coil wound along the axial direction of the magnetic field being a detection target of the magnetic sensor, so as to enclose the magnetoresistive element and the two magnetic flux concentrators.

The calibrating unit may calibrate the sensor error in the magnetic sensor based on the respective separation errors when at least one of the magnetic sensor cells is switched sequentially.

The magnetic sensor array is configured with a plurality of magnetic sensor cells three-dimensionally arrayed in a circular arc in the cross-sectional view, and the calibrating unit may calibrate the sensor error in the magnetic sensor based on the respective separation errors when at least one of the magnetic sensor cells is sequentially switched over a plurality of magnetic sensor cells forming the inner arc.

At least one magnetic sensor cell may further include a switching unit that switches whether the magnetic field generating unit generates a feedback magnetic field or generates a calibration magnetic field.

In performing signal separation on the spatial distribution of the calibration magnetic field, the signal space separating unit may use the position where the magnetic field generating unit included in at least one magnetic sensor cell is arranged as the coordinate origin in calculation.

The calibrating unit may calibrate the sensor error by changing the basis vectors.

The calibrating unit may optimize the basis vectors to minimize the separation error.

The magnetic field measuring apparatus may further include a synchronous detection unit for detecting the calibration magnetic field, which is an alternating magnetic field, using a signal of the frequency of the alternating magnetic field.

The frequency of the alternating magnetic field may be higher than the frequency band of the target magnetic field to be measured.

The eighth aspect of the present invention provides a magnetic field measuring method. The magnetic field measuring method may include acquiring the measurement data measured by the magnetic sensor array, which has a curved surface shape curved in at least one direction, is configured so that a plurality of magnetic sensor cells are three-dimensionally arrayed at grid points included in the curved surface shape, and is capable of detecting the input magnetic field in three axial directions, each of the plurality of magnetic sensor cells having a magnetic sensor, an output unit for outputting an output signal, and a magnetic field generating unit for generating a feedback magnetic field that has a magnitude corresponding to the output signal and that reduces the input magnetic field detected by the magnetic sensor. The magnetic field measuring method may include performing signal separation on the spatial distribution of the magnetic field indicated by the measurement data, based on the basis vectors calculated from the orthonormal functions and the position and magnetic sensitivity of each magnetic sensor of the magnetic sensor array. The magnetic field measuring method may include generating a calibration magnetic field from the magnetic field generating unit included in at least one magnetic sensor cell of the plurality of magnetic sensor cells. The magnetic field measuring method may include calibrating the sensor error in the magnetic sensor based on the separation error in the case of performing signal separation on the spatial distribution of the calibration magnetic field.

The ninth aspect of the present invention provides a recording medium with magnetic field measuring program recorded thereon. The magnetic field measuring program may be executed by a computer. The magnetic field measuring program may cause the computer to function as a measurement data acquiring unit for acquiring the measurement data measured by the magnetic sensor array, which has a curved surface shape curved in at least one direction, is configured so that a plurality of magnetic sensor cells are three-dimensionally arrayed at grid points included in the curved surface shape, and is capable of detecting the input magnetic field in three axial directions, each of the plurality of magnetic sensor cells having a magnetic sensor, an output unit for outputting an output signal, and a magnetic field generating unit for generating a feedback magnetic field that has a magnitude corresponding to the output signal and that reduces the input magnetic field detected by the magnetic sensor. The magnetic field measuring program may cause the computer to function as a signal space separating unit for performing signal separation on the spatial distribution of the magnetic field indicated by the measurement data based on the basis vectors calculated from the orthonormal functions and the position and magnetic sensitivity of each magnetic sensor of the magnetic sensor array. The magnetic field measuring program may cause the computer to function as a calibrating unit for calibrating the sensor error in the magnetic sensor based on the separation error in the case of performing signal separation on the spatial distribution of the calibration magnetic field generated by the magnetic field generating unit included in at least one of the plurality of magnetic sensor cells.

A tenth aspect of the present invention provides a magnetic field measuring apparatus. A magnetic field measuring apparatus may include a magnetic sensor array, which is configured so that a plurality of magnetic sensor cells are three-dimensionally arrayed, and is capable of detecting an input magnetic field in three axial directions, each of the plurality of magnetic sensor cells having a magnetic sensor, an output unit for outputting an output signal, and a magnetic field generating unit for generating a feedback magnetic field that has a magnitude corresponding to the output signal and that reduces the input magnetic field detected by the magnetic sensor. The magnetic field measuring apparatus may include a measurement data acquiring unit for acquiring the measurement data measured by the magnetic sensor array. The magnetic field measuring apparatus may include a signal space separating unit for performing signal separation on the spatial distribution of the magnetic field indicated by the measurement data based on the basis vectors calculated from the orthonormal functions and the position and magnetic sensitivity of each magnetic sensor of the magnetic sensor array. The magnetic field measuring apparatus may include a calibrating unit for calibrating the sensor error in the magnetic sensor based on the separation error in the case of performing signal separation on the spatial distribution of the calibration magnetic field generated by the magnetic field generating unit included in at least one of the plurality of magnetic sensor cells.

Figure 26:
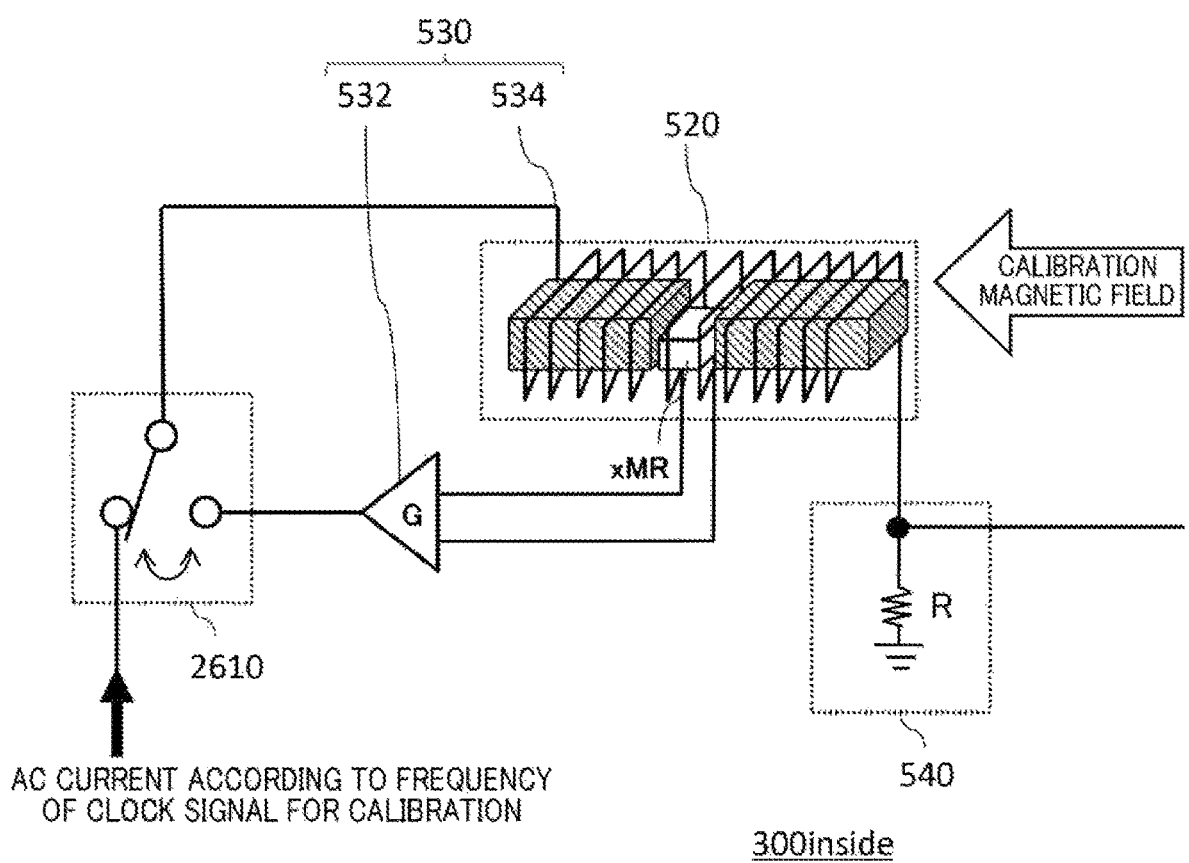
FIG. 26 illustrates a configuration of a sensor unit 300 inside that is included in the inner magnetic sensor cell 220 in the magnetic sensor array 210 according to a modification example of this embodiment.

FIG. 26 illustrates a configuration of a sensor unit 300 inside that is included in the inner magnetic sensor cell 220 in the magnetic sensor array 210 according to a modification example of this embodiment. In FIG. 26, members having the same function and configuration as in FIG. 5 are given the same reference numerals, and the following describes only differing points. As shown in this figure, the sensor unit 300 inside further has a switching unit 2610, the sensor unit 300 inside being included in the inner magnetic sensor cell 220 in the magnetic sensor array 210, that is, the plurality of magnetic sensor cells 220 [1,j,1] to 220 [8,j,1] forming the inner arc 915 of the magnetic sensor array 210.

The switching unit 2610 switches whether the magnetic field generating unit 530 generates a feedback magnetic field or generates a calibration magnetic field. That is, at least one sensor cell 220 of the plurality of magnetic sensor cells 220 in the magnetic sensor array 210 further has a switching unit 2610 that switches whether the magnetic field generating unit 530 generates a feedback magnetic field or generates a calibration magnetic field. In more detail, the switching unit 2610 is composed of a switch, with one end of the switch being connected to one end of the feedback coil 534. Then, the switching unit 2610 switches whether one end of the feedback coil 534 receives the output of the amplifier circuit 532, or alternating current corresponding to the frequency of the clock signal for calibration described below. When the switching unit 2610 switches to input the alternating current corresponding to the frequency of the clock signal for calibration to one end of the feedback coil 534, the magnetic field generating unit 530 generates a calibration magnetic field from the feedback coil 534.

Such a calibration magnetic field may be an alternating magnetic field. As one example, the calibration magnetic field may be a sine-wave of frequency f0, or may be a sum of sine waves of a plurality of frequencies (for example, frequency f0, frequency f1 (>frequency f0), and frequency f2 (>frequency f1) and so on). There is no DC component in the cardiac magnetic field, which is one of the magnetic fields to be measured by the magnetic field measuring apparatus 10. Accordingly, the magnetic field measuring apparatus 10 has no need to perform a calibration of a magnetic sensor to the DC offset of the magnetic sensor and the offset drift of a very low frequency (for example, 0.1 Hz or less), only performing the calibration of the magnetic sensor using the calibration magnetic field that is an alternating magnetic field.

Herein, generally, the environmental magnetic field is smaller at a higher frequency. For example, the environmental magnetic field is on the order of several tens of pT in the band higher than 50 Hz, which is the same level as the peak of the cardiac magnetic field, one of the target magnetic fields to be measured by the magnetic field measuring apparatus 10 according to this embodiment. Accordingly, the magnetic field generating unit 530 may generate an alternating magnetic field with a frequency higher than 50 Hz (frequency f0>50 Hz) as a calibration magnetic field. That is, since the signal frequency of the cardiac magnetic field is mostly lower than 20 Hz, the frequency of the alternating magnetic field as a calibration magnetic field may be higher than the frequency band of the target magnetic field to be measured.

Also in general, for example, 50 Hz or 60 Hz is used as the frequency of a commercial power supply. Therefore, there is a power supply noise at multiples of the frequency of these commercial power supplies. Accordingly, it is preferred that the magnetic field generating unit 530 use a frequency higher than the frequency of the target magnetic field to be measured, but avoiding a frequency that is a multiple of the frequency of the commercial power supply, as the frequency of the alternating magnetic field. As one example, it is preferred that the magnetic field generating unit 530 uses a frequency higher than 50 Hz, but avoiding a frequency that is a an integer multiple of 50 Hz or 60 Hz as the frequency of the calibration magnetic field. In this way, since the environmental magnetic field can be suppressed to the order of several tens of pT, the magnetic field generating unit 530 only needs to generate a calibration magnetic field weak enough to neglect the environmental noise of, for example, approximately several tens of nT. That is, by using such a frequency as the frequency of the alternating magnetic field, the magnetic field measuring apparatus 10 does not need to generate a strong magnetic field as the calibration magnetic field.

Also, when performing a calibration using such an alternating magnetic field, it is necessary to suppress the generation of an eddy current. Therefore, a housing of the feedback coil 534 for generating the calibration magnetic field may be formed of a resin material or the like with a low electrical conductivity. Also similarly, a housing that stores the magnetic sensor array 210 for measuring the calibration magnetic field is preferred to be formed of a resin material or the like with low electrical conductivity.

Figure 27:
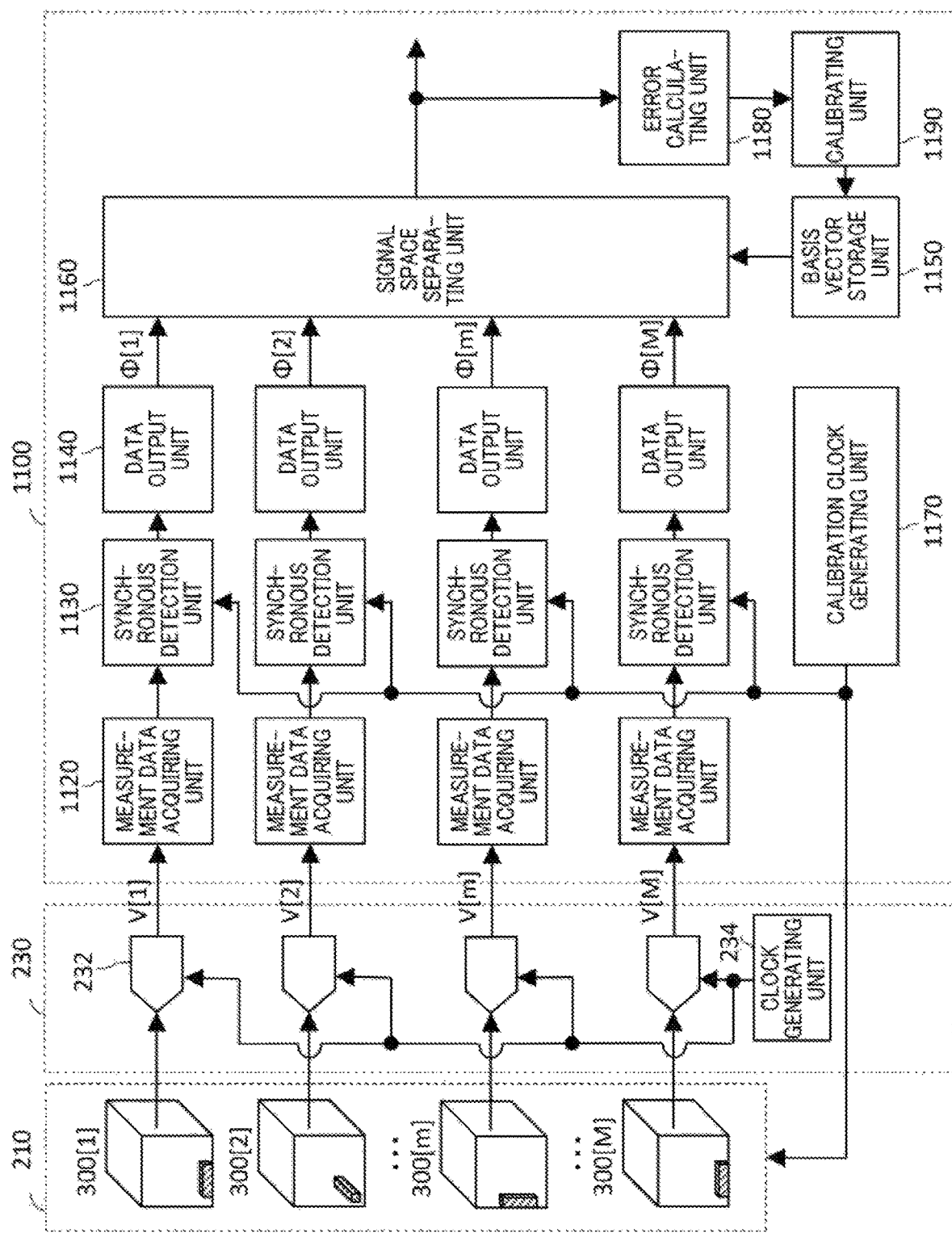
FIG. 27 illustrates a configuration of the magnetic sensor array 210, a sensor data gathering unit 230 and a sensor data processing unit 1100 according to a modification example of this embodiment.

FIG. 27 illustrates a configuration of the magnetic sensor array 210, a sensor data gathering unit 230 and a sensor data processing unit 1100 according to a modification example of this embodiment. In FIG. 27, members having the same function and configuration as in FIG. 11 are given the same reference numerals, and the following describes only differing points. In this figure, the calibration clock generating unit 1170 supplies the alternating current corresponding to the frequency of the generated clock signal to the magnetic sensor array 210 instead of the calibration magnetic field generating unit 144. In response to this, the magnetic sensor array 210 sequentially switches at least one magnetic sensor cell 220 that generates a calibration magnetic field from the magnetic field generating unit 530 one by one over a plurality of magnetic sensor cells 220[1,j,1] to 220[8,j,1] that form the inner arc 915, and sequentially generates an alternating magnetic field corresponding to the frequency of the clock signal from the feedback coil 534 of the sensor unit 300 inside that is included in the corresponding magnetic sensor cell 220. Also, the plurality of synchronous detection units 1130 detect the alternating calibration magnetic field generated by the magnetic field generating unit 530 included in at least one magnetic sensor cell, respectively, according to the clock signal.

Figure 28:
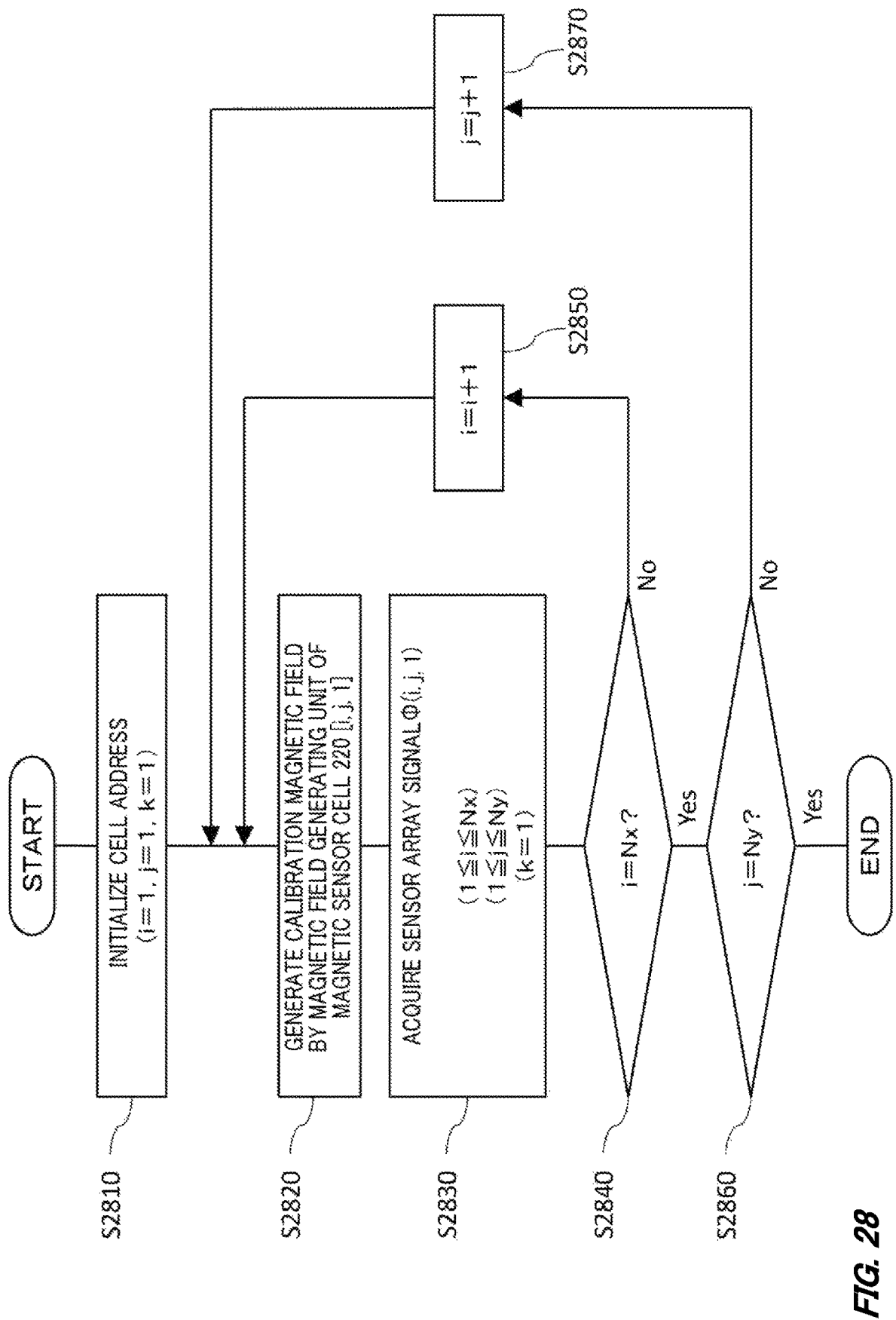
FIG. 28 illustrates a flow for the magnetic field measuring apparatus 10 according to a modification example of this embodiment to acquire a sensor array signal Φ(i,j,1) for calibration.

FIG. 28 illustrates a flow for the magnetic field measuring apparatus 10 according to a modification example of this embodiment to acquire a sensor array signal $\Phi(i,j,1)$ for calibration. Herein, i indicates a specific position of the magnetic sensor cells 220 in the magnetic sensor array 210 in the X direction and is an integer that satisfies $1 \leq i \leq Nx$ (where Nx indicates the number of magnetic sensor cells 220 arranged in the specific X direction among all of the arranged magnetic sensor cells 220). Also, j indicates a specific position of the magnetic sensor cells 220 in the magnetic sensor array 210 in the Y direction and is an integer that satisfies $1 \leq j \leq Ny$ (where Ny indicates the number of magnetic sensor cells 220 arranged in the specific Y direction among all of the arranged magnetic sensor cells 220). Also, k indicates the position of the magnetic sensor cell 220 in the magnetic sensor array 210 in the Z direction, and in this flow, z is fixed to 1. Further, in the explanation of this flow and the flow in FIG. 16 following this flow, one example where the M/2 sensor units 300 included in the plurality of magnetic sensor cells 220 that form the inner arc 915 of the M sensor units 300 sequentially generate the calibration magnetic field, and the remaining M−1 sensor units 300 that do not generate the magnetic field take measurements is indicated. However, the number of sensor units 300 for generating the calibration magnetic field is not limited to this number, but can be realized from one depending on the parameter that performs calibration (for example, calibration of one component of position coordinates). Also, depending on the calibration parameters and the dimension of the basis vectors, the number of sensors that measure the magnetic field can also be changed, from the several sensors required to form the basis vectors (minimum is 3) to M−1 sensors that do not generate a magnetic field. Also, even if measurements are performed by M−1 sensor units 300 that do not generate a magnetic field, the number of the target sensor units 300 to be calibrated for sensor error may be less than M−1. For example, the sensor error may be calibrated for M/2 sensor units 300 that do not generate a calibration magnetic field. Also for example, the sensor error may be calibrated for the sensor units 300 included in a different magnetic sensor cell 220 than the magnetic sensor cell 220 that contains the sensor units 300 that have generated the calibration magnetic field.

In step 2810, the magnetic field measuring apparatus 10 initializes the cell address. As one example, the magnetic field measuring apparatus 10 substitutes 1 in i, 1 in j, and 1 in k. That is, the magnetic field measuring apparatus 10 designates the magnetic sensor cell 220 [1, 1, 1] as the first magnetic sensor cell 220 that generates the calibration magnetic field.

In step 2820, the magnetic field measuring apparatus 10 generates a calibration magnetic field from the magnetic field generating unit 530 that is included in the magnetic sensor cell 220[i, j, 1], for example, magnetic sensor cell 220[1, 1, 1], in step 2820 following step 2810. That is, the magnetic field measuring apparatus 10 switches the switching unit 2610 in the sensor unit 300 of the magnetic sensor cell 220 [i, j, 1] to the calibration mode, and causes an alternating current corresponding to the frequency of the clock signal for calibration supplied from the calibration clock generating unit 1170 to be input to one end of the feedback coil 534. Then, the magnetic field measuring apparatus 10 generates an alternating magnetic field corresponding to the frequency of the clock signal from the feedback coil 534 that is included in the magnetic sensor cell 220 [i, j, 1]. At this time, the calibration magnetic field generated by the feedback coil 534 that is included in the magnetic sensor cell 220 [i, j, 1] is close to the magnetic field generated by the magnetic-dipole. Then, the calibration magnetic field generated by the feedback coil 534 that is included in the magnetic sensor cell 220 [i, j, 1] corresponds to the component of the first term in Expression 6. In this case, by generating an alternating magnetic field of relatively high intensity from the feedback coil 534, the component of the second term in Expression 6, that is, the effect of the disturbance magnetic field, can be neglected during a calibration.

In step 2830, the magnetic field measuring apparatus 10 acquires the sensor array signal Φ(i, j, 1) in the case where the calibration magnetic field is generated from the feedback coil 534 that is included in the magnetic sensor cell 220 [i, j, 1]. In more detail, when the calibration magnetic field is generated from the feedback coil 534 included in the magnetic sensor cell 220 [i, j, 1], the measurement data acquiring unit 1120 acquires the respective measurement data V[1] to V[M] measured by the (M−1) sensor units 300 among the plurality of sensor units 300[1] to 300[M] included in the magnetic sensor array 210, but excepting for the sensor unit 300[P] that has generated the calibration magnetic field (where P is an integer of 1≤P≤M). Then, the synchronous detection unit 1130 receives the clock signal for calibration supplied by the calibration clock generating unit 1170, and synchronously detects the calibration magnetic field according to the clock signal. Then, the synchronous detection unit 1130 extracts the frequency components synchronized with the calibration magnetic field, which is an alternating magnetic field, from the measurement data V[1] to V[M], and supplies the measurement data V[1] to V[M] according to the extracted frequency components to the data output unit 1140, respectively. Then, the data output unit 1140 supplies, to the signal space separating unit 1160, the sensor array signal Φ(i,j,1) for calibration including respective sensor signal components Φ[1] to Φ[M] (except for t [P]) from the plurality (that is, m−1) of sensor units 300[1] to 300[M] excepting for sensor unit 300[P] that generates the calibration magnetic field in the case where the calibration magnetic field has been generated from the feedback coil 534 included in the magnetic sensor cell 220 [i,j,1], Φ[1] to Φ[M] being equivalent to the measurement data V[1] to V[M] supplied by the synchronous detection unit 1130. As a result, the signal space separating unit 1160 obtains the sensor array signal Φ(i, j, 1) for calibration in the case where the calibration magnetic field is generated from the feedback coil 534 that is included in the magnetic sensor cell 220[i, j, 1].

In step 2840, the magnetic field measuring apparatus 10 determines whether i is equal to Nxt. That is, the magnetic field measuring apparatus 10 determines whether the calibration magnetic field has been generated from the magnetic field generating unit 530 included in all of the magnetic sensor cells 220 arranged in the X direction. When it is determined that i is equal to Nx, that is, that the calibration magnetic field has been generated from the magnetic field generating unit 530 included in all the magnetic sensor cells 220 arranged in the X direction, the magnetic field measuring apparatus 10 proceeds the process to step 2860.

On the other hand, in step 2840, when it is determined that i is not equal to Nx, that is, that the calibration magnetic field is not generated from the magnetic field generating unit 530 included in all the magnetic sensor cells 220 arranged in the X direction, the magnetic field measuring apparatus 10 increments i to i=i+1 in step 2850 and returns the process to step 2820 to continue the flow.

In step 2860, the magnetic field measuring apparatus 10 determines whether j is equal to Ny. That is, the magnetic field measuring apparatus 10 determines whether the calibration magnetic field has been generated from the magnetic field generating unit 530 included in all the magnetic sensor cells 220 arranged in the Y direction. When it is determined that j is equal to Ny, that is, that the calibration magnetic field has been generated from the magnetic field generating unit 530 included in all the magnetic sensor cells 220 arranged in the Y direction, the magnetic field measuring apparatus 10 ends the flow of acquiring the sensor array signal Φ(i, j, 1) for calibration.

On the other hand, in step 2860, when it is determined that j is not equal to Ny, that is, that the calibration magnetic field is not generated from the magnetic field generating unit 530 included in all the magnetic sensor cells 220 arranged in the Y direction, the magnetic field measuring apparatus 10 increments j to j=j+1 in step 2870 and returns the process to step 2820 to continue the flow.

In this way, the magnetic field measuring apparatus 10 acquires the respective array signals Φ(i, j, 1) for calibration in the case where the calibration magnetic field is generated from the magnetic field generating unit 530 included in M/2 sensor units 300 included in the plurality of magnetic sensor cells 220 forming the inner arc 915, where i is from 1 to Nx, j is from 1 to Ny, and k=1.

In this way, the magnetic field measuring apparatus 10 according to a modification example of this embodiment may generate a calibration magnetic field from the magnetic field generating unit 530 that at least one magnetic sensor cell 220 of the plurality of magnetic sensor cells 220 in the magnetic sensor array 210 has. As a result, the magnetic field measuring apparatus 10 does not require a separately provided calibration magnetic field generating unit 144 to generate the calibration magnetic field, and the apparatus can be miniaturized.

In this way, according to the magnetic field measuring apparatus 10 of this embodiment, in calibrating the magnetic sensor array 210, the magnetic field measuring apparatus 10 generate a calibration magnetic field from the magnetic field generating unit 530 that is included in at least one magnetic sensor cell 220 of the plurality of magnetic sensor cells 220 in the magnetic sensor array 210. That is, the magnetic field measuring apparatus 10 generate a calibration magnetic field from the magnetic field generating unit 530 that is included in at least one sensor unit 300 of the plurality of sensor units 300 in the magnetic sensor array 210. Therefore, the magnetic field measuring apparatus 10 does not require a separately provided apparatus (such as a coil) to generate the calibration magnetic field in addition to the magnetic sensor array 210. Also, according to the magnetic field measuring apparatus 10 of this embodiment, the magnetic field measuring apparatus 10 calibrates the magnetic sensor array 210 based on the respective separation errors in the case where at least one magnetic sensor cell 220 that generates the calibration magnetic field from the magnetic field generating unit 530 is sequentially switched over a plurality of magnetic sensor cells 220 [1,j,1] to 220 [8,j,1] that form the inner arc 915. Therefore, the magnetic field measuring apparatus 10 can reduce the distance between the coil that generates the calibration magnetic field and the magnetic sensor 520 that is the target of calibration, and relatively strengthen the calibration magnetic field input to the magnetic sensor 520. This allows the magnetic field measuring apparatus 10 to improve the SNR in the calibration calculation. Further, since the magnetic field measuring apparatus 10 generates the calibration magnetic field from each of the magnetic field generating units 530 included in all of the plurality of magnetic sensor cells 220 forming the inner arc 915, the magnetic field measuring apparatus 10 can generate a magnetic-dipole magnetic field that has less bias with respect to the position and the direction of the magnetic field in the magnetic sensor array 210 as the calibration magnetic field used to calibrate the magnetic sensor array 210.

In the above description, a case has shown as one example where the magnetic field measuring apparatus 10 generates the calibration magnetic field by sequentially switching the magnetic field generating unit 530 included in the M/2 sensor units 300 included in the plurality of magnetic sensor cells 220 forming the inner arc 915 of the magnetic sensor array 210, but it is not limited to this. The magnetic field measuring apparatus 10 may also generate a calibration magnetic field by sequentially switching the M/2 sensor units 300 included in the magnetic sensor cells 220 located outside in addition to the magnetic sensor cells 220 located inside of the magnetic sensor array 210. That is, the magnetic field measuring apparatus 10 may sequentially switch the magnetic field generating units 530 included in all of the magnetic sensor cells 220 in the magnetic sensor array 210 to generate the calibration magnetic field. When the magnetic field measuring apparatus 10 sequentially switches the magnetic field generating units 530 included in the magnetic sensor cells 220 located inside of the magnetic sensor array 210 to generate the calibration magnetic field, the component of the second term in Expression 6 can be neglected during a calibration, as described above. On the other hand, when the magnetic field measuring apparatus 10 sequentially switches the plurality of magnetic sensor cells 220 that form the outer arc 925 of the magnetic sensor array 210 to generate the calibration magnetic field, the component of the first term in Expression 6 can be neglected during a calibration.

In this case, the magnetic field measuring apparatus 10 may calibrate the sensor error for all of the M sensor units 300 by sequentially calibrating each sensor error for (M−1) sensor units 300 except for the sensor unit 300[P] that has generated the calibration magnetic field, depending on the number of calibration parameters and the dimensionality of the basis vectors, as described above, while sequentially switching the magnetic field generating units 530 included in all of the magnetic sensor cells 220.

Instead of this, the magnetic field measuring apparatus 10 may generate the calibration magnetic field while sequentially switching the magnetic sensor cells 220 [1,j,1] to 220 [8,j,1] with M/2 sensor units 300 located inside, and sequentially calibrate each sensor error only for the sensor units 300 of the M/2 magnetic sensor cells 220 [1,j,2] to 220 [8,j,2] located outside. Similarly, the magnetic field measuring apparatus 10 may generate a calibration magnetic field while sequentially switching the magnetic sensor cells 220 [1,j,2] to 220 [8,j,2] with M/2 sensor units 300 located outside, and sequentially calibrate each sensor error only for the sensor units 300 of the M/2 magnetic sensor cells 220 [1,j,1] to 220 [8,j,1] located inside. That is, the magnetic field measuring apparatus 10 may divide and calibrate all the sensor errors of both the sensor units 300 of the M/2 magnetic sensor cells 220 located inside and the sensor units 300 of the M/2 magnetic sensor cells 220 located outside.

Also, in the above description, the case has been shown as one example where the magnetic field measuring apparatus 10 classifies the plurality of magnetic sensor cells 220 in the magnetic sensor array 210 into a group of inner magnetic sensor cells 220 and a group of outer magnetic sensor cells 220 and controls them, but it is not limited to this. For example, the magnetic field measuring apparatus 10 may divide the plurality of magnetic sensor cells 220 in the magnetic sensor array 210 into a group of magnetic sensor cells 220[1,j,1] to 220[4,j,2] on the left side and a group of magnetic sensor cells 220[5,j,1] to 220[8,j,2] on the right side when viewed from the body to be measured, and control them in the same way as mentioned above. That is, the magnetic field measuring apparatus 10 may generate the calibration magnetic field while sequentially switching the magnetic sensor cells 220 [1,j,1] to 220 [4,j,2] with M/2 sensor units 300 located on the left side, and calibrate the sensor error only for the sensor units 300 of M/2 magnetic sensor cells 220 [5,j,1] to 220 [8,j,2] located on the right side. Similarly, the magnetic field measuring apparatus 10 may generate the calibration magnetic field while sequentially switching the magnetic sensor cells 220 [5,j,1] to 220 [8,j,2] with M/2 sensor units 300 located on the right side, and calibrate the sensor error only for the sensor units 300 of M/2 magnetic sensor cells 220 [1,j,1] to 220 [4,j,2] located on the left side.

In this way, the magnetic field measuring apparatus 10 classifies the plurality of magnetic sensor cells 220 in the magnetic sensor array 210 into a first group of magnetic sensor cell 220 and a second group of magnetic sensor cell 220, generates a calibration magnetic field while sequentially switching the magnetic sensor cells 220 in the first group of magnetic sensor cell 220 to calibrate sequentially each sensor error for the sensor units 300 in the second group of magnetic sensor cell 200, and generates a calibration magnetic field while sequentially switching the magnetic sensor cells 220 in the second group of magnetic sensor cell 220 to calibrate sequentially each sensor error for the sensor units 300 in the first group of magnetic sensor cell 200.

The magnetic field measuring apparatus 10 may not generate the calibration magnetic field from all the magnetic sensor cells 220 in one group of magnetic sensor cells 220, in generating the calibration magnetic field while sequentially switching the magnetic sensor cells 220 in one group of magnetic sensor cells 220, and calibrating the sensor error for the sensor units 300 in the other group of magnetic sensor cells 220. That is, the magnetic field measuring apparatus 10 may generate a calibration magnetic field while sequentially switching a part of the magnetic sensor cells 220 in the first group of magnetic sensor cells 220, and calibrate the sensor error for the sensor units 300 in the second group of magnetic sensor cells 220. Similarly, the magnetic field measuring apparatus 10 may generate a calibration magnetic field while sequentially switching a part of the magnetic sensor cells 220 in the second group of magnetic sensor cells 220, and calibrate the sensor error for the sensor units 300 in the first group of magnetic sensor cells 220.

Also, in the above description, the case has been shown as one example where the magnetic field measuring apparatus 10 classifies the plurality of magnetic sensor cells 220 in the magnetic sensor array 210 into two groups, but it is not limited to this. The magnetic field measuring apparatus 10 may, for example, classify the plurality of magnetic sensor cells 220 in the magnetic sensor array 210 into three groups. For example, the magnetic field measuring apparatus 10 may classify the plurality of magnetic sensor cells 220 in the magnetic sensor array 210 into a first group of magnetic sensor cells 220 located on the left side when viewed from the body to be measured, a second group of magnetic sensor cells 220 located on the right side when viewed from the body to be measured, and a third group of magnetic sensor cells 220 located between the first group of magnetic sensor cells 220 and the second group of magnetic sensor cells 220. Then, the magnetic field measuring apparatus 10 may generate a calibration magnetic field while sequentially switching the magnetic sensor cells 220 in the first group of magnetic sensor cells 220 to calibrate the sensor error for the sensor units 300 in the second groups of magnetic sensor cells 220 and the third group of magnetic sensor cells 220. Similarly, the magnetic field measuring apparatus 10 may generate a calibration magnetic field while sequentially switching the magnetic sensor cells 220 in the second group of magnetic sensor cells 220 to calibrate the sensor error for the sensor units 300 in the first group of magnetic sensor cells 220 and the third group of magnetic sensor cells 220. That is, the magnetic field measuring apparatus 10 may use the sensor units 300 in the third group of magnetic sensor cells 220 as the common calibration target in both cases of generating the calibration magnetic field while sequentially switching the magnetic sensor cells 220 in the first group of magnetic sensor cells 220 and of generating the calibration magnetic field while sequentially switching the magnetic sensor cells 220 in the second group of magnetic sensor cells 220.

Also, in the above description, the case where the magnetic field measuring apparatus 10 measures the target magnetic field to be measured after performing the calibration is shown as an example. However, for example, if the frequency of the alternating magnetic field as the calibration magnetic field is higher than the frequency band of the target magnetic field to be measured, the magnetic field measuring apparatus 10 may perform the calibration and the measurement of the target magnetic field to be measured simultaneously. In this case, the magnetic field measuring apparatus 10 may separate the frequency of the calibration magnetic field signal and the target magnetic field signal to be measured using an LPF, HPF, or the like.

The magnetic field measuring apparatus 10 according to a modification example of this embodiment is composed of a magnetic sensor array 210 in which a plurality of magnetic sensor cells 220, each having a magnetic sensor 520 and a magnetic field generator 530, are arranged and the plurality of magnetic sensor cells 220 output signals corresponding to the magnetic field, a signal space separating unit 1160 that can calculate the magnetic field distribution in space based on the signals and the magnetic sensor information, and a calibration unit 1190 that calibrates the magnetic sensor information. The magnetic sensor information may include the positions and magnetic sensitivities of magnetic sensors 520. The magnetic field generating unit 530 is configured to generate a feedback magnetic field for reducing the magnetic field detected by the magnetic sensor 520 when detecting the magnetic field generated by the target object to be measured, and generates a feedback magnetic field that reduces the magnetic field detected by the magnetic sensor 520 when calibrating the magnetic sensor cells 220. The calibration unit 1190 may calibrate the magnetic sensor information of the second magnetic sensor cell 220 that is different from the first magnetic sensor cell 220 according to the calibration magnetic field generated by the magnetic field generating unit 530, which is included in the first magnetic sensor cell 220 of the plurality of magnetic sensor cells 220.

A variety of embodiments of the present invention may be described with reference to flowcharts and block diagrams, where the blocks may represent: (1) steps of processes in which operations are performed; or (2) sections of devices responsible for performing the operations. Certain steps and sections may be implemented by dedicated circuitry, programmable circuitry supplied together with computer readable instructions stored on the computer readable medium, and/or a processor supplied together with computer readable instructions stored on the computer readable medium. Dedicated circuitry may include digital and/or analog hardware circuits and may include integrated circuits (IC) and/or discrete circuits. Programmable circuitry may include reconfigurable hardware circuits including, for example, logical AND, logical OR, logical XOR, logical NAND, logical NOR, and other logical operations, and memory elements such as flip-flops, registers, field-programmable gate arrays (FPGA), programmable logic arrays (PLA) or other.

Computer readable medium may include any tangible device that can store instructions for execution by a suitable device, as a result, such that the computer readable medium having instructions stored thereon comprises a product including instructions which can be executed to create means for performing operations specified in the flowcharts or block diagrams. Examples of the computer-readable medium may include an electronic storage medium, a magnetic storage medium, an optical storage medium, an electromagnetic storage medium, a semiconductor storage medium, or the like. More specific examples of computer readable medium may include a floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a Blu-ray (registered trademark) disk, a memory stick, an integrated circuit card, or the like.

Computer readable instructions may include any of assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk (registered trademark), JAVA (registered trademark), C++, etc., and conventional procedural programming languages, such as the "C" programming language or similar programming languages.

Computer readable instructions may be provided to a processor of a general-purpose computer, an application specific computer, or other programmable data processing device, or to programmable circuitry, locally or via a local area network (LAN), wide area network (WAN) such as the Internet or other, to execute the computer readable instructions to create means for performing operations specified in the flowcharts or block diagrams. Examples of the processor include a computer processor, a processing unit, a microprocessor, a digital signal processor, a controller, a microcontroller, and the like.

Figure 29:
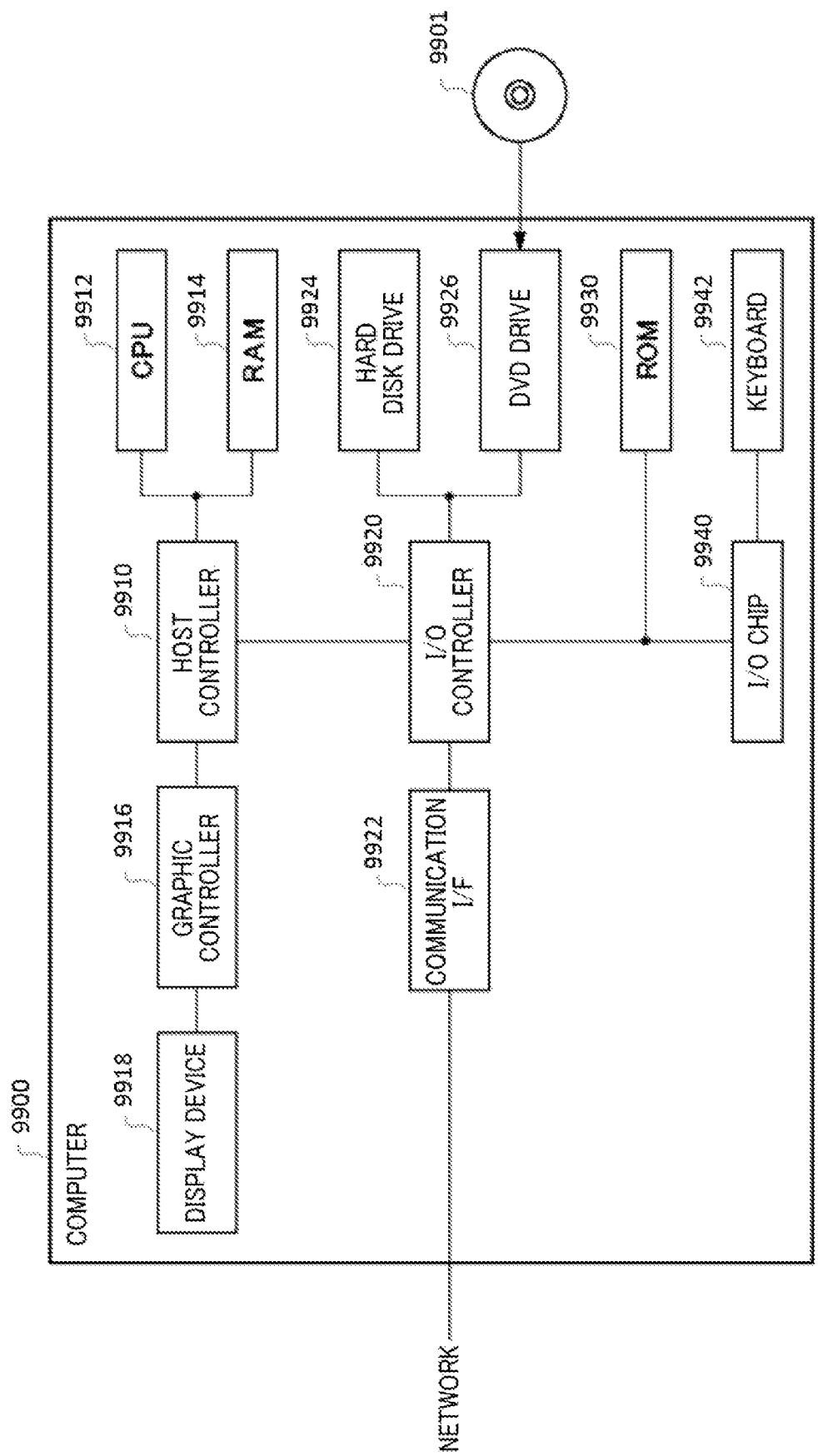
FIG. 29 illustrates an example of a computer 9900 that may embody a plurality of aspects of the present invention entirely or partially.

FIG. 29 illustrates an example of a computer 9900 in which the plurality of aspects of the present invention may be wholly or partially embodied. A program that is installed in the computer 9900 can cause the computer 9900 to function as or perform operations associated with the device according to the embodiments of the present invention or one or more sections of said device, or perform said operations or said one or more sections, and/or can cause the computer 9900 to perform the processes according to the embodiments of the present invention or steps of said processes. Such a program may be executed by the CPU 9912 to cause the computer 9900 to perform certain operations associated with some or all of the blocks of flowcharts and block diagrams described in this specification.

The computer 9900 according to this embodiment includes a CPU 9912, an RAM 9914, a graphic controller 9916, and a display device 9918, which are mutually connected by a host controller 9910. The computer 9900 also includes input/output units such as a communication interface 9922, a hard disk drive 9924, a DVD-ROM drive 9926 and an IC card drive, which are connected to the host controller 9910 via an input/output controller 9920. The computer also includes legacy input/output units such as an ROM 9930 and a keyboard 9942, which are connected to the input/output controller 9920 via an input/output chip 9940.

The CPU 9912 operates according to programs stored in the ROM 9930 and the RAM 9914, thus controlling each unit. The graphic controller 9916 obtains image data generated by the CPU 9912 on a frame buffer or other provided in the RAM 9914 or in itself, and causes the image data to be displayed on the display device 9918.

The communication interface 9922 communicates with other electronic devices via the network. The hard disk drive 9924 stores programs and data used by the CPU 9912 in the computer 9900. The DVD-ROM drive 9926 reads the programs or the data from the DVD-ROM 9901, and provides the hard disk drive 9924 with the programs or the data via the RAM 9914. The IC card drive reads programs and data from an IC card, and/or writes programs and data into the IC card.

The ROM 9930 stores therein a boot program or other to be executed by the computer 9900 when activated, and/or a program which depends on the hardware of the computer 9900. The input/output chip 9940 may also connect a variety of input/output units to the input/output controller 9920, via a parallel port, a serial port, a keyboard port, a mouse port, or other.

A program is provided by computer readable medium such as the DVD-ROM 9901 or an IC card. The program is read from the computer readable medium, installed into the hard disk drive 9924, RAM 9914, or ROM 9930, which are also examples of computer readable media, and executed by the CPU 9912. The information processing described in these programs is read into the computer 9900, which results in cooperation between a program and a variety of types of hardware resources mentioned above. The device or the method may be composed of realizing the operation or processing of information in accordance with the use of the computer 9900.

For example, when communication is executed between the computer 9900 and an external device, the CPU 9912 may execute a communication program loaded onto the RAM 9914 and instruct the communication interface 9922 to perform communication processing based on the processing described in the communication program. Under the control of the CPU 9912, the communication interface 9922 reads transmission data stored in a transmit buffer processing area provided in a recording medium such as the RAM 9914, the hard disk drive 9924, the DVD-ROM 9901, or the IC card, and then transmits the read transmission data to the network or writes reception data received from the network in a receive buffer processing area etc. provided in the recording medium.

In addition, the CPU 9912 may cause all or a necessary portion of a file or a database to be read into the RAM 9914, the file or the database having been stored in an external recording medium such as the hard disk drive 9924, the DVD-ROM drive 9926 (DVD-ROM 9901), the IC card or other, and perform a variety of types of processing on the data on the RAM 9914. The CPU 9912 may then write back the processed data to the external recording medium.

A variety of types of information, such as a variety of types of programs, data, tables, and databases, may be stored in the recording medium to undergo information processing. The CPU 9912 may perform a variety of types of processing on the data read from the RAM 9914, which includes a variety of types of operations, information processing, condition determination, conditional branch, unconditional branch, retrieval/replacement of information or other, as described anywhere throughout this disclosure and designated by an instruction sequence of programs, and writes the result back to the RAM 9914. In addition, the CPU 9912 may search for information in a file, a database, etc., in the recording medium. For example, if a plurality of entries are stored in the recording medium, where each entry has an attribute value of a first attribute associated with an attribute value of a second attribute, the CPU 9912 may retrieve an entry which matches the condition having a designated attribute value of the first attribute, from among said plurality of entries, and read the attribute value of the second attribute stored in said entry, thereby obtaining the attribute value of the second attribute associated with the first attribute which meets the predetermined condition.

The program or software modules described above may be stored in the computer readable medium on the computer 9900 or in the vicinity of the computer 9900. In addition, a recording medium such as a hard disk or an RAM provided in a server system connected to a dedicated communication network or the Internet can be used as the computer readable medium, thereby providing the program to the computer 9900 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: magnetic field measuring apparatus; 100: main unit; 110: magnetic sensor unit; 120: head; 125: driving unit; 130: base portion; 140: pole portion; 142: support portion; 144: calibration magnetic field generating unit; 150: information processing unit; 210: magnetic sensor array; 220: magnetic sensor cell; 230: sensor data gathering unit; 232: AD converter; 234: clock generating unit; 300: sensor unit; 520: magnetic sensor; 530: magnetic field generating unit; 532: amplifier circuit; 534: feedback coil; 540: output unit; 710: magnetoresistive element; 720, 730: magnetic flux concentrator; 1100: sensor data processing unit; 1120: measurement data acquiring unit; 1130: synchronous detection unit; 1140: data output unit; 1150: basis vector storage unit; 1160: signal space separating unit; 1170: calibration clock generating unit; 1180: error calculating unit; 1190: calibrating unit; 2210: first group of magnetic sensor cells; 2220: first calibration coil; 2310: second group of magnetic sensor cells; 2320: second calibration coil; 2610: switching unit; 9900: computer; 9901: DVD-ROM; 9910: host controller; 9912: CPU; 9914: RAM; 9916: graphics controller; 9918: display device; 9920: input/output controller; 9922: communication interface; 9924: hard disk drive; 9926: DVD-ROM drive; 9930: ROM; 9940: input/output chip; 9942: keyboard

What is claimed is:

1. A magnetic field measuring apparatus, comprising:
    at least one processor;
    a magnetic sensor array that is configured by arraying a plurality of magnetic sensor cells to form a surface covering at least a part of a target object to be measured, each of the plurality of magnetic sensor cells having a magnetic sensor;
    a measurement data acquiring unit configured to acquire, using the at least one processor, measurement data measured by a magnetic sensor cell group that is at least a part of the plurality of magnetic sensor cells in the magnetic sensor array;
    a calibration magnetic field generating unit configured to generate a calibration magnetic field at a plurality of different positions; and
    a calibrating unit configured to calibrate, using the at least one processor, a sensor error in the magnetic sensor of a first magnetic sensor cell group of the plurality of magnetic sensor cells based on the calibration magnetic field generated at a first position, and calibrating a sensor error in the magnetic sensor of a second magnetic sensor cell group of the plurality of magnetic sensor cells based on the calibration magnetic field generated at a second position, wherein
    the calibration magnetic field generating unit has at least three or more calibration coils, each of the calibration coils generating the calibration magnetic field in a different axial direction from other axial directions.

2. The magnetic field measuring apparatus according to claim 1, wherein the calibrating unit is further configured to calibrate, using the at least one processor, the sensor error in the magnetic sensor of the first magnetic sensor cell group of the plurality of magnetic sensor cells by minimizing an error between a sensor array signal from the measurement data and a vector of a least squares solution of the sensor array signal based on the calibration magnetic field generated at the first position, and calibrating the sensor error in the magnetic sensor of the second magnetic sensor cell group of the plurality of magnetic sensor cells by minimizing an error between the sensor array signal from the measurement data and the vector of the least squares solution of the sensor array signal based on the calibration magnetic field generated at the second position.

3. The magnetic field measuring apparatus according to claim 1, wherein the calibrating unit is further configured to calibrate, using the at least one processor, the sensor error in the magnetic sensor of the first magnetic sensor cell group and a third magnetic sensor cell group of the plurality of magnetic sensor cells, based on the calibration magnetic field generated at the first position, and calibrate the sensor error in the magnetic sensor of the second magnetic sensor cell group and the third magnetic sensor cell group of the plurality of magnetic sensor cells, based on the calibration magnetic field generated at the second position.

4. The magnetic field measuring apparatus according to claim 1, wherein:
    the magnetic sensor array is composed of the plurality of magnetic sensor cells three-dimensionally arrayed in an arc shape in a cross sectional view; and
    an angle formed by a straight line connecting the center of a plane composed of a string connecting both end points of an arc and the center of the calibration magnetic field generating unit, and a straight line connecting a contact point between the arc and the string on the same cross section as the center of the plane, and the center of the calibration magnetic field generating unit, is greater than 6 degrees.

5. The magnetic field measuring apparatus according to claim 1, wherein each of the plurality of magnetic sensor cells further comprises:
    a magnetic field generating unit for generating a feedback magnetic field to reduce an input magnetic field detected by the magnetic sensor; and
    an output unit for outputting an output signal corresponding to a feedback current that is to flow for the magnetic field generating unit to generate the feedback magnetic field.

6. The magnetic field measuring apparatus according to claim 4, wherein each of the plurality of magnetic sensor cells further comprises:
    a magnetic field generating unit for generating a feedback magnetic field to reduce an input magnetic field detected by the magnetic sensor; and an output unit for outputting an output signal corresponding to a feedback current that is to flow for the magnetic field generating unit to generate the feedback magnetic field.

7. The magnetic field measuring apparatus according to claim 5, wherein:
each of magnetic sensors, each magnetic sensor being identical to the magnetic sensor, includes a magnetoresistive element and two magnetic flux concentrators arranged on both ends of the magnetoresistive element;
the magnetoresistive element is arranged at a position sandwiched between the two magnetic flux concentrators.

8. The magnetic field measuring apparatus according to claim 7, wherein the magnetic field generating unit includes a feedback coil wound along an axial direction of a magnetic field being a detection target of the magnetic sensor, so as to enclose the magnetoresistive element and the two magnetic flux concentrators.

9. The magnetic field measuring apparatus according to claim 1, wherein the different axial direction is an axial direction orthogonal to other axial directions.

10. The magnetic field measuring apparatus according to claim 1, further comprising a signal space separating unit configured to perform, using the at least one processor, signal separation on a magnetic field spatial distribution indicated by the measurement data based on a position and a magnetic sensitivity of each magnetic sensor of the magnetic sensor cell group.

11. The magnetic field measuring apparatus according to claim 10, wherein the calibrating unit is configured to calibrate, using the at least one processor, the sensor error in the magnetic sensor of the first magnetic sensor cell group of the plurality of magnetic sensor cells based on a separation error in a case where signal separation has been performed based on the calibration magnetic field generated at the first position, and the sensor error in the magnetic sensor of the second magnetic sensor cell group of the plurality of magnetic sensor cells based on the separation error in a case where signal separation has been performed based on the calibration magnetic field generated at the second position.

12. The magnetic field measuring apparatus according to claim 10, wherein the signal space separating unit performs signal separation on the magnetic field spatial distribution based on basis vectors calculated from an orthonormal functions and the position and the magnetic sensitivity of each of the magnetic sensor.

13. The magnetic field measuring apparatus according to claim 12, wherein the calibrating unit calibrates the sensor error by changing the basis vectors.

14. The magnetic field measuring apparatus according to claim 13, wherein the calibrating unit optimizes the basis vectors so as to minimize an error between a sensor array signal from the measurement data and a vector of a least squares solution of the sensor array signal.

15. The magnetic field measuring apparatus according to claim 1, further comprising a synchronous detection unit configured to detect, using the at least one processor, the calibration magnetic field, which is an alternating magnetic field, using a signal of a frequency of the alternating magnetic field.

16. The magnetic field measuring apparatus according to claim 15, wherein the frequency of the alternating magnetic field is higher than 80 Hz, and lower than or equal to a cutoff frequency of an attenuation property of a magnetic field by a magnetic flux concentrator included in the magnetic sensor.

17. A magnetic field measuring apparatus, comprising:
at least one processor;
a magnetic sensor array that is configured by arraying a plurality of magnetic sensor cells to form a surface covering at least a part of a target object to be measured, each of the plurality of magnetic sensor cells having:
a magnetic sensor configured to detect a magnetic field: and
a magnetic field generating unit, wherein the magnetic field generating unit included in at least one magnetic sensor cell of the plurality of magnetic sensor cells in the magnetic sensor array is configured to (i) generate a feedback magnetic field that reduces the magnetic field detected by the magnetic sensor when detecting a magnetic field generated by the target object to be measured and (ii) generate a calibration magnetic field when calibrating the plurality of magnetic sensor cells;
a measurement data acquiring unit configured to acquire, using the at least one processor, measurement data measured by a magnetic sensor cell group that is at least a part of the plurality of magnetic sensor cells in the magnetic sensor array; and
a calibrating unit configured to calibrate, using the at least one processor, a sensor error in the magnetic sensor of a second magnetic sensor cell group different from a first magnetic sensor cell group of the plurality of magnetic sensor cells based on the calibration magnetic field generated at a first position of the first magnetic sensor cell group.

18. A magnetic field measuring apparatus, comprising:
at least one processor;
a magnetic sensor array that is configured by arraying a plurality of magnetic sensor cells to form a surface covering at least a part of a target object to be measured, each of the plurality of magnetic sensor cells having a magnetic sensor;
a measurement data acquiring unit configured to acquire, using the at least one processor, measurement data measured by a magnetic sensor cell group that is at least a part of the plurality of magnetic sensor cells in the magnetic sensor array;
a signal space separating unit configured to perform, using the at least one processor, signal separation on a magnetic field spatial distribution indicated by the measurement data based on a position and magnetic sensitivity of each magnetic sensor;
a calibration magnetic field generating unit configured to generate a calibration magnetic field at a position on a straight line that can be drawn without crossing the plurality of magnetic sensor cells from a measurement space outside the measurement space where the plurality of magnetic sensor cells are not arranged in the closed space that is composed of the smallest convex polygon that includes all of the plurality of magnetic sensor cells in a cross-sectional view; and
a calibrating unit configured to calibrate, using the at least one processor, a sensor error for the magnetic sensor based on a separation error in a case where the signal separation has been performed on a spatial distribution of the calibration magnetic field.

19. The magnetic field measuring apparatus according to claim 1, wherein the magnetic field measuring apparatus is configured to at least one of:
measure a cardiac magnetic field that is a magnetic field generated by an electrical activity of a human heart;

measure a cardiac magnetic field of a non-human living organism;
measure a biological magnetic field other than the cardiac magnetic field;
measure a biological magnetic field of a brain;
measure a biological magnetic field; or
magnetic particle testing for detecting surface and subsurface scratches of steel materials and welding portions.

\* \* \* \* \*